United States Patent
Besong et al.

(10) Patent No.: US 9,416,136 B2
(45) Date of Patent: Aug. 16, 2016

(54) PYRROLOPYRIMIDINE COMPOUNDS AND THEIR USES

(71) Applicants: Gilbert Besong, Cambridge (GB); Christopher Thomas Brain, Cambridge, MA (US); Clinton A Brooks, Beaufort, NC (US); Miles Stuart Congreve, Cambridge (GB); Claudio Dagostin, Cambridge (GB); Guo He, Cambridge, MA (US); Ying Hou, Cambridge, MA (US); Steven Howard, Cambridge (GB); Yue Li, Shanghai (CN); Yipin Lu, Emeryville, CA (US); Paul Mortenson, Cambridge (GB); Troy Smith, Cambridge, MA (US); Moo Je Sung, Cambridge, MA (US); Steven Woodhead, Cambridge (GB); Wojciech Wrona, Waltham, MA (US); Bharat Lagu, Cambridge, MA (US)

(72) Inventors: Gilbert Besong, Cambridge (GB); Christopher Thomas Brain, Cambridge, MA (US); Clinton A Brooks, Beaufort, NC (US); Miles Stuart Congreve, Cambridge (GB); Claudio Dagostin, Cambridge (GB); Guo He, Cambridge, MA (US); Ying Hou, Cambridge, MA (US); Steven Howard, Cambridge (GB); Yue Li, Shanghai (CN); Yipin Lu, Emeryville, CA (US); Paul Mortenson, Cambridge (GB); Troy Smith, Cambridge, MA (US); Moo Je Sung, Cambridge, MA (US); Steven Woodhead, Cambridge (GB); Wojciech Wrona, Waltham, MA (US); Bharat Lagu, Cambridge, MA (US)

(73) Assignees: Novartis AG, Basel (CH); Astex Therapeutics, Ltd., Cambridge (GB)

( * ) Notice: Subject to any disclaimer, the term of this patent is extended or adjusted under 35 U.S.C. 154(b) by 0 days.

(21) Appl. No.: 14/158,358

(22) Filed: Jan. 17, 2014

(65) Prior Publication Data
US 2014/0135312 A1    May 15, 2014

Related U.S. Application Data

(62) Division of application No. 13/060,154, filed as application No. PCT/EP2009/060793 on Aug. 20, 2009, now Pat. No. 8,685,980.

(60) Provisional application No. 61/091,037, filed on Aug. 22, 2008.

(51) Int. Cl.
| | | |
|---|---|---|
| A61K 31/519 | (2006.01) |
| A61P 35/04 | (2006.01) |
| C07D 487/04 | (2006.01) |
| C07D 487/08 | (2006.01) |

(52) U.S. Cl.
CPC ............ *C07D 487/08* (2013.01); *C07D 487/04* (2013.01)

(58) Field of Classification Search
CPC ........................... C07D 487/04; A61K 31/519
USPC ........................................ 544/280; 514/265.1
See application file for complete search history.

(56) References Cited

U.S. PATENT DOCUMENTS

| | | | |
|---|---|---|---|
| 7,713,994 | B2 | 5/2010 | Tsou et al. |
| 8,324,225 | B2 | 12/2012 | Brain et al. |
| 2008/0139588 | A1 | 6/2008 | Clark et al. |
| 2008/0167309 | A1 | 7/2008 | Berdini et al. |
| 2009/0318441 | A1 | 12/2009 | Brain et al. |
| 2011/0152244 | A1 | 6/2011 | Besong et al. |
| 2012/0207763 | A1 | 8/2012 | Brain et al. |

FOREIGN PATENT DOCUMENTS

| | | | |
|---|---|---|---|
| JP | 2006241089 A1 | 9/2006 |
| WO | 2003074530 A1 | 11/2003 |
| WO | 2004/022561 A1 | 3/2004 |
| WO | 2005023761 A1 | 3/2005 |
| WO | 2005023806 A2 | 3/2005 |
| WO | 2005080393 A1 | 9/2005 |
| WO | 2005085253 A1 | 9/2005 |
| WO | 2005107760 A1 | 11/2005 |
| WO | 2006042102 A2 | 4/2006 |
| WO | 2006045828 A1 | 5/2006 |
| WO | 2006074985 A1 | 7/2006 |
| WO | 2006076595 A1 | 7/2006 |
| WO | 2006091737 A1 | 8/2006 |
| WO | 2007030438 A1 | 3/2007 |
| WO | 2007039285 A1 | 4/2007 |
| WO | 2007058990 A2 | 5/2007 |

(Continued)

OTHER PUBLICATIONS

Fry (Molecular Cancer Therapeutics, 2004, 3(11), pp. 1427-1438).*

(Continued)

*Primary Examiner* — Susanna Moore
(74) *Attorney, Agent, or Firm* — Laura K. Madden

(57) ABSTRACT

The disclosed compounds relate to treatments and therapies for protein kinase-associated disorders. There is also a need for compounds useful in the treatment or prevention or amelioration of one or more symptoms of cancer, transplant rejections, and autoimmune diseases. Furthermore, there is a need for methods for modulating the activity of protein kinases, such as CDK1, CDK2, CDK4, CDK5, CDK6, CDK7, CDK8 and CDK9, using the compounds provided herein.

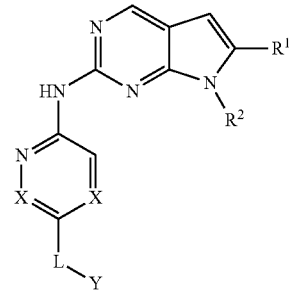

23 Claims, No Drawings

(56) References Cited

FOREIGN PATENT DOCUMENTS

| | | | |
|---|---|---|---|
| WO | 2007071393 | A2 | 6/2007 |
| WO | 2007104053 | A2 | 9/2007 |
| WO | 2007125405 | A2 | 11/2007 |
| WO | 2007127382 | A1 | 11/2007 |
| WO | 2007140222 | A1 | 12/2007 |
| WO | 2009085185 | A1 | 7/2009 |
| WO | 2009098236 | A | 8/2009 |
| WO | 2010/043865 | A1 | 4/2010 |
| WO | 2011101409 | A1 | 8/2011 |
| WO | 2011101417 | A1 | 8/2011 |
| WO | 2011130232 | A1 | 10/2011 |

OTHER PUBLICATIONS

Koretskaya, Khimiko-Farmatsevticheskii Zhurnal, 1968, 6, pp. 5-12.
Siddiqi, J. Med. Chem., 1995, 38, pp. 1174-1188.
Gaulon, Synthesis, 2005, vol. 13, pp. 2227-2233.
Choi, Bioorganic & Med Chem Ltrs, 2006, vol. 16, No. 8, pp. 2173-2176.
Moriarty, Bioorganic & Med Chem Ltrs, 2006, vol. 16, No. 22, pp. 5778-5783.
Choi, Biorganic & Med Chem Ltrs, 2006, 16, pp. 2689-2692.
Fry, Molecular Cancer Therapeutics, 2004, 3(11), pp. 1427-1438.
Baker, Stacey J. et al. "CDK4: A Key Player in the Cell Cycle, Development, and Cancer." Genes & Cancer. Sage, Mar. 14, 2013. pp. 658-66. 13 pages.

\* cited by examiner

PYRROLOPYRIMIDINE COMPOUNDS AND THEIR USES

BACKGROUND

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (Hardie, G. and Hanks, S. The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J. 1995, 9, 576-596; Knighton et al., Science 1991, 253, 407-414; Hiles et al., Cell 1992, 70, 419-429; Kunz et al., Cell 1993, 73, 585-596; Garcia-Bustos et al., EMBO J. 1994, 13, 2352-2361).

In general, protein kinases mediate intracellular signaling by affecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor-α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle. Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1—also known as cdc2, and CDK2), cyclin B1-B3 (CDK1) and cyclin D1-D3 (CDK2, CDK4, CDK5, CDK6), cyclin E (CDK2). Each of these complexes is involved in a particular phase of the cell cycle. Not all members of the CDK family are involved exclusively in cell cycle control, however. Thus CDKs 7, 8, and 9 are implicated in the regulation of transcription, and CDK5 plays a role in neuronal and secretory cell function.

The activity of CDKs is regulated post-translationally, by transitory associations with other proteins, and by alterations of their intracellular localization. Tumor development is closely associated with genetic alteration and deregulation of CDKs and their regulators, suggesting that inhibitors of CDKs may be useful anti-cancer therapeutics. Indeed, early results suggest that transformed and normal cells differ in their requirement for, e.g., cyclin A/CDK2 and that it may be possible to develop novel antineoplastic agents devoid of the general host toxicity observed with conventional cytotoxic and cytostatic drugs. While inhibition of cell cycle-related CDKs is clearly relevant in, e.g., oncology applications, this may not be the case for the inhibition of RNA polymerase-regulating CDKs. On the other hand, inhibition of CDK9/cyclin T function was recently linked to prevention of HIV replication and the discovery of new CDK biology thus continues to open up new therapeutic indications for CDK inhibitors (Sausville, E. A. Trends Molec. Med. 2002, 8, S32-S37).

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. Fischer, P. M. Curr. Opin. Drug Discovery Dev. 2001, 4, 623-634) have been found to possess anti-proliferative properties by virtue of CDK-specific ATP antagonism.

At a molecular level mediation of cdk/cyclin complex activity requires a series of stimulatory and inhibitory phosphorylation, or dephosphorylation, events. Cdk phosphorylation is performed by a group of cdk activating kinases (CAKs) and/or kinases such as wee1, Myt1 and Mik1. Dephosphorylation is performed by phosphatases such as cdc25(a & c), pp 2a, or KAP. Cdk/cyclin complex activity may be further regulated by two families of endogenous cellular proteinaceous inhibitors: the Kip/Cip family, or the INK family. The INK proteins specifically bind cdk4 and cdk6. p16$^{ink4}$ (also known as MTS1) is a potential tumour suppressor gene that is mutated, or deleted, in a large number of primary cancers. The Kip/Cip family contains proteins such as p21$^{Cip1,Waf1}$, p27$^{Kip1}$ and p57$^{kip2}$. As discussed previously p21 is induced by p53 and is able to inactivate the cdk2/cyclin(E/A) and cdk4/cyclin(D1/D2/D3) complexes. Atypically low levels of p27 expression have been observed in breast, colon and prostate cancers. Conversely over expression of cyclin E in solid tumours has been shown to correlate with poor patient prognosis. Over expression of cyclin D1 has been associated with oesophageal, breast, squamous, and non-small cell lung carcinomas.

The pivotal roles of cdks, and their associated proteins, in co-ordinating and driving the cell cycle in proliferating cells have been outlined above. Some of the biochemical pathways in which cdks play a key role have also been described. The development of monotherapies for the treatment of proliferative disorders, such as cancers, using therapeutics targeted generically at cdks, or at specific cdks, is therefore potentially highly desirable. Cdk inhibitors could conceivably also be used to treat other conditions such as viral infections, autoimmune diseases and neuro-degenerative diseases, amongst others. Cdk targeted therapeutics may also provide clinical benefits in the treatment of the previously described diseases when used in combination therapy with either existing, or new, therapeutic agents. Cdk targeted anticancer therapies could potentially have advantages over many current antitumour agents as they would not directly interact with DNA and should therefore reduce the risk of secondary tumour development. Thus, there is a continued need to find new therapeutic agents to treat human diseases. Accordingly, there is a great need to develop inhibitors of protein kinases, such as CDK1, CDK2, CDK4, CDK5, CDK6, CDK7, CDK8 and CDK9.

SUMMARY OF THE INVENTION

There remains a need for new treatments and therapies for protein kinase-associated disorders. There is also a need for compounds useful in the treatment or prevention or amelioration of one or more symptoms of cancer, transplant rejections, and autoimmune diseases. Furthermore, there is a need for methods for modulating the activity of protein kinases, such as CDK1, CDK2, CDK4, CDK5, CDK6, CDK7, CDK8 and CDK9, using the compounds provided herein. In one aspect, the invention provides a compound of Formula I:

In an embodiment, the present invention includes a compound of formula I:

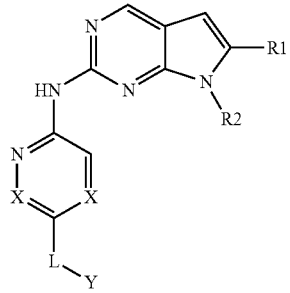

I or pharmaceutically acceptable salts, wherein

X is $CR^9$, or N;

$R^1$ is $C_{1-8}$alkyl, CN, $C(O)OR^4$ or $CONR^5R^6$, a 5-14 membered heteroaryl group, or a 3-14 membered cycloheteroalkyl group;

$R^2$ is $C_{1-8}$alkyl, $C_{3-14}$cycloalkyl, or a 5-14 membered heteroaryl group, and wherein $R^2$ may be substituted with one or more $C_{1-8}$alkyl, or OH;

L is a bond, $C_{1-8}$alkylene, C(O), or $C(O)NR^{10}$, and wherein L may be substituted or unsubstituted;

Y is H, $R^{11}$, $NR^{12}R^{13}$, OH, or Y is part of the following group

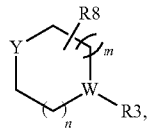

where Y is $CR^9$ or N; where 0-3 $R^8$ may be present, and $R^8$ is $C_{1-8}$alkyl, oxo, halogen, or two or more $R^8$ may form a bridged alkyl group;

W is $CR^9$, or N, or O (where W is O, R3 is absent);

$R^3$ is H, $C_{1-8}$alkyl, $C_{1-8}$alkyl$R^{14}$, $C_{3-44}$cycloalkyl, $C(O)C_{1-8}$ alkyl, $C_{1-8}$haloalkyl, $C_{1-8}$alkylOH, $C(O)NR^{14}R^{15}$, $C_{1-8}$cyanoalkyl, $C(O)R^{14}$, $C_{0-8}$alkylC(O)$C_{0-8}$alkylNR$^{14}R^{15}$, $C_{0-8}$alkylC(O)OR$^{14}$, NR$^{14}R^{15}$, SO$_2C_{1-8}$alkyl, $C_{1-8}$alkyl$C_{3-14}$cycloalkyl, $C(O)C_{1-8}$alkyl$C_{3-14}$cycloalkyl, $C_{1-8}$alkoxy, or OH which may be substituted or unsubstituted when $R^3$ is not H.

$R^9$ is H or halogen;

$R^4$, $R^5$, $R^6$, $R^7$, $R^{10}$, $R^{11}$, $R^{12}$, $R^{13}$, $R^{14}$ and $R^{15}$ are each independently selected from H, $C_{1-6}$alkyl, $C_{3-14}$cycloalkyl, a 3-14 membered cycloheteroalkyl group, a $C_{6-14}$ aryl group, a 5-14 membered heteroaryl group, alkoxy, C(O)H, C(N)OH, $C(N)OCH_3$, $C(O)C_{1-3}$alkyl, $C_{1-8}$alkylNH$_2$, $C_{1-6}$ alkylOH, and wherein $R^4$, $R^5$, $R^6$, $R^7$, $R^{10}$, $R^{11}$, $R^{12}$, and $R^{13}$, $R^{14}$, and $R^{15}$ when not H may be substituted or unsubstituted;

m and n are independently 0-2; and wherein L, $R^3$, $R^4$, $R^5$, $R^6$, $R^7$, $R^{10}$, $R^{12}$, and $R^{13}$, $R^{14}$, and $R^{15}$ may be substituted with one or more of $C_{1-8}$alkyl, $C_{2-8}$alkenyl, $C_{2-8}$alkynyl, $C_{3-14}$cycloalkyl, 5-14 membered heteroaryl group, $C_{6-14}$aryl group, a 3-14 membered cycloheteroalkyl group, OH, (O), CN, alkoxy, halogen, or NH$_2$.

DETAILED DESCRIPTION OF THE INVENTION

In an embodiment, the present invention includes compounds of formula I wherein Y is H, OH, or Y is part of the following group

where Y is N and W is $CR^9$, or N; and where 0-2 $R^8$ may be present, and $R^8$ is $C_{1-8}$alkyl, oxo, or two or more $R^8$ may form a bridged alkyl group. In an embodiment, Y is N and W is N. In an embodiment, m is 1 or 2. In another embodiment, n is 1 or 2. In an embodiment, m is 1 and n is 2. In another embodiment, m is 2 and n is 1. In a further embodiment, both m and n are 1.

In an embodiment, there are 0-2 $R^8$ present in compounds of formula (I). It is understood that when there are zero $R^8$s, that H is attached to the carbons of the cyclic structure.

In an embodiment, $R^8$ is methyl, ethyl, propyl, butyl, oxo, or two $R^8$ can form a bridged (cycloalkyl) group, such as cyclobutyl, cyclopentyl, or cyclohexyl. In an embodiment, $R^8$ is methyl. In another embodiment no $R^8$ is present.

In an embodiment, the present invention includes compounds of formula I wherein $R^3$ is H, $C_{1-8}$alkyl, such as methyl, ethyl, propyl, isopropyl, butyl, pentyl, or hexyl; $C_{3-14}$cycloalkyl, such as cyclopropyl, cyclobutyl, cyclopentyl, or cyclohexyl; $C(O)C_{1-8}$ alkyl, such as $C(O)CH_3$, $C(O)CH_2CH_3$, or $C(O)CH_2CH_2CH_3$; $C_{1-8}$alkylOH, such as $CH_2OH$, $CH_2CH_2OH$, $CHOHCH_3$, $CH_2CH_2CH_2OH$, $CHOHCH_2CH_3$, or $CH_2CHOHCH_3$; $C_{1-8}$cyanoalkyl, such as $CH_2CN$, or $CH_2CH_2CN$; $C_{0-8}$alkylC(O)$C_{0-8}$alkylNR$^{14}R^{15}$, such as $CH_2C(O)CH_2NR^{14}R^{15}$; $C_{0-8}$alkylC(O)OR$^{14}$, NR$^{14}R^{15}$, $C_{1-8}$alkyl$C_{3-14}$cycloalkyl, $C(O)C_{1-8}$alkyl$C_{3-14}$cycloalkyl, $C_{1-8}$alkoxy, $C_{1-8}$alkyl$R^{14}$, $C_{1-8}$ haloalkyl, or $C(O)R^{14}$, which may be substituted with one or more of OH, CN, F, or NH$_2$, and wherein $R^{14}$ and $R^{15}$ are each independently selected from H, $C_{1-8}$alkyl, $C_{3-14}$cycloalkyl, alkoxy, $C(O)C_{1-3}$alkyl, $C_{1-8}$alkylNH$_2$, or $C_{1-6}$alkylOH.

In an embodiment, $R^{14}$, and $R^{15}$ are each independently selected from H, $C_{1-8}$alkyl, such as methyl, ethyl, propyl, butyl, pentyl, or hexyl; $C_{3-14}$ cycloalkyl, such as cyclopropyl, cyclobutyl, cyclopentyl, or cyclohexyl; a 3-14 membered cycloheteroalkyl group, such as morpholine, piperidine, or piperazine; a $C_{6-14}$ aryl group, such as phenyl; a 5-14 membered heteroaryl group, such as pyridine, pyrimidine, or pyridazine; alkoxy, such as methoxy, ethoxy, or propoxy;

C(O)H, C(N)OH, C(N)OCH$_3$, C(O)C$_{1-3}$alkyl, such as C(O) CH$_3$, C(O)CH$_2$CH$_3$, or C(O)CH$_2$CH$_2$CH$_3$; C$_{1-8}$alkylNH$_2$, such as methyleneNH$_2$, ethyleneNH$_2$, or propyleneNH$_2$; C$_{1-6}$ alkylOH, such as methyleneOH, ethyleneOH, or propyleneOH; and R$^{14}$ and R$^{15}$ when not H may be unsubstituted or substituted with one or more of C$_{1-8}$alkyl, C$_{2-8}$alkenyl, C$_{2-8}$alkynyl, C$_{3-14}$cycloalkyl, 5-14 membered heteroaryl group, C$_{6-14}$aryl group, a 3-14 membered cycloheteroalkyl group, OH, (O), CN, alkoxy, halogen, or NH$_2$.

In another embodiment, the present invention includes compound of formula I wherein R$^3$ is H, C$_{1-8}$alkyl, such as methyl, ethyl, propyl, or isopropyl; or C$_{1-8}$alkylOH, such as CH$_2$OH, or CH$_2$CH$_2$OH. In another embodiment, R$^3$ is H, isopropyl, CH$_2$OH, or CH$_2$CH$_2$OH. In another embodiment, R$^3$ is H.

In another embodiment, the present invention includes compounds of formula I wherein L is a bond, C$_{1-8}$alkylene, such as CH$_2$—, —CH$_2$CH$_2$—, or —CH$_2$CH$_2$CH$_2$—; C(O) NH, or C(O).

In another embodiment, the present invention includes compounds of formula I wherein R$^2$ is C$_{3-14}$cycloalkyl; such as cyclopropyl, cyclobutyl, cyclopentyl, or cyclohexyl.

In another embodiment, the present invention includes compounds of formula I wherein R$^2$ is cyclopentyl.

In another embodiment, the present invention includes compounds of formula I wherein R$^1$ is CN, C(O)OR$^4$, CONR$^5$R$^6$, or a 5-14 membered heteroaryl group.

In another embodiment, the present invention includes compounds of formula I wherein R$^1$ is CONR$^5$R$^6$, and R$^5$ and R$^6$ are C$_{1-8}$alkyl. In another embodiment, R$^1$ is CONR$^5$R$^6$ where R$^5$ and R$^6$ are methyl. In another embodiment, R$^1$ is CN.

In another embodiment, the present invention includes compounds of formula I wherein X is CR$^9$, and R$^9$ is H or halogen, such as Cl, F, Br, or I.

In another embodiment, the present invention includes compounds of formula I wherein one X is N and the other X is CR$^9$. In an embodiment, the present invention includes compounds of formula (I), such as:

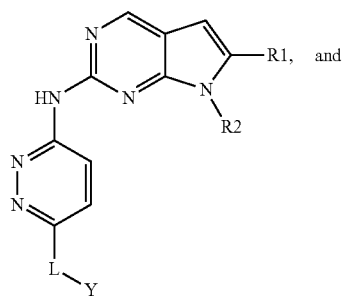

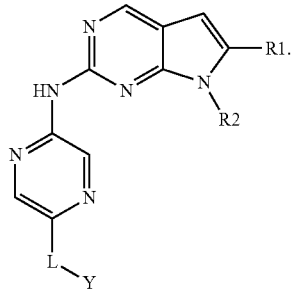

In another embodiment, the present invention includes compounds of formula I wherein X is CR$^9$ and Y is

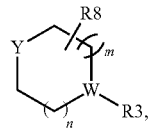

where m and n are 1, and Y and W are N.

In one embodiment the compound is a compound of formula I wherein L is a bond, C$_{1-8}$alkylene, or C(O)NH, or C(O); and Y is H, OH, or Y is part of the following group

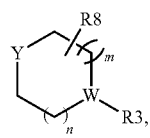

where Y is N and W is CR$^9$, or N; where 0-2 R$^8$ may be present, and R$^8$ is C$_{1-8}$alkyl, oxo, or two or more R$^8$ may link to form a bridged alkyl group and R$^3$ is H, C$_{1-8}$alkyl, C$_{1-8}$alkylR$^{14}$, C$_{1-8}$haloalkyl, C(O)C$_{1-8}$ alkyl, C$_{0-8}$alkylOH, C(O)R$^{14}$, or C$_{0-8}$alkylC(O)CO$_{1-8}$alkylNR$^{14}$R$^{15}$, C$_{0-8}$alkylC(O)OR$^{14}$, or NR$^{14}$R$^{15}$; and R$^{14}$ and R$^{15}$ are each independently selected from H, C$_{3-14}$ cycloalkyl, alkoxy, C(O)C$_{1-3}$alkyl, C$_{1-8}$alkylNH$_2$, C$_{1-6}$ alkylOH.

In one embodiment the compound is a compound of formula I wherein R$^3$ is H, C$_{1-8}$alkyl, C$_{3-14}$cycloalkyl, C(O)C$_{1-8}$ alkyl, C$_{0-8}$alkylOH, C$_{1-8}$cyanoalkyl, C$_{0-8}$alkylC(O)C$_{0-8}$ alkylNR$^{14}$R$^{15}$, C$_{0-8}$alkylC(O)OR$^{14}$, NR$^{14}$R$^{15}$, C$_{1-8}$alkyl C$_{3-14}$ cycloalkyl, C(O)C$_{1-8}$alkylC$_{3-14}$cyclo alkyl, C$_{0-8}$alkoxy, which may be substituted with one or more of OH, CN, F, or NH$_2$.

In one embodiment the compound is a compound of formula I wherein R$^3$ is H or C$_{1-8}$alkyl.

In one embodiment the compound is a compound of formula I wherein R$^1$ is C(O)OR$^4$, CONR$^5$R$^6$, or a 5-14 membered heteroaryl group.

In one embodiment, the present invention includes compounds of formula I wherein Y is

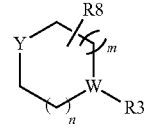

where m and n are 1 or 2, and Y and W are N.

In one embodiment the compound is a compound of formula I wherein L is a bond.

In one embodiment the compound is a compound of formula I wherein L is a bond Y is not H.

In another embodiment, the present invention includes compounds of formula I(a):

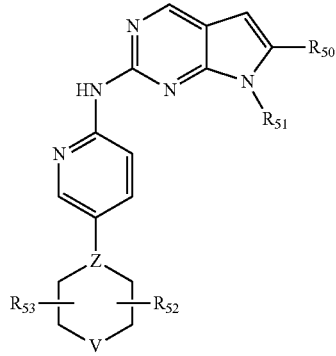

and a pharmaceutically acceptable salt thereof, wherein:

$R^{50}$ is $CONR^{54}R^{55}$, or CN;

$R^{51}$ is $C_{3-14}$cycloalkyl which may be unsubstituted or substituted by $C_{1-3}$alkyl, or OH;

Z is CH or N; and

V is $NR^{56}$ or $CHR^{57}$;

$R^{54}$ and $R^{55}$ are independently H, $C_{1-3}$alkyl, $R^{52}$, $R^{53}R^{56}$, and $R^{57}$ are independently H, $C_{1-8}$alkyl, $C_{3-14}$cycloalkyl, $C_{1-8}$haloalkyl, $NR^{58}R^{59}$, $C(O)OR^{60}$, $C(O)C_{1-8}$alkyl, $C_{0-8}$alkylC(O)$C_{0-8}$alkyl-$NR^{61}R^{62}$, $C_{1-8}$alkoxy, $C_{1-8}$alkylOR$^{63}$, C(O)-5-14cycloheteroalkyl group, $C_{3-14}$cycloalkyl group, each of which when not H may be substituted by one or more of $C_{1-8}$alky, OH, or CN;

$R^{58}$, $R^{59}$, $R^{60}$, $R^{61}$, $R^{62}$, and $R^{63}$ are H or $C_{1-8}$alkyl.

In an embodiment of the present invention, formula I(a) includes compounds where $R^{50}$ is $CONR^{53}R^{55}$, and $R^{54}$ and $R^{55}$ are H, methyl, or ethyl. In another embodiment, $R^{54}$ and $R^{55}$ are both methyl.

In another embodiment, formula I(a) includes compounds where $R^{51}$ is cyclopropyl, cyclobutyl, cyclopentyl, and cyclohexyl. In another embodiment, the invention includes compounds where $R^{51}$ is cyclopentyl.

In another embodiment, formula I(a) includes compounds where Z is N. In another embodiment, the present invention includes compounds where V is $NR^{56}$. In another embodiment, the present invention includes compounds where V is $NR^{56}$, and $R^{56}$ is H, methyl, ethyl, propyl which may be substituted by OH. In another embodiment, $R^{56}$ is isopropyl. In another embodiment, $R^{56}$ is H. In yet another embodiment, $R^{56}$ is —CH$_2$CH$_2$OH.

In another embodiment, the present invention includes a method of treating a disease, disorder or syndrome associated with CDK 4 inhibition, said method comprising administering a compound according to formula I or I(a) or its prodrug or pharmaceutical composition comprising the compound of formula I or I(a) or its prodrug and pharmaceutically acceptable excipients to a subject in need thereof.

In another embodiment, the present invention includes a method of treating a disease associated with CDK 4 inhibition, wherein the disease, disorder or syndrome is hyperproliferative in a subject, wherein subject is an animal including humans, selected from a group comprising cancer and inflammation.

In another embodiment, the present invention includes a method of inhibiting a cyclin dependent kinase (e.g. cdk-4), which method comprises contacting the kinase with a kinase-inhibiting compound according to formula I or I(a).

In another embodiment, the present invention includes a method of modulating a cellular process (for example cell division) by inhibiting the activity of a cyclin dependent kinase using a compound according to formula I or I(a).

In another embodiment, the present invention includes a compound of formula I or I(a) for use in the prophylaxis or treatment of a disease state as described herein.

In another embodiment, the present invention includes the use of a compound of formula I or I(a) for the manufacture of a medicament, wherein the medicament is for any one or more of the uses defined herein.

In another embodiment, the present invention includes a pharmaceutical composition comprising a compound of formula I or I(a) and a pharmaceutically acceptable carrier.

In another embodiment, the present invention includes a pharmaceutical composition comprising a compound of formula I or I(a) and a pharmaceutically acceptable carrier in a form suitable for oral administration.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present invention.

"Analog" as used herein, refers to a small organic compound, a nucleotide, a protein, or a polypeptide that possesses similar or identical activity or function(s) as the compound, nucleotide, protein or polypeptide or compound having the desired activity and therapeutic effect of the present invention. (e.g., inhibition of tumor growth), but need not necessarily comprise a sequence or structure that is similar or identical to the sequence or structure of the preferred embodiment "Derivative" refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

As used herein, "halo" or "halogen" refers to fluoro, chloro, bromo, and iodo.

As used herein, "alkyl" refers to a straight-chain or branched saturated hydrocarbon group. In some embodiments, an alkyl group can have from 1 to 10 carbon atoms (e.g., from 1 to 8 carbon atoms). Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl), hexyl (e.g., n-hexyl and its isomers), and the like. A lower alkyl group typically has up to 4 carbon atoms. Examples of lower alkyl groups include methyl, ethyl, propyl (e.g., n-propyl and isopropyl), and butyl groups (e.g., n-butyl, isobutyl, s-butyl, t-butyl). In an embodiment an alkyl group, or two or more alkyl groups may form a bridged alkyl group. This is where an alkyl group links across another group (particularly shown in cyclic groups), forming a ring bridged by an alkyl chain, i.e., forming a bridged fused ring. This is shown, but not limited to where two or more $R^8$ groups for a bridged alkyl group across the Y ring group forming a ring bridged by an alkyl chain.

As used herein, "alkenyl" refers to a straight-chain or branched alkyl group having one or more carbon-carbon double bonds. In some embodiments, an alkenyl group can have from 2 to 10 carbon atoms (e.g., from 2 to 8 carbon atoms). Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene).

As used herein, "alkynyl" refers to a straight-chain or branched alkyl group having one or more carbon-carbon triple bonds. In some embodiments, an alkynyl group can have from 2 to 10 carbon atoms (e.g., from 2 to 8 carbon atoms). Examples of alkynyl groups include ethynyl, propynyl, butynyl, pentynyl, and the like. The one or more carbon-carbon triple bonds can be internal (such as in 2-butyne) or terminal (such as in 1-butyne).

As used herein, "alkoxy" refers to an —O-alkyl group. Examples of alkoxy groups include methoxy, ethoxy, propoxy (e.g., n-propoxy and isopropoxy), t-butoxy groups, and the like. As used herein, "alkylthio" refers to an —S-alkyl group. Examples of alkylthio groups include methylthio, ethylthio, propylthio (e.g., n-propylthio and isopropylthio), t-butylthio groups, and the like.

The term "carbalkoxy" refers to an alkoxycarbonyl group, where the attachment to the main chain is through the carbonyl group (C(O)). Examples include but are not limited to methoxy carbonyl, ethoxy carbonyl, and the like.

As used herein, "oxo" refers to a double-bonded oxygen (i.e., =O). It is also to be understood that the terminology C(O) refers to a —C=O group, whether it be ketone, aldehyde or acid or acid derivative. Similarly, S(O) refers to a —S=O group.

As used herein, "haloalkyl" refers to an alkyl group having one or more halogen substituents. In some embodiments, a haloalkyl group can have 1 to 10 carbon atoms (e.g., from 1 to 8 carbon atoms). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-10}$ haloalkyl group can have the formula $C_iH_{2i+1-j}X_j$, wherein X is F, Cl, Br, or I, i is an integer in the range of 1 to 10, and j is an integer in the range of 0 to 21, provided that j is less than or equal to 2i+1.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. A cycloalkyl group, as a whole, can have from 3 to 14 ring atoms (e.g., from 3 to 8 carbon atoms for a monocyclic cycloalkyl group and from 7 to 14 carbon atoms for a polycyclic cycloalkyl group). Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like.

As used herein, "heteroatom" refers to an atom of any element other than carbon or hydrogen and includes, for example, nitrogen, oxygen, sulfur, phosphorus, and selenium.

As used herein, "cycloheteroalkyl" refers to a non-aromatic cycloalkyl group that contains at least one (e.g., one, two, three, four, or five) ring heteroatom selected from O, N, and S, and optionally contains one or more (e.g., one, two, or three) double or triple bonds. A cycloheteroalkyl group, as a whole, can have from 3 to 14 ring atoms and contains from 1 to 5 ring heteroatoms (e.g., from 3-6 ring atoms for a monocyclic cycloheteroalkyl group and from 7 to 14 ring atoms for a polycyclic cycloheteroalkyl group). The cycloheteroalkyl group can be covalently attached to the defined chemical structure at any heteroatom(s) or carbon atom(s) that results in a stable structure. One or more N or S atoms in a cycloheteroalkyl ring may be oxidized (e.g., morpholine N-oxide, thiomorpholine S-oxide, thiomorpholine S,S-dioxide). Cycloheteroalkyl groups can also contain one or more oxo groups, such as phthalimidyl, piperidonyl, oxazolidinonyl, 2,4(1H,3H)-dioxo-pyrimidinyl, pyridin-2(1H)-onyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothienyl, piperidinyl, piperazinyl, azetidine, and the like.

As used herein, "aryl" refers to an aromatic monocyclic hydrocarbon ring system or a polycyclic ring system where at least one of the rings in the ring system is an aromatic hydrocarbon ring and any other aromatic rings in the ring system include only hydrocarbons. In some embodiments, a monocyclic aryl group can have from 6 to 14 carbon atoms and a polycyclic aryl group can have from 8 to 14 carbon atoms. The aryl group can be covalently attached to the defined chemical structure at any carbon atom(s) that result in a stable structure. In some embodiments, an aryl group can have only aromatic carbocyclic rings, e.g., phenyl, 1-naphthyl, 2-naphthyl, anthracenyl, phenanthrenyl groups, and the like. In other embodiments, an aryl group can be a polycyclic ring system in which at least one aromatic carbocyclic ring is fused (i.e., having a bond in common with) to one or more cycloalkyl or cycloheteroalkyl rings. Examples of such aryl groups include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like.

As used herein, "heteroaryl" refers to an aromatic monocyclic ring system containing at least one ring heteroatom selected from O, N, and S or a polycyclic ring system where at least one of the rings in the ring system is aromatic and contains at least one ring heteroatom. A heteroaryl group, as a whole, can have from 5 to 14 ring atoms and contain 1-5 ring heteroatoms. In some embodiments, heteroaryl groups can include monocyclic heteroaryl rings fused to one or more aromatic carbocyclic rings, non-aromatic carbocyclic rings, or non-aromatic cycloheteroalkyl rings. The heteroaryl group can be covalently attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like.

The term "lower alkenyl" refers to a alkenyl group which contains 2-6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include but are not limited to ethenyl, 1-propenyl, 2-propenyl, 1-butenyl, 2-butenyl, 2-methyl-1-propenyl, 1,3-butadienyl, and the like.

The term "lower alkynyl", as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. In an embodiment, the alkynyl group contains 1 or 2 carbon-carbon triple bonds and more preferably one carbon-carbon triple bond. The alkynyl group may be straight chained or branched. Examples include but are not limited to ethynyl, 1-propynyl, 2-propynyl, 1-butynyl, 2-butynyl and the like.

The present invention includes all pharmaceutically acceptable isotopically-labeled compounds of the invention, i.e. compounds of formula (I) or I(a), wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I) or I(a), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and N, can be useful in Positron Emission Topography (PET) studies for examining substrate receptor occupancy.

Isotopically-labeled compounds of formula (I) or I(a) can generally be prepared by conventional techniques known to those skilled in the art or by processes analogous to those described in the accompanying Examples and Preparations using an appropriate isotopically-labeled reagents in place of the non-labeled reagent previously employed.

Biological Activity

The compounds of the formulae (I) or I(a) and sub-groups thereof are inhibitors of cyclin dependent kinases. For example, compounds of the invention are inhibitors of cyclin dependent kinases, and in particular cyclin dependent kinases selected from CDK1, CDK2, CDK3, CDK4, CDK5, CDK6 and CDK9, and more particularly selected from CDK1, CDK2, CDK3, CDK4, CDK5 and CDK9.

Compounds of the invention also have activity against glycogen synthase kinase-3 (GSK-3). As a consequence of their activity in modulating or inhibiting CDK and glycogen synthase kinase, they are expected to be useful in providing a means of arresting, or recovering control of, the cell cycle in abnormally dividing cells. It is therefore anticipated that the compounds will prove useful in treating or preventing proliferative disorders such as cancers. It is also envisaged that the compounds of the invention will be useful in treating conditions such as viral infections, type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions where it is envisaged that the compounds of the invention will be useful consists of viral infections, autoimmune diseases and neurodegenerative diseases.

CDKs play a role in the regulation of the cell cycle, apoptosis, transcription, differentiation and CNS function. Therefore, CDK inhibitors could be useful in the treatment of diseases in which there is a disorder of proliferation, apoptosis or differentiation such as cancer. In particular RB+ve tumours may be particularly sensitive to CDK inhibitors. These include tumours harbouring mutations in ras, Raf, Growth Factor Receptors or over-expression of Growth Factor Receptors. Furthermore tumours with hypermethylated promoter regions of CDK inhibitors as well as tumours overexpressing cyclin partners of the cyclin dependent kinases may also display sensitivity. RB-ve tumours may also be sensitive to CDK inhibitors.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, nose, head and neck, prostate, or skin, for example squamous cell carcinoma; a hematopoietic tumour of lymphoid lineage, for example leukemia, acute lymphocytic leukemia, chronic lymphocytic leukaemia, B-cell lymphoma (such as diffuse large B cell lymphoma), T-cell lymphoma, multiple myeloma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers may be cancers which are sensitive to inhibition of any one or more cyclin dependent kinases selected from CDK1, CDK2, CDK3, CDK4, CDK5 and CDK6, for example, one or more CDK kinases selected from CDK1, CDK2, CDK4 and CDK5, e.g. CDK1 and/or CDK2. Whether or not a particular cancer is one which is sensitive to inhibition by a cyclin dependent kinase inhibitor may be determined by means of a cell growth assay as set out in the examples below or by a method as set out in the section headed "Methods of Diagnosis".

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases, ophthalmic diseases including age related macular degeneration, uveitis, and cancer pain.

It has also been discovered that some cyclin-dependent kinase inhibitors can be used in combination with other anticancer agents. For example, the cyclin-dependent kinase inhibitor flavopiridol has been used with other anticancer agents in combination therapy. Thus, in the pharmaceutical compositions, uses or methods of this invention for treating a disease or condition comprising abnormal cell growth, the disease or condition comprising abnormal cell growth in one embodiment is a cancer.

One group of cancers includes human breast cancers (e.g. primary breast tumours, node-negative breast cancer, invasive duct adenocarcinomas of the breast, non-endometrioid breast cancers); and mantle cell lymphomas. In addition, other cancers are colorectal and endometrial cancers.

Another sub-set of cancers includes hematopoietic tumours of lymphoid lineage, for example leukemia, chronic lymphocytic leukaemia, mantle cell lymphoma and B-cell lymphoma (such as diffuse large B cell lymphoma).

One particular cancer is chronic lymphocytic leukaemia.
Another particular cancer is mantle cell lymphoma.
Another particular cancer is diffuse large B cell lymphoma
Another sub-set of cancers includes breast cancer, ovarian cancer, colon cancer, prostate cancer, oesophageal cancer, squamous cancer and non-small cell lung carcinomas.

Another sub-set of cancers includes breast cancer, pancreatic cancer, colorectal cancer, lung cancer, and melanoma.

A further sub-set of cancers, namely cancers wherein compounds having CDK4 inhibitory activity may be of particular therapeutic benefit, comprises retinoblastomas, small cell lung carcinomas, non-small lung carcinomas, sarcomas, gliomas, pancreatic cancers, head, neck and breast cancers and mantle cell lymphomas.

Another sub-set of cancers wherein compounds having CDK4 inhibitory activity may be of particular therapeutic benefit comprises small cell lung cancer, non-small cell lung cancer, pancreatic cancer, breast cancer, glioblastoma multiforme, T cell ALL and mantle cell lymphoma. A further subset of cancers which the compounds of the invention may be useful in the treatment of includes sarcomas, leukemias, glioma, familial melanoma and melanoma.

Methods of Diagnosis

Prior to administration of a compound of the formula (I) or I(a), a patient may be screened to determine whether a disease or condition from which the patient is or may be suffering is one which would be susceptible to treatment with a compound having activity against cyclin dependent kinases. For example, a biological sample taken from a patient may be analysed to determine whether a condition or disease, such as cancer, that the patient is or may be suffering from is one which is characterised by a genetic abnormality or abnormal protein expression which leads to over-activation of CDKs or to sensitisation of a pathway to normal CDK activity. Examples of such abnormalities that result in activation or sensitisation of the CDK2 signal include up-regulation of cyclin E, (Harwell R M, Mull B B, Porter D C, Keyomarsi K.; J Biol. Chem. 2004 Mar. 26; 279(13):12695-705) or loss of p21 or p27, or presence of CDC4 variants (Rajagopalan H, Jallepalli P V, Rago C, Velculescu V E, Kinzler K W, Vogelstein B, Lengauer C.; Nature. 2004 Mar. 4; 428(6978):77-81). Tumours with mutants of CDC4 or up-regulation, in particular over-expression, of cyclin E or loss of p21 or p27 may be particularly sensitive to CDK inhibitors. The term up-regulation includes elevated expression or over-expression, including gene amplification (i.e. multiple gene copies) and increased expression by a transcriptional effect, and hyperactivity and activation, including activation by mutations.

Thus, the patient may be subjected to a diagnostic test to detect a marker characteristic of up-regulation of cyclin E, or loss of p21 or p27, or presence of CDC4 variants. The term diagnosis includes screening. By marker we include genetic markers including, for example, the measurement of DNA composition to identify mutations of CDC4. The term marker also includes markers which are characteristic of up regulation of cyclin E, including enzyme activity, enzyme levels, enzyme state (e.g. phosphorylated or not) and mRNA levels of the aforementioned proteins. Tumours with upregulation of cyclin E, or loss of p21 or p27 may be particularly sensitive to CDK inhibitors. Tumours may preferentially be screened for upregulation of cyclin E, or loss of p21 or p27 prior to treatment. Thus, the patient may be subjected to a diagnostic test to detect a marker characteristic of up-regulation of cyclin E, or loss of p21 or p27.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found, Rajagopalan et al (Nature. 2004 Mar. 4; 428(6978):77-81), that there were mutations present in CDC4 (also known as Fbw7 or Archipelago) in human colorectal cancers and endometrial cancers (Spruck et al, Cancer Res. 2002 Aug. 15; 62(16):4535-9). Identification of individual carrying a mutation in CDC4 may mean that the patient would be particularly suitable for treatment with a CDK inhibitor. Tumours may preferentially be screened for presence of a CDC4 variant prior to treatment. The screening process will typically involve direct sequencing, oligonucleotide microarray analysis, or a mutant specific antibody.

Methods of identification and analysis of mutations and up-regulation of proteins are well known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649). Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin E, or loss of p21 or p27, or detection of CDC4 variants could be applicable in the present case.

Therefore, all of these techniques could also be used to identify tumours particularly suitable for treatment with the compounds of the invention.

Tumours with mutants of CDC4 or up-regulation, in particular over-expression, of cyclin E or loss of p21 or p27 may be particularly sensitive to CDK inhibitors. Tumours may preferentially be screened for up-regulation, in particular over-expression, of cyclin E (Harwell R M, Mull B B, Porter D C, Keyomarsi K.; J Biol. Chem. 2004 Mar. 26; 279(13): 12695-705) or loss of p21 or p27 or for CDC4 variants prior to treatment (Rajagopalan H, Jallepalli P V, Rago C, Velculescu V E, Kinzler K W, Vogelstein B, Lengauer C.; Nature. 2004 Mar. 4; 428(6978):77-81). Patients with mantle cell lymphoma (MCL) could be selected for treatment with a compound of the invention using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11;14)(q13;q32) translocation. Over-expression of cyclin D1 mRNA, found in mantle cell lymphoma (MCL), is a critical diagnostic marker. Yatabe et al (Blood. 2000 Apr. 1; 95(7):2253-61) proposed that cyclin D1-positivity should be included as one of the standard criteria for MCL, and that innovative therapies for this incurable disease should be explored on the basis of the new criteria. Jones et al (J Mol. Diagn. 2004 May; 6(2):84-9) developed a real-time, quantitative, reverse transcription PCR assay for cyclin D1 (CCND1) expression to aid in the diagnosis of mantle cell lymphoma (MCL). Howe et al (Clin Chem. 2004 January; 50(1):80-7) used real-time quantitative RT-PCR to evaluate cyclin D1 mRNA expression and found that quantitative RT-PCR for cyclin D1 mRNA normalized to CD19 mRNA can be used in the diagnosis of MCL in blood, marrow, and tissue. Alternatively, patients with breast cancer could be selected for treatment with a CDK inhibitor using diagnostic tests outline above. Tumour cells commonly overexpress cyclin E and it has been shown that cyclin E is over-expressed in breast cancer (Harwell et al, Cancer Res, 2000, 60, 481-489). Therefore breast cancer may in particular be treated with a CDK inhibitor as provided herein.

In addition, the cancer may be analysed for INK4a and RB loss of function, and cyclin D1 or CDK4 overexpression or CDK4 mutation. RB loss and mutations inactivating $p16^{INK4a}$ function or hypermethylation of $p16^{INK4a}$ occur in many tumour types. Rb is inactivated in 100% retinoblastomas and in 90% of small cell lung carcinomas. Cyclin D1 is amplified in 40% of head and neck, over-expressed in 50% of breast cancers and 90% of mantle cell lymphomas. p16 is deleted in 60% of non-small lung carcinomas and in 40% of pancreatic cancers. CDK4 is amplified in 20% of sarcomas and in 10% of gliomas. Events resulting in RB or $p16^{INK4a}$ inactivation through mutation, deletion, or epigenetic silencing, or in the overexpression of cyclin D1 or Cdk4 can be identified by the techniques outlined herein. Tumours with up-regulation, in particular over-expression of cyclin D or CDK4 or loss of INK4a or RB may be particularly sensitive to CDK inhibitors. Thus, the patient may be subjected to a diagnostic test to detect a marker characteristic of over-expression of cyclin D or CDK4 or loss of INK4a or RB.

Cancers that experience INK4a and RB loss of function and cyclin D1 or CDK4 overexpression, include small cell lung cancer, non-small cell lung cancer, pancreatic cancer, breast cancer, glioblastoma multiforme, T cell ALL and mantle cell lymphoma. Therefore patients with small cell lung cancer, non-small cell lung cancer, pancreatic cancer, breast cancer, glioblastoma multiforme, T cell ALL or mantle cell lymphoma could be selected for treatment with a CDK inhibitor using diagnostic tests outlined above and may in particular be treated with a CDK inhibitor as provided herein.

Patients with specific cancers caused by aberrations in the D-Cyclin-CDK4/6-INK4-Rb pathway could be identified by using the techniques described herein and then treated with a CDK4 inhibitor as provided. Examples of abnormalities that activate or sensitise tumours to CDK4 signal include, receptor activation e.g. Her-2/Neu in breast cancer, ras mutations for example in pancreatic, colorectal or lung cancer, raf mutations for example in melanoma, p16 mutations for example in melanoma, p16 deletions for example in lung cancer, p16 methylation for example in lung cancer or cyclin D overexpression for example in breast cancer. Thus, a patient could be selected for treatment with a compound of the invention using diagnostic tests as outlined herein to identify up-regulation of the D-Cyclin-CDK4/6-INK4-Rb pathway for example by overexpression of cyclin D, mutation of CDK4, mutation or depletion of pRb, deletion of p16-INK4, mutation, deletion or methylation of p16, or by activating events upstream of the CDK4/6 kinase e.g. Ras mutations or Raf mutations or hyperactive or over-expressed receptors such as Her-2/Neu.

The compounds of the present invention are particularly advantageous in that they are selective inhibitors of CDK4 over other cyclin dependent kinases. PCT/US2007/069595 generically discloses compounds of this class, but the presently claimed compounds have increased potency and selectivity of CDK4 over other cyclin dependent kinases. This is advantageous in developing a drug suitable for use as a CDK4 inhibitor.

More particularly and with regard to the generic application, the following compounds (from PCT/US2007/069595) of table 3 represent the closest prior art to the chemotype of the presently claimed invention:

TABLE 3

(Prior Art)

| Compound | Example Number |
|---|---|
| 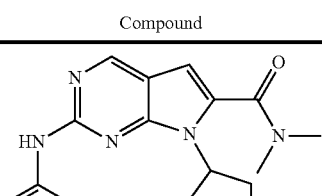 | 200 |

TABLE 3-continued (Prior Art)

| Compound | Example Number |
|---|---|
|  | 201 |
|  | 202 |

The following table 4 shows the inhibition against relevant targets of compounds of the prior art as compared to compounds of the present invention:

TABLE 4

| Compound Number | IC50 (μM) | Selectivity |
|---|---|---|
| 200 (prior art) | CDK4: 0.005<br>CDK1: >1.6<br>CDK2: >1.4 |  |
| 201 (prior art) | CDK4: 0.11<br>CDK1: 7.5<br>CDK2: 10.3 |  |
| 202 (prior art) | CDK4: 2.5<br>CDK1: >15<br>CDK2: >15 |  |
| 74 of present application | CDK4: 0.01<br>CDK1: 113<br>CDK2: 76 | Greater than 11,000 fold selective against CDK4 |
| 63 of present application | CDK4: 0.008<br>CDK1: >15<br>CDK2: >15 |  |
| 26 of present application | CDK4: 0.026<br>CDK1: >15<br>CDK2: >15 |  |

The superior selectivity of the presently claimed compounds against other CDK family members and other kinases means that, compared to other compounds with less selectivity, the presently claimed compounds would have reduced off target activities, and therefore less unpredicted toxicity in cells. When looking at the results of cell cycle analysis performed with the presently claimed compounds and compound 200 of the prior art, for example, it is clear that, while the presently claimed compounds maintain exclusive G1 arrest even at 10 uM concentrations, compound 200 starts to induce G2/M phase blocks at 1 and 10 uM concentrations, reflecting its off-target activities at higher than 1 uM concentrations. Moreover, the inhibitory effects of the CDK4 inhibitor are absolutely dependent upon the presence of the Retinoblastoma protein (pRb). Activities in pRb negative cells for candidate CDK4 inhibitors indicate that the compounds have off-target activities and not as selective. Compared to the presently claimed series, which are inert in pRb negative cells, compound 200 does inhibit the cell proliferation of pRb negative cells at high concentrations, illustrating its off target activities.

Still further, it has been shown that, while the activity of CDK4 is not required for normal fibroblast cell proliferation, the inhibition of CDK1 is thought to be an undesirable effect. When dosed to animals, compared to the prior art, the presently claimed compounds are expected to induce less cytotoxicity. Therefore, the presently claimed compounds are a superior CDK4 inhibitor compared to those of the same scaffolds with the same K4 potency but less selectivity against other CDKs/kinases, as the compound should have a higher therapeutic index than the less selective ones.

In an other embodiment, the present invention comprises the following compounds:

7-Cyclopentyl-2-[5-(3-methyl-piperazin-1-yl)-pyridin-2-ylamino]-7H-pyrrolo[2,3d]pyrimidine-6-carbonitrile;

7-Cyclopentyl-2-{5-[4-(2-fluoro-ethyl)-piperazin-1-yl]-pyridin-2-ylamino}-7H-pyrrolo[2,3-d]pyrimidine-6-carboxylic acid dimethylamide;

7-Cyclopentyl-2-(4-dimethylamino-3,4,5,6-tetrahydro-2H-[1,3']bipyridinyl-6'-ylamino)-7H-pyrrolo[2,3-d]pyrimidine-6-carboxylic acid dimethylamide;

2-[5-(4-Carbamoylmethyl-piperazin-1-yl)-pyridin-2-ylamino]-7-cyclopentyl-7H-pyrrolo[2,3-d]pyrimidine-6-carboxylic acid dimethylamide;

2-{5-[4-(2-Amino-acetyl)-piperazin-1-yl]-pyridin-2-ylamino}-7-cyclopentyl-7H-pyrrolo[2,3-d]pyrimidine-6-carboxylic acid dimethylamide;

2-[5-(3-Amino-pyrrolidin-1-yl)-pyridin-2-ylamino]-7-cyclopentyl-7H-pyrrolo[2,3-d]pyrimidine-6-carboxylic acid dimethylamide;

7-Cyclopentyl-2-{5-[4-(2-methoxy-ethyl)-piperazin-1-yl]-pyridin-2-ylamino}-7H-pyrrolo[2,3-d]pyrimidine-6-carboxylic acid dimethylamide;

7-Cyclopentyl-2-[4-(2-hydroxyethyl)-3,4,5,6-tetrahydro-2H-[1,2']bipyrazinyl-5'-ylamino]-7H-pyrrolo[2,3-d]pyrimidine-6-carboxylic acid dimethylamide;

7-Cyclopentyl-2-[5-((R)-3-methyl-piperazin-1-yl)-pyridin-2-ylamino]-7H-pyrrolo[2,3-d]pyrimidine-6-carboxylic acid dimethylamide;

7-Cyclopentyl-2-[5-((S)-3-methylpiperazin-1-yl)-pyridin-2-ylamino]-7H-pyrrolo[2,3-d]pyrimidine-6-carboxylic acid dimethylamide;

7-Cyclopentyl-2-[5-(3-methylpiperazin-1-yl)-pyridin-2-ylamino]-7H-pyrrolo[2,3-d]pyrimidine-6-carboxylic acid dimethylamide;

7-Cyclopentyl-2-{5-[4-(3-hydroxypropyl)-piperazin-1-yl]-pyridin-2-ylamino}-7H-pyrrolo[2,3-d]pyrimidine-6-carboxylic acid dimethylamide;

7-Cyclopentyl-2-{5-[4-(pyrrolidine-1-carbonyl)-piperazin-1-yl]-pyridin-2-ylamino}-7H-pyrrolo[2,3-d]pyrimidine-6-carboxylic acid dimethylamide;

7-Cyclopentyl-2-{5-[4-(2-hydroxy-ethyl)-piperazin-1-yl]-pyridin-2-ylamino}-7H-pyrrolo[2,3-d]pyrimidine-6-carboxylic acid dimethylamide;

7-Cyclopentyl-2-{5-[4-((S)-2,3-dihydroxypropyl)-piperazin-1-yl]-pyridin-2-ylamino}-7H-pyrrolo[2,3-d]pyrimidine-6-carboxylic acid dimethylamide;

7-Cyclopentyl-2-(5-{4-[2-(2-hydroxyethoxy)-ethyl]-piperazin-1-yl}-pyridin-2-ylamino)-7H-pyrrolo[2,3-d]pyrimidine-6-carboxylic acid dimethylamide;

7-Cyclopentyl-2-{5-[4-(2-hydroxy-1-methylethyl)-piperazin-1-yl]-pyridin-2-ylamino}-7H-pyrrolo[2,3-d]pyrimidine-6-carboxylic acid dimethylamide;

7-Cyclopentyl-2-{6-[4-(2-hydroxyethyl)-piperazin-1-yl]-pyridazin-3-ylamino}-7H-pyrrolo[2,3-d]pyrimidine-6-carboxylic acid dimethylamide;

7-Cyclopentyl-2-{5-[4-(2,3-dihydroxypropyl)-piperazin-1-yl]-pyridin-2-ylamino}-7H-pyrrolo[2,3-d]pyrimidine-6-carboxylic acid dimethylamide;

7-Cyclopentyl-2-{5-[4-((R)-2,3-dihydroxypropyl)-piperazin-1-yl]-pyridin-2-ylamino}-7H-pyrrolo[2,3-d]pyrimidine-6-carboxylic acid dimethylamide;

7-Cyclopentyl-2-(4-dimethylamino-3,4,5,6-tetrahydro-2H-[1,3']bipyridinyl-6'-ylamino)-7H-pyrrolo[2,3-d]pyrimidine-6-carbonitrile;

7-Cyclopentyl-2-(3,4,5,6-tetrahydro-2H-[1,2']bipyrazinyl-5'-ylamino)-7H-pyrrolo[2,3-d]pyrimidine-6-carboxylic acid dimethylamide;

7-Cyclopentyl-2-[5-(piperazine-1-carbonyl)-pyridin-2-ylamino]-7H-pyrrolo[2,3d]pyrimidine-6-carboxylic acid dimethylamide;

7-Cyclopentyl-2-[5-(4-dimethylaminopiperidine-1-carbonyl)-pyridin-2-ylamino]-7H-pyrrolo[2,3-d]pyrimidine-6-carboxylic acid dimethylamide;

7-Cyclopentyl-2-(1',2',3',4',5',6'-hexahydro-[3,4']bipyridinyl-6-ylamino)-7H-pyrrolo[2,3d]pyrimidine-6-carboxylic acid dimethylamide;

7-Cyclopentyl-2-[5-((S)-3-methylpiperazin-1-ylmethyl)-pyridin-2-ylamino]-7H-pyrrolo[2,3-d]pyrimidine-6-carboxylic acid dimethylamide;

7-Cyclopentyl-2-{5-[4-((S)-2-hydroxypropyl)-piperazin-1-yl]-pyridin-2-ylamino}-7H-pyrrolo[2,3-d]pyrimidine-6-carboxylic acid dimethylamide;

7-Cyclopentyl-2-{5-[4-((R)-2-hydroxypropyl)-piperazin-1-yl]-pyridin-2-ylamino}-7H-pyrrolo[2,3-d]pyrimidine-6-carboxylic acid dimethylamide;

7-Cyclopentyl-2-(5-piperazin-1-yl-pyridin-2-ylamino)-7H-pyrrolo[2,3-d]pyrimidine-6-carboxylic acid methylamide;

7-Cyclopentyl-2-[5-(4-isopropyl-piperazin-1-yl)-pyridin-2-ylamino]-7H-pyrrolo[2,3d]pyrimidine-6-carboxylic acid dimethylamide;

7-Cyclopentyl-2-[5-(4-isopropyl-piperazine-1-carbonyl)-pyridin-2-ylamino]-7H-pyrrolo[2,3-d]pyrimidine-6-carboxylic acid dimethylamide;

7-Cyclopentyl-2-{5-[4-(4-methyl-pentyl)-piperazin-1-yl]-pyridin-2-ylamino}-7H-pyrrolo[2,3-d]pyrimidine-6-carboxylic acid dimethylamide;

7-Cyclopentyl-2-[6-(4-isopropyl-piperazin-1-yl)-pyridazin-3-ylamino]-7H-pyrrolo[2,3-d]pyrimidine-6-carboxylic acid dimethylamide;

7-Cyclopentyl-2-{5-[4-(2-hydroxy-2 methylpropyl)-piperazin-1-yl]-pyridin-2-ylamino}-7H-pyrrolo[2,3-d]pyrimidine-6-carboxylic acid dimethylamide;

7-Cyclopentyl-2-[5-(3,3-dimethyl-piperazin-1-yl)-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]oct-3-ylmethyl)-pyridin-2-ylamino]-7H-pyrrolo[2,3-d]pyrimidine-6-carboxylic acid dimethylamide;

7-Cyclopentyl-2-(5-piperazin-1-yl-pyridin-2-ylamino)-7H-pyrrolo[2,3-d]pyrimidine-6-carboxylic acid dimethylamide;

7-Cyclopentyl-2-[5-(4-ethyl-piperazin-1-yl)-pyridin-2-ylamino]-7H-pyrrolo[2,3-d]pyrimidine-6-carboxylic acid dimethylamide;

7-Cyclopentyl-2-[5-(4-cyclopentyl-piperazin-1-yl)-pyridin-2-ylamino]-7H-pyrrolo[2,3-d]pyrimidine-6-carboxylic acid dimethylamide;

7-Cyclopentyl-2-(1'-isopropyl-1',2',3',4',5',6'-hexahydro-[3,4']bipyridinyl-6-ylamino)-7H-pyrrolo[2,3-d]pyrimidine-6-carboxylic acid dimethylamide;

7-Cyclopentyl-2-{5-[(R)-4-(2-hydroxyethyl)-3-methyl-piperazin-1-yl]-pyridin-2-ylamino}-7H-pyrrolo[2,3-d]pyrimidine-6-carboxylic acid dimethylamide;

7-Cyclopentyl-2-{5-[(S)-4-(2-hydroxyethyl)-3-methyl-piperazin-1-yl]-pyridin-2-ylamino}-7H-pyrrolo[2,3-d]pyrimidine-6-carboxylic acid dimethylamide;

7-Cyclopentyl-2-{5-[4-(2-hydroxyethyl)-piperazin-1-ylmethyl]-pyridin-2-ylamino}-7H-pyrrolo[2,3-d]pyrimidine-6-carboxylic acid dimethylamide;

7-Cyclopentyl-2-{5-[4-(2-dimethylamino acetyl)-piperazin-1-yl]-pyridin-2-ylamino}-7H-pyrrolo[2,3-d]pyrimidine-6-carboxylic acid dimethylamide;

7-Cyclopentyl-2-{5-[4-(2-ethyl-butyl)piperazin-1-yl]-pyridin-2-ylamino}-7H-pyrrolo[2,3-d]pyrimidine-6-carboxylic acid dimethylamide;

2-{5-[4-(2-Cyclohexyl-acetyl)piperazin-1-yl]-pyridin-2-ylamino}-7-cyclopentyl-7H-pyrrolo[2,3-d]pyrimidine-6-carboxylic acid dimethylamide;

7-Cyclopentyl-2-{5-[4-(3-cyclopentyl-propionyl)-piperazin-1-yl]-pyridin-2-ylamino}-7H-pyrrolo[2,3-d]pyrimidine-6-carboxylic acid dimethylamide;

7-Cyclopentyl-2-[5-(4-isobutylpiperazin-1-yl)-pyridin-2-ylamino]-7H-pyrrolo[2,3-d]pyrimidine-6-carboxylic acid dimethylamide;

{4-[6-(7-Cyclopentyl-6-dimethylcarbamoyl-7H-pyrrolo[2,3-d]pyrimidin-2-ylamino)pyridin-3-yl]-piperazin-1-yl}-acetic acid methyl ester;

7-Cyclopentyl-2-{5-[4-(2-isopropoxyethyl)-piperazin-1-yl]-pyridin-2-ylamino}-7H-pyrrolo[2,3-d]pyrimidine-6-carboxylic acid dimethylamide;

{4-[6-(7-Cyclopentyl-6-dimethylcarbamoyl-7H-pyrrolo[2,3-d]pyrimidin-2-ylamino)pyridin-3-yl]-piperazin-1-yl}-acetic acid ethyl ester;

4-(6-{7-Cyclopentyl-6-[(2-hydroxy-ethyl)methyl-carbamoyl]-7H-pyrrolo[2,3-d]pyrimidin-2-ylamino}-pyridin-3-yl)piperazine-1-carboxylic acid tert-butyl ester;

7-Cyclopentyl-2-{5-[4-(2-methyl-butyl)piperazin-1-yl]-pyridin-2-ylamino}-7H-pyrrolo[2,3-d]pyrimidine-6-carboxylic acid dimethylamide;

7-Cyclopentyl-2-[1'-(2-hydroxy-ethyl)-1',2',3',4',5',6'-hexahydro-[3,4']bipyridinyl-6-ylamino]-7H-pyrrolo[2,3-d]pyrimidine-6-carboxylic acid dimethylamide;

{4-[6-(7-Cyclopentyl-6-dimethylcarbamoyl-7H-pyrrolo[2,3-d]pyrimidin-2-ylamino)-pyridin-3-yl]piperazin-1-yl}-acetic acid; and 2-{4-[6-(7-Cyclopentyl-6-dimethylcarbamoyl-7H-pyrrolo[2,3-d]pyrimidin-2-ylamino)-pyridin-3-yl]-piperazin-1-yl}-propionic acid; or pharmaceutically acceptable salts thereof.

Assays

The inhibition of protein kinase activity by the compounds of the invention may be measured using a number of assays available in the art. Examples of such assays are described in the Exemplification section below.

Pharmaceutical Compositions

The language "effective amount" of the compound is that amount necessary or sufficient to treat or prevent a protein kinase-associated disorder, e.g. prevent the various morphological and somatic symptoms of a protein kinase-associated disorder, and/or a disease or condition described herein. In an example, an effective amount of the compound of the invention is the amount sufficient to treat a protein kinase-associated disorder in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a protein kinase-associated disorder. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical compositions for use in the treatment of these diseases. Methods of use of compounds of the present invention in the treatment of these diseases, or pharmaceutical preparations having compounds of the present invention for the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively,
delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a protein kinase-associated disorder.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Synthetic Procedure

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosauren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials. Intermediates and final products can be worked up and/or purified according to standard methods, e.g., using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the $H^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Prodrugs

This invention also encompasses pharmaceutical compositions containing, and methods of treating protein kinase-associated disorders through administering, pharmaceutically acceptable prodrugs of compounds of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Any reference to a compound of the present invention is therefore to be understood as referring also to the corresponding pro-drugs of the compound of the present invention, as appropriate and expedient.

Combinations

A compound of the present invention may also be used in combination with other agents, e.g., an additional protein kinase inhibitor that is or is not a compound of the invention, for treatment of a protein kinase-associated disorder in a subject.

By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

The compounds of the invention may be administered, simultaneously or sequentially, with an antiinflammatory, antiproliferative, chemotherapeutic agent, immunosuppressant, anti-cancer, cytotoxic agent or kinase inhibitor other than a compound of the Formula I or salt thereof. Further examples of agents that may be administered in combination with the compounds of the invention include, but are not limited to, a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-α inhibitors, anti-TNF antibodies or soluble TNF receptor, rapamycin, leflunimide, cyclooxygenase-2 inhibitors, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

Exemplification of the Invention

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

Experimental Procedure

Analytical Methods

In the examples, the compounds prepared are characterized by liquid chromatography and mass spectroscopy using the systems and operating conditions set out below. Where atoms with different isotopes are present and a single mass quoted, the mass quoted for the compound is the monoisotopic mass (i.e. $^{35}$Cl; $^{79}$Br etc.). Several systems are used, as described below, and these are equipped with, and are set up to run under, closely similar operating conditions. The operating conditions used are also described below.

LCMS analysis is performed using the following methods:

Waters Platform LC-MS System:
HPLC System: Waters 2795
Mass Spec Detector: Micromass Platform LC
PDA Detector: Waters 2996 PDA
Purity is measured by UV diode array detector (210-340 nm)
Method A
Eluent A: H$_2$O (10 mM NH$_4$HCO$_3$ buffer adjusted to pH=9.2 with NH$_4$OH)
Eluent B: CH$_3$CN
Gradient: 05-95% eluent B over 15 minutes
Flow: 0.8 mL/min
Column: Waters XBridge C18 54 2.1×50 mm
Method B
Eluent A: H$_2$O (10 mM NH$_4$HCO$_3$ buffer adjusted to pH=9.2 with NH$_4$OH)
Eluent B: CH$_3$CN
Gradient: 05-95% eluent B over 3.5 minutes
Flow: 0.8 ml/min
Column: Waters XBridge C18 54 2.1×50 mm
Method C
Eluent A: H$_2$O (0.1% Formic Acid)
Eluent B: CH$_3$CN (0.1% Formic Acid)
Gradient: 5-95% eluent B over 3.5 minutes
Flow: 0.8 mL/min
Column: Phenomenex Synergi 4μ MAX-RP 80A, 2.0×50 mm
Method D
Eluent A: H2O (0.1% Formic Acid)
Eluent B: CH3CN (0.1% Formic Acid)
Gradient: 5-95% acetonitrile/water over 7.75 minutes
Flow: 1.0 ml/min
Column: Inertsil ODS3 100×3 mm C18 column
Waters Fractionlynx LC-MS System:
HPLC System: 2767 autosampler 2525 binary gradient pump
Mass Spec Detector: Waters ZQ
PDA Detector: Waters 2996 PDA
Purity is measured by UV diode array detector (200-340 nm)
Method E
Eluent A: H$_2$O (10 mM NH$_4$HCO$_3$ buffer adjusted to pH=9.2 with NH$_4$OH)
Eluent B: CH$_3$CN
Gradient: 05-95% eluent B over 3.5 minutes
Flow: 2.0 mL/min
Method for Preparative Mass Directed Liquid Chromatography (LCMS)

Waters Fractionlynx System:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Software
Masslynx 4.1
Waters MS Running Conditions
Capillary voltage: 3.5 kV (3.2 kV on ES Negative)
Cone voltage: 25 V
Source Temperature: 120° C.
Multiplier: 500 V
Scan Range: 125-800 amu
Ionisation Mode ElectroSpray Positive or ElectroSpray Negative Once the analytical trace showed good chromatography a suitable preparative method of the same type is chosen. Typical running condition is:
Column
Waters XBridge C18 5μ 100×19 mm or Phenomenex Gemini, 5, 100×21.2 mm)
Mobile Phase
Solvent A: H$_2$O+10 mM NH$_4$HCO$_3$+NH$_4$OH, pH=9.2
Solvent B: CH$_3$CN
Flow rate: 24 ml/min
Gradient: Generally all gradients have an initial 0.4 min step with 95% A+5% B. Then according to analytical trace a 3.6 min gradient is chosen in order to achieve good separation (e.g. from 5% to 50% B for early retaining compounds; from 35% to 80% B for middle retaining compounds and so on).
Ish: 1.2 minute ish step is performed at the end of the gradient
Re-equilibration: 2.1 minutes re-equilibration step is ran to prepare the system for the next run
Make Up flow rate: 1 ml/min
All compounds are usually dissolved in 100% MeOH or 100% DMSO
Experimental Procedures
General Procedure A (BOC-deprotection)

Starting material is treated with excess HCl (4M solution in dioxane). MeOH and/or CHCl$_3$ as added to aid dissolution where necessary. After 16 h, the sample is evaporated in vacuo and the residue purified by either SiO$_2$ chromatography, ion exchange chromatography or preparative LCMS.

Nitrile Analogues

EXAMPLE A

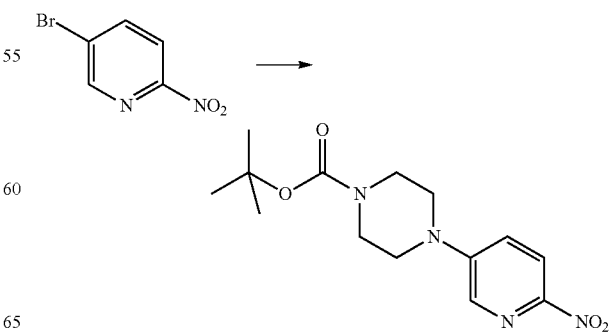

To a stirred solution of 5-bromo-2-nitropyridine (4.93 g, 24.3 mmol) and piperazine-1-carboxylic acid tert-butyl ester (4.97 g, 26.7 mmol) in CH₃CN (60 ml) is added DIPEA (4.65 mL, 26.7 mmol). The mixture is heated at reflux for 72 hours then cooled to room temperature and the precipitated product collected by filtration. The filtrate is concentrated and purified by flash column chromatography eluting with 30% EtOAc/petrol. The combined products are re-crystallized from EtOAc/petrol to give 4-(6-nitro-pyridin-3-yl)-piperazine-1-carboxylic acid tert-butyl ester, (4.50 g, 80% yield). MS (ESI) m/z 308 (M+H)⁺

EXAMPLE B

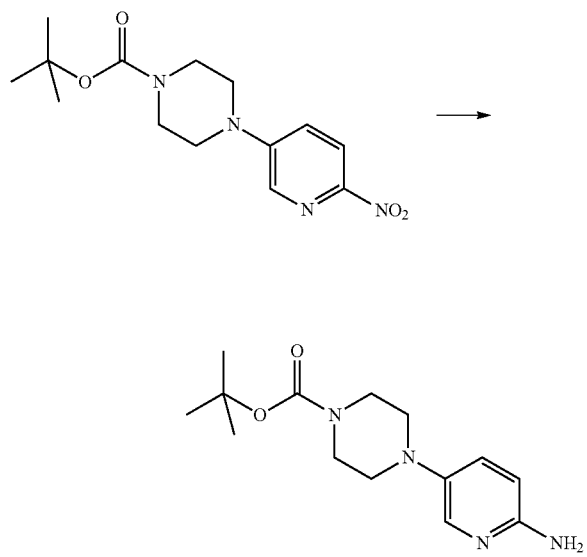

A mixture of 4-(6-nitro-pyridin-3-yl)-piperazine-1-carboxylic acid tert-butyl ester (3.40 g, 11.0 mmol) and 10% Pd—C (400 mg, 0.376 mmol) in ethanol (100 ml) and ethyl acetate (100 ml) is agitated under 1 atmosphere pressure of hydrogen overnight. The mixture is filtered and concentrated to give of 4-(6-amino-pyridin-3-yl)-piperazine-1-carboxylic acid tert-butyl ester (2.87 g, 94% yield). MS (ESI) m/z 278 (M+H)⁺

EXAMPLE 104

7-Cyclopentyl-2-(5-piperazin-1-yl-pyridin-2-ylamino)-7H-pyrrolo[2,3-d]pyrimidine-6-carbonitrile

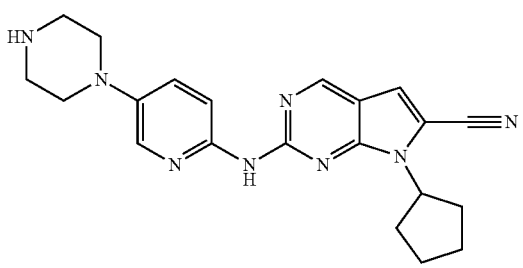

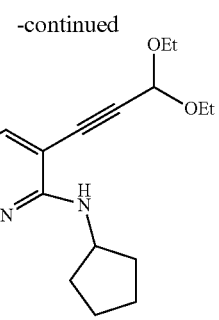

To a stirred solution of (5-bromo-2-chloro pyrimidin-4-yl)-cyclopentyl-amine (1.00 g, 3.62 mmol) and PdCl₂(dppf).dichloromethane (148 mg, 0.181 mmol) in THF (10 mL) is added Et₃N (0.757 mL, 5.43 mmol) and 3,3-diethoxy-propyne (0.778 mL, 5.43 mmol) sequentially at room temperature. The mixture is degassed under a stream of N2 and stirred at room temperature for 10 minutes before CuI (29 mg, 0.154 mmol) is added. The reaction vessel is evacuated and backfilled with N₂ (×3) and heated at 60° C. for 48 hours. The mixture is allowed to cool, diluted with EtOAc, filtered and partitioned between H₂O and ethyl acetate. The phases are separated and the aqueous layer is further extracted with EtOAc (×3), combined organic extracts are dried (MgSO₄), filtered and concentrated. The residue is purified by SiO₂ chromatography, eluting with a gradient of 5% EtOAc/petrol to 20% EtOAc/petrol to give [2-chloro-5-(3,3-diethoxy-prop-1-ynyl)-pyrimidin-4-yl]-cyclopentyl amine (636 mg, 54%). MS (ESI) m/z 324.2 (M+H)⁺

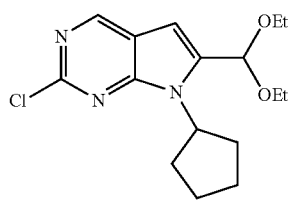 [SMILES: CCOC(OCC)c1cc2cnc(Cl)nc2n1C1CCCC1]

To a stirred solution of [2-chloro-5-(3,3-diethoxy-prop-1-ynyl)-pyrimidin-4-yl]-cyclopentyl-amine (7.50 g, 23.3 mmol) in THF (45 mL) is added 1N TBAF in THF (100 mL, 116 mmol) at room temperature. The reaction mixture is heated under reflux overnight. After cooling the mixture is partitioned between H₂O and dichloromethane. The phases are separated and the aqueous layer is extracted with dichloromethane (×2). The combined organic extracts are dried (MgSO₄), filtered and concentrated. The residue is purified by SiO₂ chromatography eluting with a gradient of 10% EtOAc/petrol to 30% EtOAc/petrol to give 2-chloro-7-cyclopentyl-6-diethoxymethyl-7H-pyrrolo[2,3-d]pyrimidine, (5.68 g, 76%). MS (ESI) m/z 324.1 (M+H)⁺

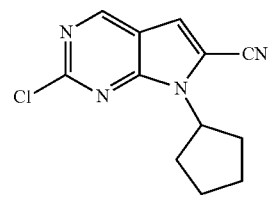 [SMILES: N#Cc1cc2cnc(Cl)nc2n1C1CCCC1]

To a stirred solution of 2-chloro-7-cyclopentyl-6-diethoxymethyl-7H-pyrrolo[2,3-d]pyrimidine (6.29 g, 19.5 mmol) in 1,4-dioxane (68 mL) is added conc. HCl (19 mL) at room temperature. The reaction mixture is stirred for 30 minutes, then neutralized with 2N NaOH aqueous solution and saturated NaHCO$_3$ aqueous solution. The mixture extracted into EtOAc (×3), combined organic extracts are dried (MgSO$_4$), filtered and concentrated to give 6 g of the crude 2-chloro-7-cyclopentyl-7H-pyrrolo[2,3-d]pyrimidine-6-carbaldehyde as a beige solid. To a stirred suspension of the crude 2-chloro-7-cyclopentyl-7H-pyrrolo[2,3-d]pyrimidine-6-carbaldehyde in MeCN (125 mL) and H$_2$O (125 mL) is added H$_2$N—SO$_3$H (6.62 g, 58.5 mmol) at room temperature. The reaction mixture is stirred for 3 hours before the pH is made >10 with 2N NaOH aqueous solution and the reaction stirred for 1 hour. The mixture extracted into dichloromethane (×3), combined organic extracts are dried (MgSO$_4$), filtered and concentrated. The residue is purified by SiO$_2$ chromatography, eluting with a gradient of 5% EtOAc/petrol to 20% EtOAc/petrol providing 4.00 g of 2-chloro-7-cyclopentyl-7H-pyrrolo[2,3-d]pyrimidine-6-carbonitrile as a white solid, 83% yield.

MS (ESI) m/z 247.0 (M+H)$^+$

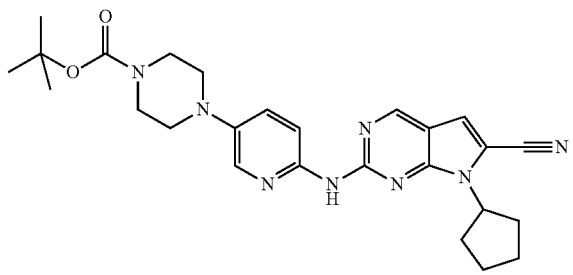 [SMILES: CC(C)(C)OC(=O)N1CCN(c2ccc(Nc3ncc4cc(C#N)n(C5CCCC5)c4n3)nc2)CC1]

Buchwald Procedure A

To a stirred solution of 2-chloro-7-cyclopentyl-7H-pyrrolo[2,3-d]pyrimidine-6-carbonitrile (80 mg, 0.324 mmol) in toluene (5.0 mL) is added sequentially Pd$_2$(dba)$_3$ (16 mg, 0.0162 mmol), 2-di-tert-butylphosphino-2',4',6'-triisopropylbiphenyl (14 mg, 0.0324 mmol) and 4-(6-amino-pyridin-3-yl)-piperazine-1-carboxylic acid tort-butyl ester (Example B) (99 mg, 0.357 mmol). The mixture is degassed under a stream of N$_2$ before LiHMDS (1M in THF; 0.650 mL, 0.650 mmol) is added. The reaction mixture is heated at 110° C. overnight. At room temperature the mixture is diluted with EtOAc filtered and concentrated. The residue is purified by SiO$_2$ chromatography, eluting with EtOAc gave 35 mg of material which is triturated with a 1:1 mixture of EtOAc/petrol providing 4-[6-(6-cyano-7-cyclopentyl-7H-pyrrolo[2,3-d]pyrimidin-2-ylamino)-pyridin-3-yl]-piperazine-1-carboxylic acid tert-butyl ester (20 mg).

Using General Procedure A, 4-[6-(6-cyano-7-cyclopentyl-7H-pyrrolo[2,3-d]pyrimidin-2-ylamino)-pyridin-3-yl]-piperazine-1-carboxylic acid tert-butyl ester (20 mg) gave crude product which is purified by SCX column (eluting with a 1:17 mixture of 2M NH$_3$ in MeOH/dichloromethane) to give a solid. Trituration with diethyl ether gave 7-cyclopentyl-2-(5-piperazin-1-yl-pyridin-2-ylamino)-7H-pyrrolo[2,3-d]pyrimidine-6-carbonitrile (8.8 mg, 7%) (over 2 steps). MS (ESI) m/z 389.2 (M+H)$^+$ (method A).

$^1$H NMR (400 MHz, DMSO-d$_6$): 9.68 (1H, s), 8.91 (1H, s), 8.11 (1H, d), 8.01 (1H, d), 7.51 (1H, s), 7.43 (1H, dd), 5.07 (1H, quintet), 3.10-2.99 (4H, m), 2.92-2.78 (4H, m), 2.32-2.08 (4H, m), 2.08-1.92 (2H, m), 1.82-1.66 (2H, m).

EXAMPLE 47

7-Cyclopentyl-2-((4-dimethylaminopiperidin)-1-yl-pyridin-2-ylamino)-7H-pyrrolo[2,3-d]pyrimidine-6-carbonitrile

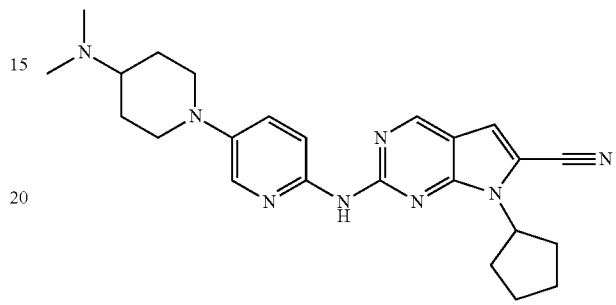

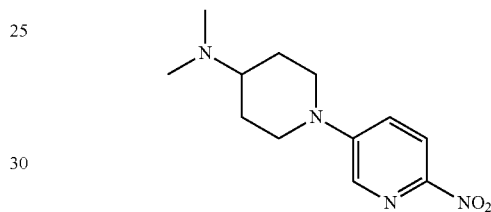

By repeating procedures described in Example A, 4-dimethylaminopiperidine (2.60 g, 18.4 mmol) to give dimethyl-[1-(6-nitro-pyridin-3-yl)-piperidin-4-yl]amine, (3.90 g, 80%) (purification by precipitation). MS (ESI) m/z 250.1 (M+H)$^+$

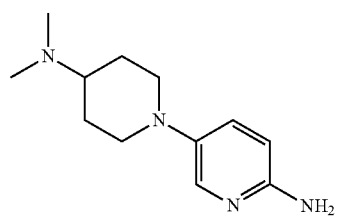 [SMILES: CN(C)C1CCN(c2ccc(N)nc2)CC1]

By repeating procedures described Example B, dimethyl-[1-(6-nitro-pyridin-3-yl)-piperidin-4-yl]-amine (3.90 g, 15.6 mmol) gave 5-(4-dimethylaminopiperidin-1-yl)-pyridin-2-ylamine (3.32 g, 97%). [M−H]$^+$=219.1.

Following Buchwald Procedure A, 2-chloro-7-cyclopentyl-7H-pyrrolo[2,3-d]pyrimidine-6-carbonitrile (95 mg, 0.385 mmol) and 5-(4-dimethylaminopiperidin-1-yl)-pyridin-2-ylamine (93 mg, 0.424 mmol) to give 7-cyclopentyl-2-((4-dimethylaminopiperidin)-1-yl-pyridin-2-ylamino)-7H-pyrrolo[2,3-d]pyrimidine-6-carbonitrile (77 mg, 46%) [following trituration with 1:1 mixture of EtOAc/petrol]

MS (ESI) m/z 431.2 (M+H)$^+$ (method A).

$^1$H NMR (400 MHz, DMSO-d$_6$): 9.66 (1H, s), 8.90 (1H, s), 8.09 (1H, d), 8.02 (1H, d), 7.51 (1H, s), 7.45 (1H, dd), 5.07 (1H, quintet), 3.74-3.62 (2H, m), 2.75-2.63 (2H, m), 2.30-

2.08 (11H, m), 2.08-1.92 (2H, m), 1.92-1.81 (2H, m), 1.81-1.66 (2H, m), 1.59-1.44 (2H, m).

EXAMPLE 2 rac-7-Cyclopentyl-2-[5-(3-methyl-piperazin-1-yl)-pyridin-2-ylamino]-7H-pyrrolo[2,3-d]pyrimidine-6-carbonitrile

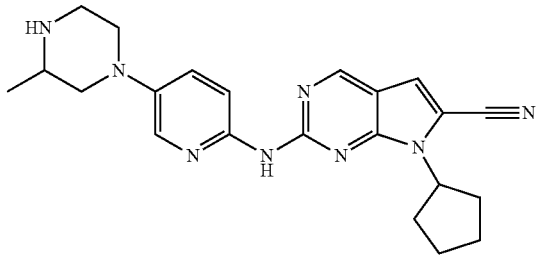

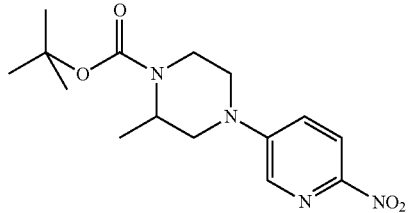 [SMILES: CC1CN(c2ccc(N)nc2)CCN1C(=O)OC(C)(C)C]

By repeating procedures described in Example A, 2-methyl-piperazine-1-carboxylic acid tert-butyl ester (1.08 g, 5.40 mmol) gave 2-methyl-4-(6-nitro-pyridin-3-yl)-piperazine-1-carboxylic acid tert-butyl ester (0.610 g, 39%) (following SiO$_2$ chromatography, eluting with 2% MeOH/dichloromethane). MS (ESI) m/z 323 (M+H)$^+$

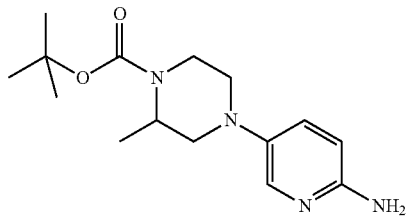

By repeating procedures described in Example B, 2-methyl-4-(6-nitro-pyridin-3-yl)-piperazine-1-carboxylic acid tert-butyl ester (600 mg, 1.52 mmol) is hydrogenated over Pd—C on an H-cube (Thales) (instead of under an atmosphere of hydrogen) to give 4-(6-amino-pyridin-3-yl)-2-methyl-piperazine-1-carboxylic acid tert-butyl ester (544 mg, 98%). MS (ESI) m/z 293 (M+H)$^+$

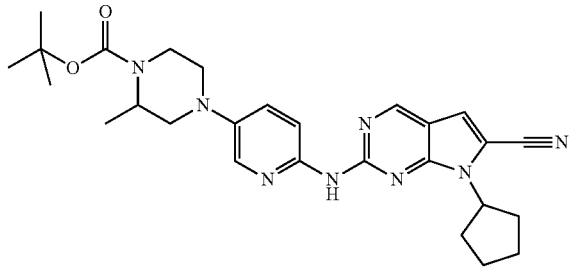 [SMILES: CC1CN(c2ccc(Nc3ncc4cc(C#N)n(C5CCCC5)c4n3)nc2)CCN1C(=O)OC(C)(C)C]

Using Buchwald Procedure A, 2-chloro-7-cyclopentyl-7H-pyrrolo[2,3-d]pyrimidine-6-carbonitrile (95 mg, 0.385 mmol) and 4-(6-amino-pyridin-3-yl)-2-methyl-piperazine-1-carboxylic acid tert-butyl ester (124 mg, 0.424 mmol) gave 4-[6-(6-cyano-7-cyclopentyl-7H-pyrrolo[2,3-d]pyrimidin-2-ylamino)-pyridin-3-yl]-2-methyl-piperazine-1-carboxylic acid tert-butyl ester (128 mg) [following SiO$_2$ chromatography eluting with 1-2.5% MeOH/dichloromethane and subsequent trituration with diethyl ether]. The material is used directly in the next step.

Using General Procedure A, 4-[6-(6-cyano-7-cyclopentyl-7H-pyrrolo[2,3-d]pyrimidin-2-ylamino)-pyridin-3-yl]-2-methyl-piperazine-1-carboxylic acid tert-butyl ester gave 7-cyclopentyl-2-[5-(3-methyl-piperazin-1-yl)-pyridin-2-ylamino]-7H-pyrrolo[2,3-d]pyrimidine-6-carbonitrile (91 mg, 59% over 2 steps) [following purification by Strata-NH$_2$ column, eluting with a 1:1 mixture of MeOH/dichloromethane, and subsequent trituration with diethyl ether]. MS (ESI) m/z 403.2 (M+H)$^+$ (method A).

$^1$H NMR (400 MHz, DMSO-d$_6$): 10.00 (1H, s), 9.00-8.87 (2H, m), 8.64-8.51 (1H, m), 8.17-8.05 (2H, m), 7.61 (1H, d), 7.55 (1H, s), 5.10 (1H, quintet), 3.85-3.67 (2H, m), 3.50-3.36 (2H, m), 3.20 (1H, dd), 2.97 (1H, t), 2.75 (1H, t), 2.32 (3H, s), 2.29-2.10 (4H, m), 2.08-1.94 (2H, m), 1.82-1.68 (2H, m), 1.29 (3H, d).

EXAMPLE 106

7-Cyclopentyl-2-(5-[1,4]diazepan-1-yl-pyridin-2-ylamino)-7H-pyrrolo[2,3-d]pyrimidine-6-carbonitrile

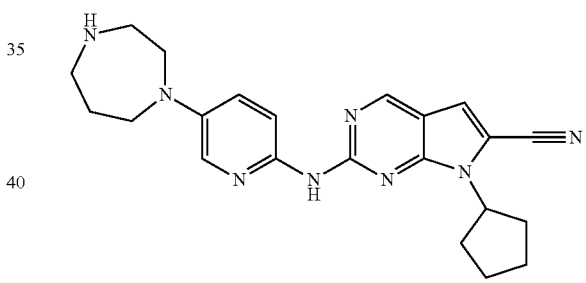

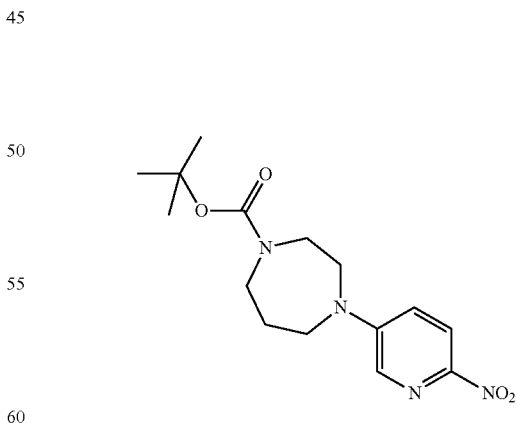

By repeating procedures described in Example A, [1,4]diazepane-1-carboxylic acid tert-butyl ester (1.08 g, 5.40 mmol) in CH$_3$CN (20 ml) gave 4-(6-nitro-pyridin-3-yl)-[1,4]diazepane-1-carboxylic acid tert-butyl ester (533 mg) [following SiO$_2$ chromatography eluting with 2% MeOH/dichloromethane]. MS (ESI) m/z 323 (M+H)$^+$

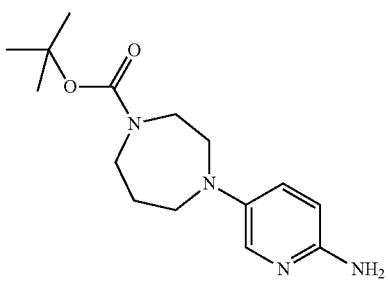 [SMILES: CC(C)(C)OC(=O)N1CCCN(c2ccc(N)nc2)CC1]

By repeating procedures described in Example B, 4-(6-nitro-pyridin-3-yl)-[1,4]diazepane-1-carboxylic acid tert-butyl ester (490 mg, 1.52 mmol) is hydrogenated over Pd—C on an H-cube (Thales) (instead of under an atmosphere of hydrogen) to give 4-(6-amino-pyridin-3-yl)-[1,4]diazepane-1-carboxylic acid tert-butyl ester (544 mg, 98%). MS (ESI) m/z 293 (M+H)+

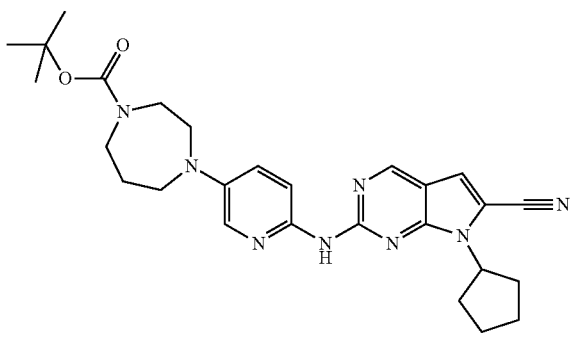 [SMILES: CC(C)(C)OC(=O)N1CCCN(c2ccc(Nc3ncc4cc(C#N)n(C5CCCC5)c4n3)nc2)CC1]

Following Buchwald Procedure A, 2-chloro-7-cyclopentyl-7H-pyrrolo[2,3-d]pyrimidine-6-carbonitrile (95 mg, 0.385 mmol) and 4-(6-amino-pyridin-3-yl)-[1,4]diazepane-1-carboxylic acid tert-butyl ester (124 mg, 0.424 mmol) gave 4-[6-(6-cyano-7-cyclopentyl-7H-pyrrolo[2,3-d]pyrimidin-2-ylamino)-pyridin-3-yl]-[1,4]diazepane-1-carboxylic acid tert-butyl ester (96 mg) [following SiO₂ chromatography, eluting with a 1-3% MeOH/dichloromethane and subsequent trituration with a diethyl ether]. The material is used directly in the next step.

Following General Procedure A, 4-[6-(6-cyano-7-cyclopentyl-7H-pyrrolo[2,3-d]pyrimidin-2-ylamino)-pyridin-3-yl]-[1,4]diazepane-1-carboxylic acid tert-butyl ester gave 7-cyclopentyl-2-(5-[1,4]diazepan-1-yl-pyridin-2-ylamino)-7H-pyrrolo[2,3-d]pyrimidine-6-carbonitrile (71 mg, 46% over 2 steps [following purification by Strata-NH₂ column, eluting with a 1:1 mixture of MeOH/dichloromethane, and subsequent trituration with diethyl ether]. MS (ESI) m/z 403.2 (M+H)+ (method A).

¹H NMR (400 MHz, DMSO-d₆): 9.01 (1H, s), 8.67 (2H, s), 7.95-7.80 (2H, m), 7.73-7.54 (2H, m), 5.14 (1H, quintet), 3.75 (2H, t), 3.54 (2H, t), 3.34-3.26 (2H, m), 3.23-3.14 (2H, m), 2.33 (3H, s), 2.27-2.13 (4H, m), 2.13-1.93 (4H, m), 1.83-1.67 (2H, m).

EXAMPLE 105

7-Cyclopentyl-2-(5-hydroxymethyl-pyridin-2-ylamino)-7H-pyrrolo[2,3-d]pyrimidine-6-carbonitrile

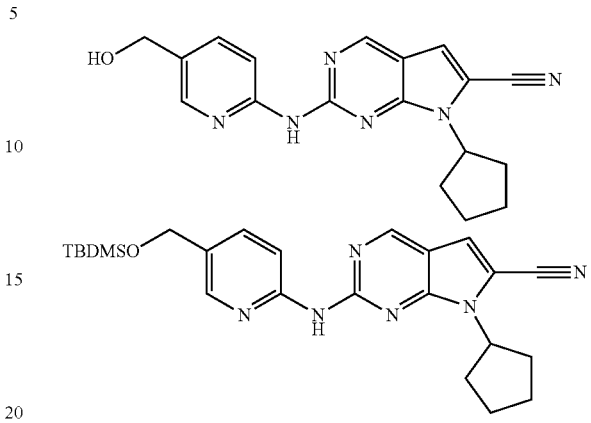

Following Buchwald Procedure A, 2-chloro-7-cyclopentyl-7H-pyrrolo[2,3-d]pyrimidine-6-carbonitrile (95 mg, 0.385 mmol) and 5-(tert-butyl-dimethyl-silanyloxymethyl)-pyridin-2-ylamine (101 mg, 0.424 mmol) (Example C) gave 114 mg of 2-[5-(tert-butyl-dimethyl-silanyloxymethyl)-pyridin-2-ylamino]-7-cyclopentyl-7H-pyrrolo[2,3-d]pyrimidine-6-carbonitrile [following SiO₂ chromatography eluting with 1-2% MeOH/dichloromethane and subsequent trituration with diethyl ether].

To a stirred solution of 2-[5-(tert-butyl-dimethyl-silanyloxymethyl)-pyridin-2-ylamino]-7-cyclopentyl-7H-pyrrolo[2,3-d]pyrimidine-6-carbonitrile in THF (2.0 mL) is added HF.pyridine (0.080 mL) at 0° C. The reaction mixture stirred at room temperature for 16 h before it is diluted with ethyl acetate, ished with saturated NaHCO₃ solution, dried (MgSO₄), filtered and concentrated. Trituration with diethyl ether gave 7-cyclopentyl-2-(5-hydroxymethyl-pyridin-2-ylamino)-7H-pyrrolo[2,3-d]pyrimidine-6-carbonitrile, 68 mg, 53% yield (over 2 steps). MS (ESI) m/z 335.0 (M+H)+ (method A).

¹H NMR (400 MHz, DMSO-d₆): 9.96 (1H, s), 8.97 (1H, s), 8.33-8.21 (2H, m), 7.75 (1H, dd), 7.55 (1H, s), 5.19 (1H, t), 5.10 (1H, quintet), 4.49 (2H, d), 2.37-2.10 (4H, m), 2.10-1.92 (2H, m), 1.85-1.67 (2H, m).

EXAMPLE 9

2-{5-[4-(2-Cyano-ethyl)-piperazin-1-yl]-pyridin-2-ylamino}-7-cyclopentyl-7H-pyrrolo[2,3-d]pyrimidine-6-carboxylic acid dimethylamide

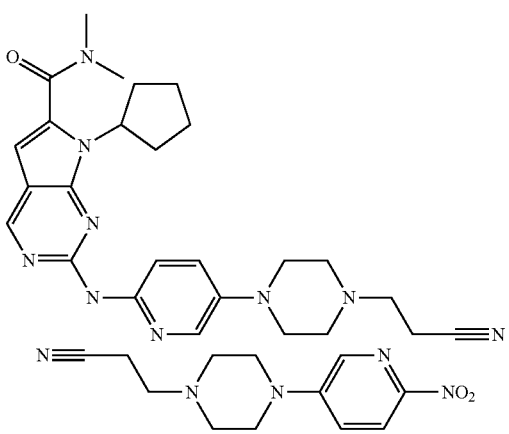

By repeating procedures described in Example A, (except heating at 130° C. for 1 h in a CEM Discovery microwave, rather than heating at reflux) 3-piperazin-1-yl-propionitrile (510 mg, 3.63 mmol) gave 3-[4-(6-nitro-pyridin-3-yl)-piperazin-1-yl]-propionitrile as a white crystalline solid (212 mg, 25%) [following SiO₂ chromatography, eluting with 0-10% methanol/dichlormethane and subsequent recrystallization form ethyl acetate/petroleum ether (212 mg, 25%). MS (ESI) m/z 262.1 (M+H)⁺

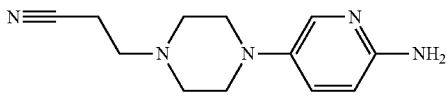

By repeating procedures described in Example B, 3-[4-(6-nitro-pyridin-3-yl)-piperazin-1-yl]-propionitrile (200 mg, 0.763 mmol) gave 3-[4-(6-amino-pyridin-3-yl)-piperazin-1-yl]-propionitrile (165 mg, 94%) which is used in the next step without further purification. MS (ESI) m/z 232.1 (M+H)⁺

Following Buchwald Procedure A, 3-[4-(6-amino-pyridin-3-yl)-piperazin-1-yl]-propionitrile (173 mg, 0.751 mmol) and 2-chloro-7-cyclopentyl-7H-pyrrolo[2,3-d]pyrimidine-6-carboxylic acid dimethylamide (200 mg, 0.683 mmol) gave 2-{5-[4-(2-cyano-ethyl)-piperazin-1-yl]-pyridin-2-ylamino}-7-cyclopentyl-7H-pyrrolo[2,3-d]pyrimidine-6-carboxylic acid dimethylamide (34 mg, 10%) [following purification by preparative LCMS]. MS (ESI) m/z 488.2 (M+H)⁻ (method B).

¹H NMR (400 MHz, Me-d₃-OD): 8.72 (1H, s), 8.24 (1H, d), 7.99 (1H, d), 7.51 (1H, dd), 6.62 (1H, s), 4.82-4.72 (1H, m), 3.23 (4H, t), 3.17 (6H, s), 2.82-2.65 (8H, m), 2.62-2.48 (2H, m), 2.17-1.98 (4H, m), 1.86-1.64 (2H, m).

EXAMPLE 25

7-Cyclopentyl-2-{5-[4-(2,2,2-trifluoro-ethyl)-piperazin-1-yl]-pyridin-2-ylamino}-7H-pyrrolo[2,3-d]pyrimidine-6-carboxylic acid dimethylamide

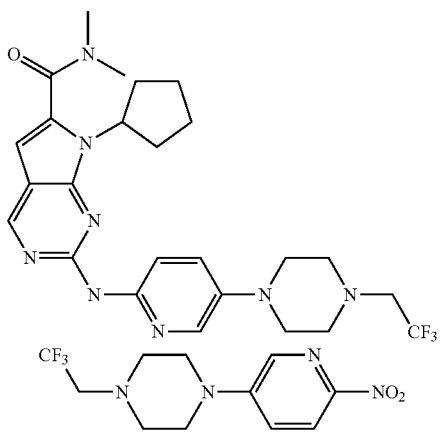

By repeating procedures described in Example A (except heating at 130° C. for 1 h in a CEM Discovery microwave, rather than heating at reflux), 1-(2,2,2-trifluoroethyl)piperazine (1.31 g, 5.41 mmol) gave 1-(6-nitro-pyridin-3-yl)-4-(2,2,2-trifluoroethyl)-piperazine (210 mg, 15%) [following purification by SiO₂ chromatography, eluting with 0-10% MeOH/dichloromethane].

MS (ESI) m/z 291.1 (M+H)⁺

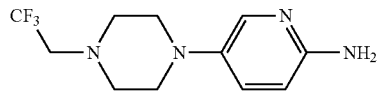 [SMILES: Nc1ccc(N2CCN(CC(F)(F)F)CC2)cn1]

By repeating procedures described in Example B, 6-nitro-pyridin-3-yl)-4-(2,2,2-trifluoro-ethyl)-piperazine (210 mg, 0.724 mmol) gave 5-[4-(2,2,2-trifluoro-ethyl)-piperazin-1-yl]-pyridin-2-ylamine (158 mg, 84%) which is used in the next step without further purification. MS (ESI) m/z 261.1 (M+H)⁺

Buchwald Method B

A mixture of 5-[4-(2,2,2-trifluoro-ethyl)-piperazin-1-yl]-pyridin-2-ylamine (158 mg, 0.607 mmol), 2-chloro-7-cyclopentyl-7H-pyrrolo[2,3-d]pyrimidine-6-carboxylic acid dimethylamide (118 mg, 0.405 mmol), Pd₂(dba)₃ (18.5 mg, 0.020 mmol), BINAP (25 mg, 0.040 mmol) and sodium-tert-butoxide (70 mg, 0.728 mmol) in dioxane (3.5 mL) is degassed and heated to 100° C. for 1 h in a CEM Discover microwave. The reaction mixture is partitioned between dichloromethane and saturated NaHCO₃ solution. The organic layer is separated and the aqueous layer extracted with further dichloromethane. The combined organics are ished with brine, dried (MgSO₄), filtered and concentrated. The crude product is purified using silica gel chromatography (0 to 10% methanol/dichloromethane) to give 7-cyclopentyl-2-{5-[4-(2,2,2-trifluoro-ethyl)-piperazin-1-yl]-pyridin-2-ylamino}-7H-pyrrolo[2,3-d]pyrimidine-6-carboxylic acid dimethylamide, which is purified further by trituration with acetonitrile (115 mg, 55%). MS (ESI) m/z 517.2 (M+H)ˡ (method A).

¹H NMR (400 MHz, Me-d₃-OD): 8.72 (1H, s), 8.24 (1H, d), 7.98 (1H, d), 7.50 (1H, dd), 6.62 (1H, s), 4.81-4.72 (1H, m), 3.27-3.09 (12H, m), 2.89 (4H, t), 2.61-2.49 (2H, m), 2.16-2.01 (4H, m), 1.81-1.69 (2H, m).

EXAMPLE 8

7-Cyclopentyl-2-(5-[1,4]diazepan-1-yl-pyridin-2-ylamino)-7H-pyrrolo[2,3-d]pyrimidine-6-carboxylic acid dimethylamide

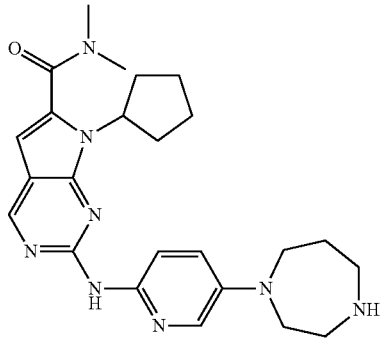 [SMILES: CN(C)C(=O)c1cc2cnc(Nc3ccc(N4CCCNCC4)cn3)nc2n1C1CCCC1]

Using Buchwald Procedure A, 2-chloro-7-cyclopentyl-7H-pyrrolo[2,3-d]pyrimidine-6-carboxylic acid dimethyl amide (0.13 g, 0.444 mmol) gave 4-[6-(7-cyclopentyl-6-dimethylcarbamoyl-7H-pyrrolo[2,3-d]pyrimidin-2-ylamino)-pyridin-3-yl]-[1,4]diazepane-1-carboxylic acid tert-butyl ester (66 mg, 27%) [following purification by SiO₂ chromatography eluting with 0-3% MeOH in dichloromethane]. MS (ESI) m/z 549.3 (M+H)⁺

Using General Procedure A, 4-[6-(7-cyclopentyl-6-dimethylcarbamoyl-7H-pyrrolo[2,3-d]pyrimidin-2-ylamino)-pyridin-3-yl]-[1,4]diazepane-1-carboxylic acid tert-butyl ester (66 mg, 0.12 mmol) is used to give 7-cyclopentyl-2-(5-[1,4]diazepan-1-yl-pyridin-2-ylamino)-7H-pyrrolo[2,3-d]pyrimidine-6-carboxylic acid dimethylamide (35 mg, 65%) as a yellowish solid [following purification by SCX column chromatography eluting with 15% (NH₃ 2 M in MeOH)/DCM].

MS (ESI) m/z 449.2 (M+H)¹ (method C).
¹H NMR (400 MHz, Me-d3-OD): 8.69 (1H, s), 8.08 (1H, d), 7.83 (1H, d), 7.30 (1H, dd), 6.60 (1H, s), 4.76 (1H, quintet), 3.63 (4H, t), 3.17 (7H, s), 3.09 (2H, t), 2.91 (2H, t), 2.61-2.45 (2H, m), 2.17-1.93 (7H, m), 1.80-1.63 (2H, m).

EXAMPLE 13

Rac-2-[5-(3-Amino-pyrrolidin-1-yl)-pyridin-2-ylamino]-7-cyclopentyl-7H-pyrrolo[2,3-d]pyrimidine-6-carboxylic acid dimethylamide

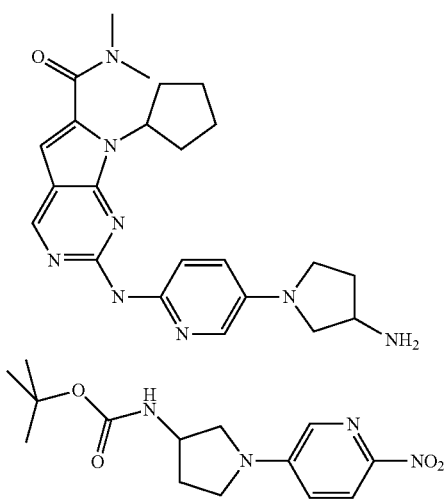

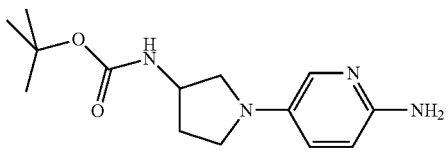 [SMILES: CC(C)(C)OC(=O)NC1CCN(c2ccc(N)nc2)C1]

By repeating procedures described in Example A, pyrrolidin-3-yl-carbamic acid tert-butyl ester (2.52 g, 13.5 mmol) gave [1-(6-nitro-pyridin-3-yl)-pyrrolidin-3-yl]-carbamic acid tert-butyl ester as a yellow solid (2.16 g, 57%) [following trituration with EtOAc] [M+H]⁺=309.2.

By repeating procedures described in Example B, [1-(6-nitro-pyridin-3-yl)-pyrrolidin-3-yl]-carbamic acid tert-butyl ester (2.16 g, 7.01 mmol) gave [1-(6-amino-pyridin-3-yl)-pyrrolidin-3-yl]-carbamic acid tert-butyl ester as a purple solid (1.12 g, 56%). [following SiO₂ chromatography eluting with 2.5-7.5% MeOH/dichloromethane). [M+H]⁺=279.2.

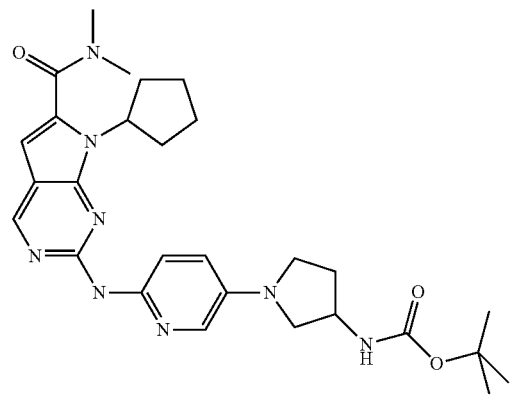 [SMILES: CN(C)C(=O)c1cc2cnc(Nc3ccc(N4CCC(NC(=O)OC(C)(C)C)C4)cn3)nc2n1C1CCCC1]

Using Buchwald Procedure A, 2-chloro-7-cyclopentyl-7H-pyrrolo[2,3-d]pyrimidine-6-carboxylic acid dimethyl amide (0.13 g, 0.444 mmol) and [1-(6-amino-pyridin-3-yl)-pyrrolidin-3-yl]-carbamic acid tert-butyl ester (0.136 g, 0.488 mmol) gave {1-[6-(7-cyclopentyl-6-dimethylcarbamoyl-7H-pyrrolo[2,3-d]pyrimidin-2-ylamino)-pyridin-3-yl]-pyrrolidin-3-yl}-carbamic acid tert-butyl ester (35 mg, 15%) (following SiO₂ chromatography, eluting with 0-3% MeOH/dichloromethane).

MS (ESI) m/z 535.3 (M+H)⁺
Using General Procedure A, {1-[6-(7-cyclopentyl-6-dimethylcarbamoyl-7H-pyrrolo[2,3-d]pyrimidin-2-ylamino)-pyridin-3-yl]-pyrrolidin-3-yl}-carbamic acid tert-butyl ester (35 mg, 0.0655 mmol) gave rac-2-[5-(3-amino-pyrrolidin-1-yl)-pyridin-2-ylamino]-7-cyclopentyl-7H-pyrrolo[2,3-d]pyrimidine-6-carboxylic acid dimethylamide as a yellow solid (11 mg, 39%) [following SiO₂ chromatography eluting with 5% (2.0 M NH; in MeOH)/DCM]. MS (ESI) m/z 435.2 (M+H)⁺ (method C).
¹H NMR (400 MHz, Me-d3-OD): 8.68 (1H, s), 8.10 (1H, d), 7.66 (1H, d), 7.11 (1H, dd), 6.60 (1H, s), 4.79-4.66 (1H, m), 3.76-3.65 (1H, m), 3.60-3.46 (2H, m), 3.17 (6H, s), 3.15-2.87 (2H, m), 2.62-2.44 (2H, m), 2.37-2.22 (1H, m), 2.17-1.98 (4H, m), 1.98-1.80 (1H, m), 1.80-1.63 (2H, m).

EXAMPLE 19

7-Cyclopentyl-2-[5-(3-methyl-piperazin-1-yl)-pyridin-2-ylamino]-7H-pyrrolo[2,3-d]pyrimidine-6-carboxylic acid dimethylamide

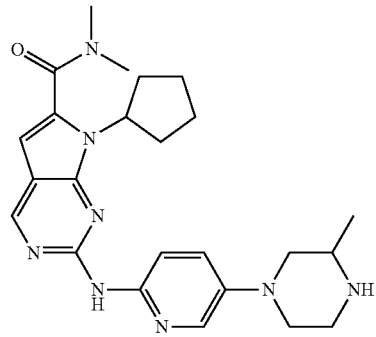 [SMILES: CC1CN(c2ccc(Nc3ncc4cc(C(=O)N(C)C)n(C5CCCC5)c4n3)nc2)CCN1]

Using Buchwald Procedure A, 2-chloro-7-cyclopentyl-7H-pyrrolo[2,3-d]pyrimidine-6-carboxylic acid dimethyl amide (0.142 g, 0.485 mmol) and (+/−)-4-(6-amino-pyridin-3-yl)-2-methyl-piperazine-1-carboxylic acid tert-butyl ester (0.156 g, 0.533 mmol) gave 4-[6-(7-cyclopentyl-6-dimethyl-carbamoyl-7H-pyrrolo[2,3-d]pyrimidin-2-ylamino) pyridin-3-yl]-2-methyl-piperazine-1-carboxylic acid tert-butyl ester (260 mg, 97%) (following SiO₂ chromatography, eluting with 0-3% MeOH/dichloromethane). MS (ESI) m/z 549.3 (M+H)

Using General Procedure A, 4-[6-(7-cyclopentyl-6-dimethylcarbamoyl-7H-pyrrolo[2,3-d]pyrimidin-2-ylamino)-pyridin-3-yl]-2-methyl-piperazine-1-carboxylic acid tert-butyl ester (260 mg, 0.474 mmol) gave 7-cyclopentyl-2-[5-(3-methyl-piperazin-1-yl)-pyridin-2-ylamino]-7H-pyrrolo[2,3-d]pyrimidine-6-carboxylic acid dimethylamide as a beige solid (67 mg, 31%) [following SiO₂ chromatography eluting with 5% (2.0 M NH₃ in methanol/dichloromethane].

MS (ESI) m/z 449.4 (M+H)⁺ (method D).

¹H NMR (400 MHz, DMSO-d6): 9.23 (1H, s), 8.76 (1H, s), 8.13 (1H, d), 7.98 (1H, d), 7.41 (1H, dd), 6.60 (1H, s), 4.80-4.67 (1H, m), 3.46 (2H, t), 3.06 (6H, s), 3.02-2.90 (1H, m), 2.90-2.74 (2H, m), 2.61-2.49 (2H, m), 2.49-2.27 (2H, m), 2.27-2.08 (2H, m), 1.98 (4H, s), 1.65 (2H, d), 1.03 (3H, d).

EXAMPLE 5

7-Cyclopentyl-2-{5-[4-(2-fluoro-ethyl)-piperazin-1-yl]-pyridin-2-ylamino}-7H-pyrrolo[2,3-d]pyrimidine-6-carboxylic acid dimethylamide

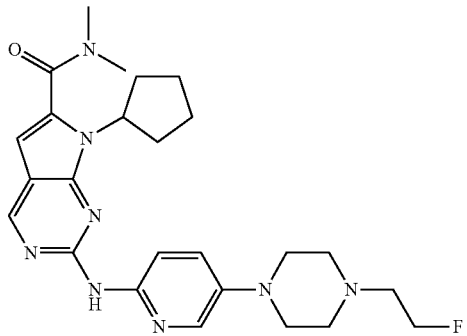 [SMILES: CN(C)C(=O)c1cc2cnc(Nc3ccc(N4CCN(CCF)CC4)cn3)nc2n1C1CCCC1]

To a solution of 7-cyclopentyl-2-(5-piperazin-1-yl-pyridin-2-ylamino)-7H-pyrrolo[2,3-d]pyrimidine-6-carboxylic acid dimethylamide hydrochloride (150 mg, 0.318 mmol) and potassium carbonate (132 mg, 0.955 mmol) in acetonitrile (3 mL) and DMF (2 mL) is added 1-bromo-2-fluoroethane (0.035 mL, 0.478 mmol) and the reaction mixture is heated to 80° C. for 24 h in a sealed reaction vial. Upon cooling, the reaction mixture is partitioned between dichloromethane and water. The organic layer is separated and the aqueous layer extracted further with dichloromethane. The combined organics are ished with brine, dried (MgSO₄), filtered and concentrated. The crude product is purified using silica gel chromatography (0 to 10% methanol/dichloromethane) to give 7-cyclopentyl-2-{5-[4-(2-fluoro-ethyl)-piperazin-1-yl]-pyridin-2-ylamino}-7H-pyrrolo[2,3-d]pyrimidine-6-carboxylic acid dimethylamide (84 mg, 55%) as an off white solid.

MS (ESI) m/z 481.2 (M+H)⁺ (method B).

¹H NMR (400 MHz, DMSO-d6): 9.23 (1H, s), 8.75 (1H, s), 8.14 (1H, d), 7.99 (1H, d), 7.43 (1H, dd), 6.60 (1H, s), 4.79-4.68 (1H, m), 4.64 (1H, t), 4.53 (1H, t), 3.14 (4H, t), 3.06 (6H, s), 2.72 (1H, t), 2.68-2.60 (5H, m), 2.49-2.37 (2H, m), 1.98 (4H, s), 1.65 (2H, d).

EXAMPLE 84

2-[5-(4-Cyanomethyl-piperazin-1-yl)-pyridin-2-ylamino]-7-cyclopentyl-7H-pyrrolo[2,3-d]pyrimidine-6-carboxylic acid dimethylamide

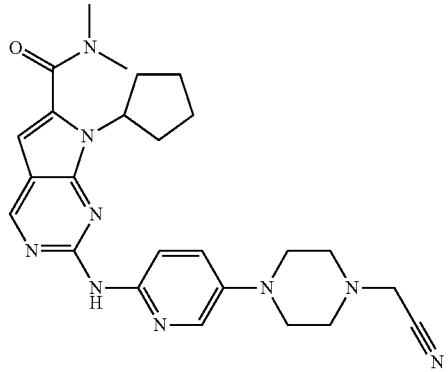 [SMILES: CN(C)C(=O)c1cc2cnc(Nc3ccc(N4CCN(CC#N)CC4)cn3)nc2n1C1CCCC1]

By repeating procedures described in Example 5, 7-cyclopentyl-2-(5-piperazin-1-yl-pyridin-2-ylamino)-7H-pyrrolo[2,3-d]pyrimidine-6-carboxylic acid dimethylamide hydrochloride (150 mg, 0.318 mmol) gave 2-[5-(4-cyanomethyl-piperazin-1-yl)-pyridin-2-ylamino]-7-cyclopentyl-7H-pyrrolo[2,3-d]pyrimidine-6-carboxylic acid dimethylamide as an off white solid (99 mg, 66%).

MS (ESI) m/z 474.4 (M+H)⁺ (method B).

¹H NMR (400 MHz, DMSO-d₆): 9.25 (1H, s), 8.75 (1H, s), 8.15 (1H, d), 8.04-7.97 (1H, d), 7.48-7.41 (1H, dd), 6.59 (1H, s), 4.78-4.69 (1H, m), 3.81 (2H, s), 3.18 (4H, t), 3.06 (6H, s), 2.66 (5H, t), 2.43 (1H, d), 1.99 (4H, s), 1.70-1.61 (2H, m).

EXAMPLE 14

7-Cyclopentyl-2-{5-[4-(2-methoxy-ethyl)-piperazin-1-yl]-pyridin-2-ylamino}-7H-pyrrolo[2,3-d]pyrimidine-6-carboxylic acid dimethylamide

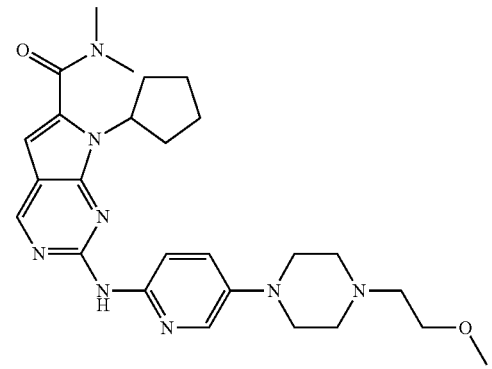 [SMILES: COCCN1CCN(c2ccc(Nc3ncc4cc(C(=O)N(C)C)n(C5CCCC5)c4n3)nc2)CC1]

By repeating procedures described in Example 5, 7-cyclopentyl-2-(5-piperazin-1-yl-pyridin-2-ylamino)-7H-pyrrolo[2,3-d]pyrimidine-6-carboxylic acid dimethylamide hydro chloride (15.0 mg, 0.318 mmol) gave 7-cyclopentyl-2-{5-[4-(2-methoxy-ethyl)-piperazin-1-yl]-pyridin-2-ylamino}-7H-pyrrolo[2,3-d]pyrimidine-6-carboxylic acid dimethylamide as an off white solid (46 mg, 29%).

MS (ESI) m/z 493.5 (M+H)+ (method B).

$^1$H NMR (400 MHz, DMSO-$d_6$): 9.22 (1H, s), 8.75 (1H, s), 8.14 (1H, d), 7.98 (1H, d), 7.42 (1H, dd), 6.60 (1H, s), 4.78-4.69 (1H, m), 3.48 (2H, t), 3.26 (3H, s), 3.18-3.09 (4H, m), 3.06 (6H, s), 2.65-2.52 (6H, m), 2.47-2.35 (2H, m), 1.98 (4H, s), 1.71-1.58 (2H, m).

EXAMPLE 10

2-[5-(4-Carbamoylmethyl-piperazin-1-yl)-pyridin-2-ylamino]-7-cyclopentyl-7H-pyrrolo[2,3-d]pyrimidine-6-carboxylic acid dimethylamide

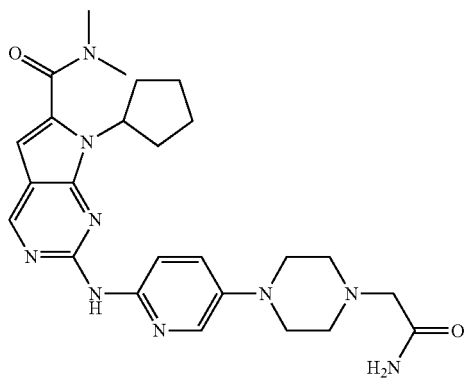 [SMILES: CN(C)C(=O)c1cc2cnc(Nc3ccc(N4CCN(CC(N)=O)CC4)cn3)nc2n1C1CCCC1]

By repeating procedures described in Example 5, 7-cyclopentyl-2-(5-piperazin-1-yl-pyridin-2-ylamino)-7H-pyrrolo[2,3-d]pyrimidine-6-carboxylic acid dimethylamide hydrochloride (100 mg, 0.212 mmol) gave 2-[5-(4-carbamoylmethyl-piperazin-1-yl)-pyridin-2-ylamino]-7-cyclopentyl-7H-pyrrolo[2,3-d]pyrimidine-6-carboxylic acid dimethylamide (66 mg, 63%) as an off white solid [following SiO$_2$ chromatography eluting with 0 to 10% (2M NH$_3$ in methanol/dichloromethane).

MS (ESI) m/z 492.3 (M+H)+ (method B).

$^1$H NMR (400 MHz, DMSO-$d_6$): 9.22 (1H, s), 8.75 (1H, s), 8.14 (1H, d), 7.99 (1H, d), 7.43 (1H, dd), 7.25-7.17 (1H, m), 7.17-7.10 (1H, m), 6.59 (1H, s), 4.77-4.70 (1H, m), 3.17 (4H, t), 3.06 (6H, s), 2.94 (2H, s), 2.61 (4H, t), 2.44 (2H, s), 1.98 (4H, s), 1.65 (2H, d).

EXAMPLE 33

7-Cyclopentyl-2-(5-{4-[2-(2-hydroxy-ethoxy)-ethyl]-piperazin-1-yl}-pyridin-2-ylamino)-7H-pyrrolo[2,3-d]pyrimidine-6-carboxylic acid dimethylamide

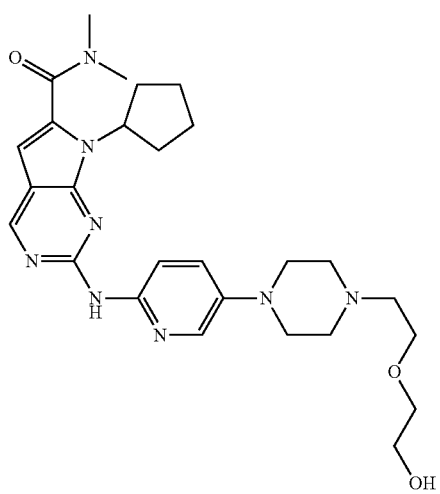 [SMILES: CN(C)C(=O)c1cc2cnc(Nc3ccc(N4CCN(CCOCCO)CC4)cn3)nc2n1C1CCCC1]

To a stirred solution of tert-butyldimethylchlorosilane (50% wt solution in toluene, 8.38 mL, 24.08 mmol) and imidazole (1.78 g, 26.09 mmol) in DMF (10 mL) at 0° C. is added 2-(2-chloroethoxy)ethanol (2.13 mL, 20.07 mmol) dropwise. The reaction mixture is then stirred for 1 h at 0° C. before warming to room temperature and stirring for a further 17 h. The reaction mixture is partitioned between diethyl ether and brine. The combined organics are then dried (MgSO$_4$), filtered and concentrated under reduced pressure to give product (76 mg, 0.318 mmol) which is used directly without further purification.

By repeating procedures described in Example 5, 7-cyclopentyl-2-(5-piperazin-1-yl-pyridin-2-ylamino)-7H-pyrrolo[2,3-d]pyrimidine-6-carboxylic acid dimethylamide hydrochloride (100 mg, 0.212 mmol) gave 7-cyclopentyl-2-(5-{4-[2-(2-hydroxy-ethoxy)-ethyl]-piperazin-1-yl}-pyridin-2-ylamino)-7H-pyrrolo[2,3-d]pyrimidine-6-carboxylic acid dimethylamide as an off white solid (13 mg, 12%). MS (ESI) m/z 523.5 (M+H)+ (method D).

$^1$H NMR (400 MHz, DMSO-$d_6$): 9.22 (1H, s), 8.75 (1H, s), 8.14 (1H, d), 7.99 (1H, d), 7.43 (1H, dd), 6.60 (1H, s), 4.79-4.68 (1H, m), 4.61 (1H, t), 3.57 (2H, t), 3.50 (2H, q), 3.44 (2H, t), 3.15-3.09 (4H, m), 3.06 (6H, s), 2.60 (4H, t), 2.54 (2H, t), 2.48-2.37 (2H, m), 2.05-1.91 (4H, m), 1.71-1.59 (2H, m).

EXAMPLE 88

7-Cyclopentyl-2-{5-[4-(2-dimethylamino-acetyl)-piperazin-1-yl]-pyridin-2-ylamino}-7H-pyrrolo[2,3-d]pyrimidine-6-carboxylic acid dimethylamide

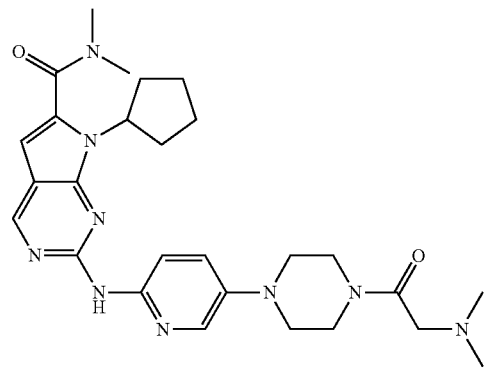 [SMILES: CN(C)CC(=O)N1CCN(c2ccc(Nc3ncc4cc(C(=O)N(C)C)n(C5CCCC5)c4n3)nc2)CC1]

To a solution of 7-cyclopentyl-2-(5-piperazin-1-yl-pyridin-2-ylamino)-7H-pyrrolo[2,3-d]pyrimidine-6-carboxylic acid dimethylamide hydrochloride (80 mg, 0.170 mmol), N,N-dimethylglycine (18 mg, 0.170 mmol) and diisopropylethylamine (0.089 mL, 0.509 mmol) in DMF (1 mL) is added TBTU (55 mg, 0.170 mmol) and the reaction mixture is stirred at room temperature for 1 hour. Methanol (0.5 mL) is added and the reaction mixture purified by silica gel chromatography (gradient of 0-10% 2M NH$_3$ in methanol/dichloromethane) to give 7-cyclopentyl-2-{5-[4-(2-dimethylamino-acetyl)-piperazin-1-yl]-pyridin-2-ylamino}-7H-pyrrolo[2,3-d]pyrimidine-6-carboxylic acid dimethylamide, which is further purified by trituration with acetonitrile, as an off white solid (69 mg, 78%).

MS (ESI) m/z 520.4 (M+H)+ (method D).

$^1$H NMR (400 MHz, Me-$d_3$-OD): 8.75 (1H, s), 8.28-8.21 (1H, m), 8.01 (1H, d), 7.61-7.55 (1H, m), 6.65 (1H, s), 4.83-4.75 (1H, m), 4.22 (2H, s), 3.84 (2H, t), 3.64 (2H, t), 3.28-3.21 (4H, m), 3.18 (6H, s), 2.92 (6H, s), 2.60-2.50 (2H, m), 2.16-2.02 (4H, m), 1.80-1.70 (2H, m).

EXAMPLE 12

2-{5-[4-(2-Amino-acetyl)-piperazin-1-yl]-pyridin-2-ylamino}-7-cyclopentyl-7H-pyrrolo[2,3-d]pyrimidine-6-carboxylic acid dimethylamide

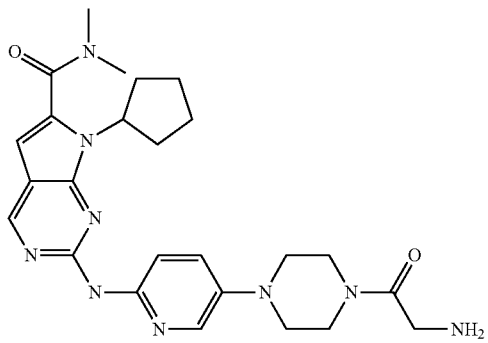 [SMILES: CN(C)C(=O)c1cc2cnc(Nc3ccc(N4CCN(C(=O)CN)CC4)cn3)nc2n1C1CCCC1]

By repeating procedures described in Example 88, 7-cyclopentyl-2-(5-piperazin-1-yl-pyridin-2-ylamino)-7H-pyrrolo[2,3-d]pyrimidine-6-carboxylic acid dimethylamide hydro chloride (150 mg, 0.318 mmol), N-BOC-glycine (56 mg, 0.318 mmol) gave a crude product which is purified by SiO$_2$ chromatography, eluting with 0-7% methanol/dichloromethane to give (2-{4-[6-(7-cyclopentyl-6-dimethylcarbamoyl-7H-pyrrolo[2,3-d]pyrimidin-2-ylamino)-pyridin-3-yl]-piperazin-1-yl}-2-oxo-ethyl)-carbamic acid tert-butyl ester which is used directly in the next step.

Following General Procedure A, (2-{4-[6-(7-cyclopentyl-6-dimethylcarbamoyl-7H-pyrrolo[2,3-d]pyrimidin-2-ylamino)-pyridin-3-yl]-piperazin-1-yl}-2-oxo-ethyl)-carbamic acid tert-butyl ester gave 2-{5-[4-(2-amino-acetyl)-piperazin-1-yl]-pyridine-2-ylamino}-7-cyclopentyl-7H-pyrrolo[2,3-d]pyrimidine-6-carboxylic acid dimethylamide as a pale yellow solid (96 mg, 61%) [following purification by SiO$_2$ chromatography eluting with 0-10% (2M NH$_3$ in methanol/dichloromethane].

MS (ESI) m/z 492.3 (M+H)[1] (method B).

$^1$H NMR (400 MHz, Me-d$_3$-OD): 8.73 (1H, s), 8.28 (1H, d), 8.02 (1H, d), 7.55 (1H, dd), 6.64 (1H, s), 4.82-4.73 (1H, m), 3.97 (2H, s), 3.88-3.78 (2H, m), 3.65 (2H, t), 3.28-3.19 (4H, m), 3.17 (6H, s), 2.55 (2H, d), 2.09 (4H, m), 1.82-1.69 (2H, m).

Benzylic Amine Analogues

General Procedure B (Na(OAc)$_3$BH Reductive Amination)

7-Cyclopentyl-2-(5-formyl-pyridin-2-ylamino)-7H-pyrrolo[2,3-d]pyrimidine-6-carboxylic acid dimethylamide (1 mol. eq.), amine (1.1 mol eq.) are dissolved in dichloromethane (30 vols.) and stirred until the solution is clear (in cases where the amine is sourced as a hydrochloride salt, 1 mol. eq. Et$_3$N is added). Where necessary, MeOH and/or 1 drop acetic acid is added to aid dissolution and imine formation. Na(OAc)$_3$BH (1.5-2 mol. eq.) is then added to the mixture and stirring continued at rt for further 16 h. The reaction is quenched with aqueous NaHCO$_3$ solution and the product extracted with dichloromethane, ethyl acetate or CHCl$_3$/i-PrOH (2:1). The combined organic fractions are dried (Na$_2$SO$_4$ or MgSO$_4$) filtered and the solvent evaporated. The crude product is purified by SiO$_2$ chromatography.

General Procedure C (NaCNBH$_3$ or NaBH$_4$ Reductive Amination)

7-Cyclopentyl-2-(5-formyl-pyridin-2-ylamino)-7H-pyrrolo[2,3-d]pyrimidine-6-carboxylic acid dimethylamide (1 mol. eq.) and amine (1-2 mol. eq.) are dissolved in either dichloroethane/THF (3:1) or MeOH/dichloromethane mixtures (40 vols.). The mixture is stirred at 20-40° C. for 16 hours, then cooled to 0° C., NaCNBH$_3$ or NaBH$_4$ (1.5-2 mol. eq.) are then added and the mixture stirred at rt for 5 h. Where necessary, further MeOH and/or acetic acid is added to aid reaction progress. The mixture is then quenched with aqueous NaHCO$_3$ solution (10 ml) and the product extracted with either diethyl ether, dichloromethane or CHCl$_3$/iPrOH (1:1). The combined organics are dried (MgSO$_4$), filtered and the solvent evaporated. The crude product is purified by SiO$_2$ chromatography.

EXAMPLE C 5-(tert-Butyl-dimethyl-silanyloxymethyl)-pyridin-2-ylamine

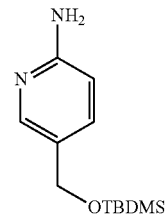

To a solution of (6-chloro-3-pyridinyl) methanol (12.5 g, 87 mmol) and imidazole (7.2 g, 105 mmol) in THF (120 ml) is added a solution of TBDMSCl (15.8 g, 105 mmol) in THF (60 ml). The mixture is stirred at rt for 5 h and then is concentrated in vacuo to ¼ of the original volume. The slurry is then partitioned between water (60 ml) and EtOAc (60 ml). The organic layer is ished once with water, once with a 5% KH$_2$PO$_4$ solution, once with sat. NaHCO$_3$ and finally once with brine. It is then dried (MgSO$_4$), filtered and the solvent evaporated in vacuo. 5-(tert-butyl dimethyl silanyloxymethyl)-2-chloro pyridine is obtained as a colorless liquid (22.4 g, 83%). MS (ESI) m/z 258.0 (M+H)$^+$ 5-(tert-butyl dimethyl silanyloxymethyl)-2-chloro pyridine (5.58 g, 21.6 mmol), BINAP (0.4 g, 0.64 mmol) and benzophenone imine (4.7 g, 25.9 mmol) are dissolved in toluene (50 ml) and the solution is degassed with nitrogen. Sodium t-butoxide (2.91 g, 30.3 mmol) and Pd$_2$(dba)$_3$ (0.2 g, 0.22 mmol) are added and the solution is degassed once more. The mixture is heated at 80° C. for 6 h and then allowed to cool to rt. The mixture is diluted 4-fold with Et$_2$O and then the solution is filtered. Evaporation of solvent in vacuo gave the crude benzhydrylidene-[5-(tert-butyl dimethyl silanyloxymethyl)-pyridin-2-yl]-amine. This product is dissolved in MeOH (50 ml) and hydroxylamine (2.85 ml of a 50% aq. Solution, 46.5 mmol) and the solution stirred at rt for 16 h. The mixture is concentrated in vacuo and then the residue is dissolved in Et$_2$O (50 ml) and filtered. The filtrate is ished with brine, dried (MgSO$_4$) and then the solvent is evaporated in vacuo. The crude red oil is purified by SiO$_2$ chromatography (gradient Petrol Ether:EtOAc=8:1 to 100% EtOAc) to give an orange oil which crystallized when triturated with hexane. The solvent is finally removed in vacuo to give 5-(tert-butyl dimethyl silanyloxymethyl)-pyridin-2-ylamine as an orange solid (2.9 g, 56.1%). MS (ESI) m/z 239.2 (M+H)⁺

EXAMPLE 108

7-Cyclopentyl-2-(5-hydroxymethyl-pyridin-2-ylamino)-7H-pyrrolo[2,3-d]pyrimidine-6-carboxylic acid dimethylamide

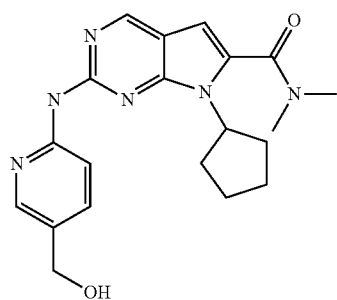

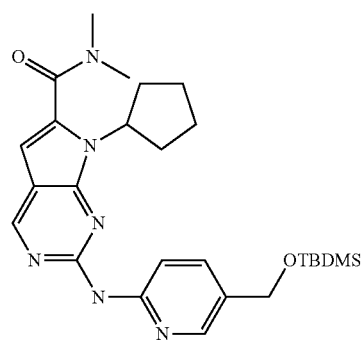

Following Buchwald Method B, 5-(tert-butyl dimethyl silanyloxymethyl)-pyridin-2-ylamine (0.980 g, 4.098 mmol) and 2-chloro-7-cyclopentyl-7H-pyrrolo[2,3-d]pyrimidine-6-carboxylic acid dimethyl amide gave 2-[5-(tert-butyl dimethyl-silanyloxymethyl)-pyridin-2-ylamino]-7-cyclopentyl-7H-pyrrolo[2,3d]pyrimidine-6-carboxylic acid dimethylamide (1.136 g, 84%) [following SiO₂ chromatography eluting with 0-5% MeOH/dichloromethane). MS (ESI) m/z 495.3 (M+H)⁺

2-[5-(tert-butyl dimethyl silanyloxymethyl)-pyridin-2-ylamino]-7-cyclopentyl-7H-pyrrolo[2,3d]pyrimidine-6-carboxylic acid dimethylamide (0.1 g, 0.202 mmol) is dissolved in dry THF (1 ml). TBAF (1M solution in THF) (0.303 ml, 0.303 mmol) is added dropwise, then the mixture stirred for 16 h at rt. The solvent is then evaporated and the crude product is purified by SiO₂ chromatography (eluting with 0-10% MeOH/dichloromethane) to give 7-cyclopentyl-2-(5-hydroxymethyl-pyridin-2-ylamino)-7H-pyrrolo[2,3-d]pyrimidine-6-carboxylic acid dimethylamide (60 mg, 78%). MS (ESI) m/z 381.2 (M+H)⁺ (method B).

¹H NMR (400 MHz, Me-d3-OD): 8.77 (1H, s), 8.45 (1H, d), 8.25 (1H, d), 7.82 (1H, dd), 6.65 (1H, s), 4.81-4.75 (1H, m), 4.62 (2H, s), 3.18 (6H, s), 2.65-2.53 (2H, m), 2.11 (4H, d), 1.84-1.72 (2H, m).

EXAMPLE 107

7-Cyclopentyl-2-(5-formyl-pyridin-2-ylamino)-7H-pyrrolo[2,3-d]pyrimidine-6-carboxylic acid dimethylamide

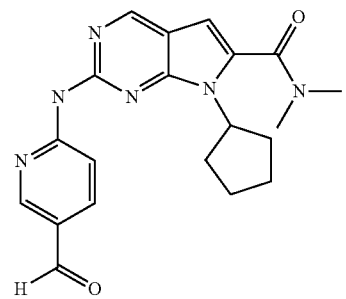 [SMILES: CN(C)C(=O)c1cc2cnc(Nc3ccc(C=O)cn3)nc2n1C1CCCC1]

MnO₂ Method

7-Cyclopentyl-2-(5-hydroxymethyl-pyridin-2-ylamino)-7H-pyrrolo[2,3-d]pyrimidine-6-carboxylic acid dimethylamide (4.49 g, 11.8 mmol) is dissolved in dichloromethane (175 ml) and methanol (75 ml). Activated MnO₂ 85% (51.1 g, 503 mmol) is added in 4 portions over period of 48 h with continual stirring. After a further 16 hours the mixture is filtered. The filtrate is heated to 38° C. and more MnO₂ (24 g, 236 mmol) is added as 2 batches over 5 hours. After stirring for a further 12 hours, the mixture is cooled and filtered. Concentration in vacuo gave a solid which is triturated with MeOH (10 ml) to give 7-cyclopentyl-2-(5-formyl-pyridin-2-ylamino)-7H-pyrrolo[2,3-d]pyrimidine-6-carboxylic acid dimethylamide (3.8 g, 85%). MS (ESI) m/z 379.2 (M+H)⁺ (method B).

¹1-1 NMR (400 MHz, DMSO-d6): 10.47 (1H, s), 9.94 (1H, s), 8.91 (1H, s), 8.82 (1H, d), 8.49 (1H, d), 8.18 (1H, dd), 6.69 (1H, s), 4.83-4.73 (1H, m), 3.06 (6H, s), 2.48-2.38 (2H, m), 2.02 (4H, s), 1.68 (2H, d).

Dess-Martin Periodinane Method

A suspension of Dess-Martin periodinane (0.435 g, 1.06 mmol) in dichloromethane (5 ml) and tert-BuOH (0.1 ml) is stirred at rt. for 15 minutes. To this mixture is added a solution of 7-cyclopentyl-2-(5-hydroxymethyl-pyridin-2-ylamino)-7H-pyrrolo[2,3-d]pyrimidine-6-carboxylic acid dimethylamide (0.3 g, 0.79 mmol) in dichloromethane:THF (5 ml:7 ml) over 5 minutes. The reaction is stirred at rt. for 1 h after which ether (50 ml) and NaOH 1M (25 ml) are added. The mixture stirred vigorously for 10 minutes and then the phases are separated. The aqueous layer is back-extracted with ether (25 ml). The combined organic fractions are ished with water, brine, dried (MgSO₄) filtered and the solvent evaporated to give 7-cyclopentyl-2-(5-formyl-pyridin-2-ylamino)-7H-pyrrolo[2,3-d]pyrimidine-6-carboxylic acid dimethylamide as a white solid (0.244 g, 82%).

EXAMPLE 75

7-Cyclopentyl-2-[5-((3S,5R)-3,5-dimethyl-piperazin-1-ylmethyl)-pyridin-2-ylamino]-7H-pyrrolo[2,3-d]pyrimidine-6-carboxylic acid dimethylamide Following General Procedure B, 7-cyclopentyl-2-(5-formyl-pyridin-2-ylamino)-7H-pyrrolo[2,3-d]pyrimidine-6- carboxylic acid dimethylamide (150 mg, 0.396 mmol) and tert-butyl (2R,6S)-2,6-dimethylpiperazine-1-carboxylate (93 mg, 0.436 mmol) gave (2S,6R)-4-[6-(7-cyclopentyl-6-dimethylcarbamoyl-7H-pyrrolo[2,3-d]pyrimidin-2-ylamino)-pyridin-3-ylmethyl]-2,6-dimethyl-piperazine-1-carboxylic acid tert-butyl ester (170 mg, 74%) [following SiO₂ chromatography, eluting with 0-10% MeOH)/dichloromethane]. MS (ESI) m/z 577.3 (M+H)⁺

Following General Procedure A, (2S,6R)-4-[6-(7-cyclopentyl-6-dimethylcarbamoyl-7H-pyrrolo[2,3-d]pyrimidin-2-ylamino)-pyridin-3-ylmethyl]-2,6-dimethyl-piperazine-1-carboxylic acid tert-butyl ester (170 mg, 0.295 mmol) gave 7-cyclopentyl-2-[5-((3S,5R)-3,5-dimethyl-piperazin-1-ylmethyl)-pyridin-2-ylamino]-7H-pyrrolo[2,3-d]pyrimidine-6-carboxylic acid dimethylamide (128 mg, 91%) [following SiO₂ chromatography, eluting with 0-10% (2M NH₃ in MeOH)/DCM].

MS (ESI) m/z 477.3 (M+H)¹ (method B).

¹H NMR (400 MHz, Me-d₃-OD): 8.78 (1H, s), 8.43 (1H, d), 8.22 (1H, d), 7.79 (1H, dd), 6.66 (1H, s), 4.83-4.75 (1H, m), 3.61 (2H, s), 3.30-3.21 (2H, m), 3.18 (6H, s), 3.01 (2H, d), 2.65-2.52 (2H, m), 2.11 (4H, d), 1.98 (2H, t), 1.84-1.71 (2H, m), 1.24 (6H, d).

EXAMPLE 77

7-Cyclopentyl-2-{5-[4-(2-methoxy-ethyl)-piperazin-1-ylmethyl]-pyridin-2-ylamino}-7H-pyrrolo[2,3-d]pyrimidine-6-carboxylic acid dimethylamide

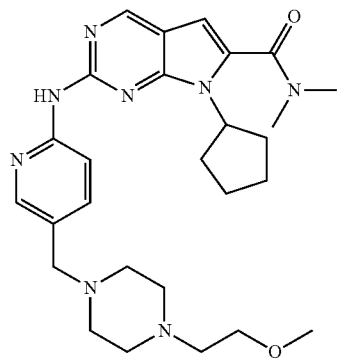 [SMILES: COCCN1CCN(Cc2ccc(Nc3ncc4cc(C(=O)N(C)C)n(C5CCCC5)c4n3)nc2)CC1]

Following General Procedure B, 7-cyclopentyl-2-(5-formyl-pyridin-2-ylamino)-7H-pyrrolo[2,3-d]pyrimidine-6-carboxylic acid dimethylamide (100 mg, 0.264 mmol) and 1-(2-methoxyethyl)piperazine (42 mg, 0.291 mmol) gave 7-cyclopentyl-2-{5-[4-(2-methoxy-ethyl)-piperazin-1-ylmethyl]-pyridin-2-ylamino}-7H-pyrrolo[2,3-d]pyrimidine-6-carboxylic acid dimethylamide (100 mg, 71%) [following SiO₂ chromatography, eluting with 0-10% (2M NH₃ in MeOH)/dichloromethane]. MS (ESI) m/z 507.3 (M+H)⁻ (method A).

¹H NMR (400 MHz, Me-d₃-OD): 8.77 (1H, s), 8.43 (1H, d), 8.21 (1H, d), 7.80 (1H, dd), 6.65 (1H, s), 4.83-4.74 (1H, m), 3.61-3.47 (4H, m), 3.35 (3H, s), 3.18 (6H, s), 2.81-2.41 (12H, m), 2.11 (4H, d), 1.77 (2H, d).

EXAMPLE 62

7-Cyclopentyl-2-[5-(4-isopropyl-piperazin-1-ylmethyl)-pyridin-2-ylamino]-7H-pyrrolo[2,3-d]pyrimidine-6-carboxylic acid dimethylamide

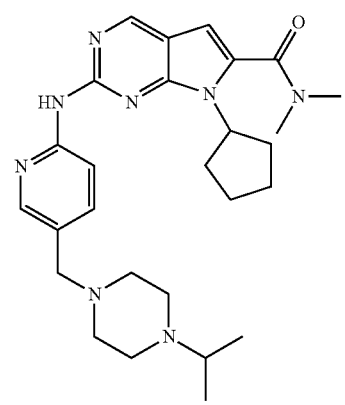 [SMILES: CC(C)N1CCN(Cc2ccc(Nc3ncc4cc(C(=O)N(C)C)n(C5CCCC5)c4n3)nc2)CC1]

Following General Procedure B, 7-cyclopentyl-2-(5-formyl-pyridin-2-ylamino)-7H-pyrrolo[2,3-d]pyrimidine-6-carboxylic acid dimethylamide (150 mg, 0.396 mmol) and N-isopropylpiperazine (56 mg, 0.436 mmol) gave 7-cyclopentyl-2-[5-(4-isopropyl-piperazin-1-ylmethyl)-pyridin-2-ylamino]-7H-pyrrolo[2,3-d]pyrimidine-6-carboxylic acid dimethylamide (103 mg, 53%) [following SiO₂ chromatography, eluting with 0-10% (2M NH₃ in MeOH)/dichloromethane]. MS (ESI) m/z 491.3 (M+H)⁺ (method A).

¹H NMR (400 MHz, Me-d3-OD): 8.78 (1H, s), 8.43 (1H, d), 8.22 (1H, d), 7.80 (1H, dd), 6.65 (1H, s), 4.84-4.77 (1H, m), 3.56 (2H, s), 3.33-3.28 (1H, m), 3.18 (6H, s), 2.78-2.49 (10H, m), 2.11 (4H, d), 1.78 (2H, d), 1.11 (6H, d).

EXAMPLE 85

7-Cyclopentyl-2-{5-[4-(2-hydroxy-ethyl)-piperazin-1-ylmethyl]-pyridin-2-ylamino}-7H-pyrrolo[2,3-d]pyrimidine-6-carboxylic acid dimethylamide

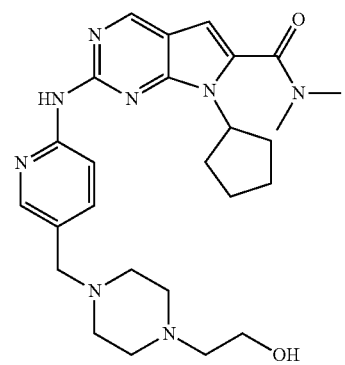 [SMILES: CN(C)C(=O)c1cc2cnc(Nc3ccc(CN4CCN(CCO)CC4)cn3)nc2n1C1CCCC1]

Following General Procedure B, 7-cyclopentyl-2-(5-formyl-pyridin-2-ylamino)-7H-pyrrolo[2,3-d]pyrimidine-6-carboxylic acid dimethylamide (150 mg, 0.396 mmol) and N-(2-hydroxyethyl)piperazine (57 mg, 0.436 mmol) gave 7-cyclopentyl-2-{5-[4-(2-hydroxy-ethyl)-piperazin-1-ylmethyl]-pyridin-2-ylamino}-7H-pyrrolo[2,3-d]pyrimidine-6-carboxylic acid dimethylamide as an off white solid (78 mg, 40%) [following SiO$_2$ chromatography, eluting with 0-10% (2M NH$_3$ in MeOH)/DCM]. MS (ESI) m/z 493.3 (M+H)$^+$ (method A).

$^1$H NMR (400 MHz, Me-d$_3$-OD): 8.77 (1H, s), 8.43 (1H, d), 8.21 (1H, d), 7.80 (1H, dd), 6.65 (1H, s), 4.83-4.74 (1H, m), 3.69 (2H, t), 3.55 (2H, s), 3.18 (6H, s), 2.73-2.47 (12H, m), 2.11 (4H, d), 1.78 (2H, d).

EXAMPLE 34

7-Cyclopentyl-2-[5-(4-methane sulfonyl-piperazin-1-ylmethyl)-pyridin-2-ylamino]-7H-pyrrolo[2,3-d]pyrimidine-6-carboxylic acid dimethylamide

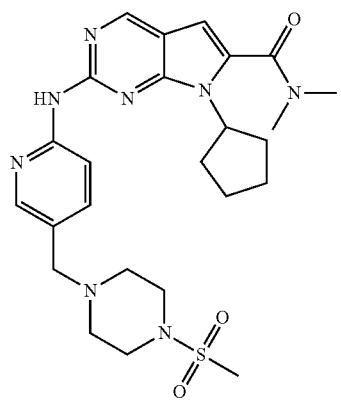 [SMILES: CN(C)C(=O)c1cc2cnc(Nc3ccc(CN4CCN(S(C)(=O)=O)CC4)cn3)nc2n1C1CCCC1]

Following General Procedure B, 7-cyclopentyl-2-(5-formyl-pyridin-2-ylamino)-7H-pyrrolo[2,3-d]pyrimidine-6-carboxylic acid dimethylamide (150 mg, 0.396 mmol) and 1-methanesulfonyl-piperazine (72 mg, 0.436 mmol) gave 7-cyclopentyl-2-[5-(4-methanesulfonyl-piperazin-1-ylmethyl)-pyridin-2-ylamino]-7H-pyrrolo[2,3-d]pyrimidine-6-carboxylic acid dimethylamide as an off white solid (97 mg, 46%) [following SiO$_2$ chromatography, eluting with 0-10% (2M NH$_3$ in MeOH)/DCM].

MS (ESI) m/z 527.2 (M+H)$^+$ (method A).

$^1$-1 NMR (400 MHz, Me-d$_3$-OD): 8.77 (1H, s), 8.43 (1H, d), 8.22 (1H, d), 7.80 (1H, dd), 6.65 (1H, s), 4.80-4.75 (1H, m), 3.60 (2H, s), 3.30-3.25 (4H, m), 3.18 (6H, s), 2.86 (3H, s), 2.66-2.54 (6H, m), 2.11 (4H, d), 1.83-1.72 (2H, m).

EXAMPLE 61

2-[5-(4-Acetyl-piperazin-1-ylmethyl)-pyridin-2-ylamino]-7-cyclopentyl-7H-pyrrolo[2,3-d]pyrimidine-6-carboxylic acid dimethylamide

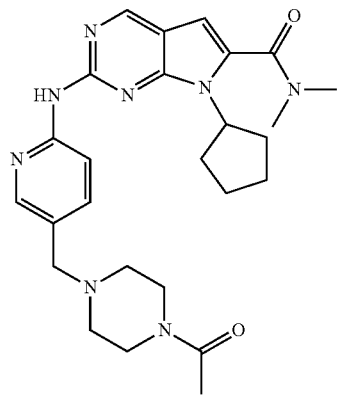 [SMILES: CC(=O)N1CCN(Cc2ccc(Nc3ncc4cc(C(=O)N(C)C)n(C5CCCC5)c4n3)nc2)CC1]

Following General Procedure B, 7-cyclopentyl-2-(5-formyl-pyridin-2-ylamino)-7H-pyrrolo[2,3-d]pyrimidine-6-carboxylic acid dimethylamide (200 mg, 0.528 mmol) and 1-acetyl piperazine (75 mg, 0.581 mmol) gave 2-[5-(4-acetyl-piperazin-1-ylmethyl)-pyridin-2-ylamino]-7-cyclopentyl-7H-pyrrolo[2,3-d]pyrimidine-6-carboxylic acid dimethylamide as an off white solid (96 mg, 37%) [following SiO$_2$ chromatography, eluting with 0-10% (2M NH$_3$ in MeOH)/dichloromethane].

MS (ESI) m/z 491.2 (M+H)$^+$ (method A).

$^1$H NMR (400 MHz, Me-d$_3$-OD): 8.77 (1H, s), 8.43 (1H, d), 8.22 (1H, d), 7.81 (1H, dd), 6.65 (1H, s), 4.84-4.74 (1H, m), 3.63 (2H, t), 3.57 (4H, d), 3.18 (6H, s), 2.65-2.44 (6H, m), 2.19-2.03 (7H, m), 1.78 (2H, d).

EXAMPLE 54

7-Cyclopentyl-2-[5-(3-methyl-piperazin-1-ylmethyl)-pyridin-2-ylamino]-7H-pyrrolo[2,3-d]pyrimidine-6-carboxylic acid dimethylamide

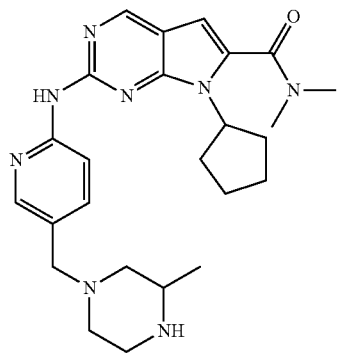 [SMILES: CC1CN(Cc2ccc(Nc3ncc4cc(C(=O)N(C)C)n(C5CCCC5)c4n3)nc2)CCN1]

Following General Procedure C, 7-Cyclopentyl-2-(5-formyl-pyridin-2-ylamino)-7H-pyrrolo[2,3-d]pyrimidine-6-carboxylic acid dimethylamide (0.298 g, 0.788 mmol) and 2-methyl-piperazine-1-carboxylic acid tert-butyl ester (0.316 g, 1.58 mmol) gave 4-[6-(7-cyclopentyl-6-dimethylcarbamoyl-7H-pyrrolo[2,3-d]pyrimidin-2-ylamino)-pyridin-3-ylmethyl]-2-methyl-piperazine-1-carboxylic acid tert-butyl ester a yellowish oil (0.341 g, 77%) [following purification by SiO$_2$ chromatography eluting with 2-6% MeOH/DCM].

MS (ESI) m/z 563.3 (M+H)$^+$

Following General Procedure A, 4-[6-(7-cyclopentyl-6-dimethylcarbamoyl-7H-pyrrolo[2,3-d]pyrimidin-2-ylamino)-pyridin-3-ylmethyl]-2-methyl-piperazine-1-carboxylic acid tert-butyl ester (0.341 g, 0.606 mmol) gave 7-cyclopentyl-2-[5-(3-methyl-piperazin-1-ylmethyl)-pyridin-2-ylamino]-7H-pyrrolo[2,3-d]pyrimidine-6-carboxylic acid dimethylamide as a white solid (70 mg, 25%) [following SiO$_2$ chromatography, eluting with 0-10% (2M NH$_3$ in MeOH)/dichloromethane).

MS (ESI) m/z 463.3 (M+H)$^+$ (method B).

$^1$H NMR (400 MHz, Me-d3-OD): 8.77 (1H, s), 8.42 (1H, d), 8.21 (1H, s), 7.80 (1H, dd), 6.65 (1H, s), 4.82-4.73 (1H, m), 3.54 (2H, s), 3.18 (6H, s), 3.04-2.94 (1H, m), 2.94-2.76 (4H, m), 2.67-2.51 (2H, m), 2.20-2.01 (5H, m), 1.85-1.73 (3H, m), 1.08 (3H, d).

EXAMPLE 10A

7-Cyclopentyl-2-[5-(3-hydroxy-azetidin-1-ylmethyl)-pyridin-2-ylamino]-7H-pyrrolo[2,3-d]pyrimidine-6-carboxylic acid dimethylamide

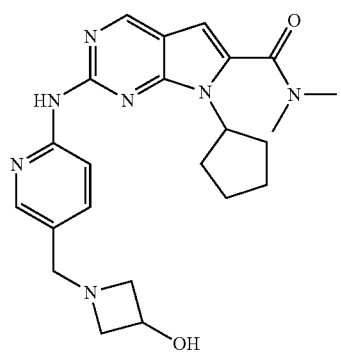 [SMILES: CN(C)C(=O)c1cc2cnc(Nc3ccc(CN4CC(O)C4)cn3)nc2n1C1CCCC1]

Following General Procedure B, 7-cyclopentyl-2-(5-formyl-pyridin-2-ylamino)-7H-pyrrolo[2,3-d]pyrimidine-6-carboxylic acid dimethylamide and 3-hydroxy-azetidinium chloride (73 mg, 0.667 mmol) gave 7-cyclopentyl-2-[5-(3-hydroxy-azetidin-1-ylmethyl)-pyridin-2-ylamino]-7H-pyrrolo[2,3-d]pyrimidine-6-carboxylic acid dimethylamide as a light yellow solid (0.131 g, 47%) [following SiO$_2$ chromatography, eluting with 0-5% (2M NH$_3$ in MeOH)/DCM). MS (ESI) m/z 436.2 (M+H)$^+$ (method B).

$^1$H NMR (400 MHz, CDCl$_3$): 8.78 (1H, s), 8.59-8.41 (2H, m), 8.23 (1H, d), 7.65 (1H, dd), 6.47 (1H, s), 4.88-4.72 (1H, m), 4.55-4.42 (1H, m), 3.84-3.42 (4H, m), 3.17 (6H, s), 3.02 (2H, t), 2.68-2.53 (2H, m), 2.07 (4H, d), 1.73 (2H, d).

EXAMPLE 66

7-Cyclopentyl-2-{5-[((R)-2-hydroxy-1-methyl-ethylamino)-methyl]-pyridin-2 lamino}-7H-pyrrolo[2,3-d]pyrimidine-6-carboxylic acid dimethylamide

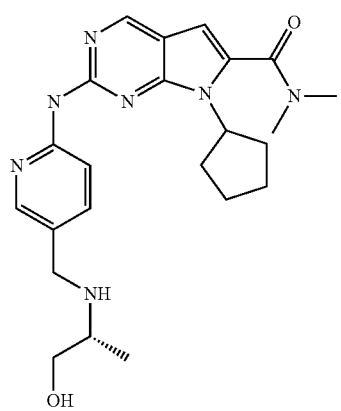 [SMILES: C[C@H](CO)NCc1ccc(Nc2ncc3cc(C(=O)N(C)C)n(C4CCCC4)c3n2)nc1]

Following General Procedure C, 7-Cyclopentyl-2-(5-formyl-pyridin-2-ylamino)-7H-pyrrolo[2,3-d]pyrimidine-6-carboxylic acid dimethylamide (50 mg, 0.132 mmol) and (R)-2-amino propan-1-ol (20 mg, 0.264 mmol) gave 7-cyclopentyl-2-{5-[((R)-2-hydroxy-1-methyl-ethylamino)-methyl]-pyridin-2-yl-amino-7H-pyrrolo[2,3-d]pyrimidine-6-carboxylic acid dimethylamide as a white solid (36 mg, 62%). MS (ESI) m/z 438.3 (M+H)$^+$ (method B).

$^1$H NMR (400 MHz, CDCl$_3$): 8.75 (1H, s), 8.47 (1H, d), 8.28 (1H, d), 7.73 (1H, dd), 6.47 (1H, s), 4.88-4.77 (1H, m), 3.90 (1H, d), 3.77 (1H, d), 3.67 (1H, dd), 3.36 (1H, dd), 3.18 (6H, s), 2.98-2.88 (1H, m), 2.67-2.53 (2H, m), 2.10 (4H, d), 1.75 (2H, d), 1.16 (3H, d).

EXAMPLE 55

7-Cyclopentyl-2-[5-((S)-3-methyl-piperazin-1-ylmethyl)-pyridin-2-ylamino]-7H-pyrrolo[2,3-d]pyrimidine-6-carboxylic acid dimethylamide

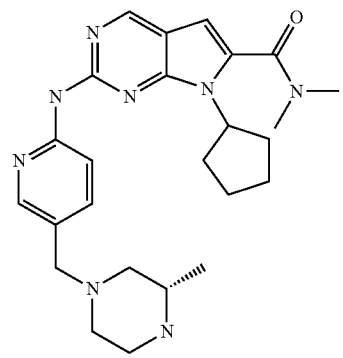 [SMILES: C[C@H]1CN(Cc2ccc(Nc3ncc4cc(C(=O)N(C)C)n(C5CCCC5)c4n3)nc2)CCN1]

Following General Procedure C$_{1-7}$-cyclopentyl-2-(5-formyl-pyridin-2-ylamino)-7H-pyrrolo[2,3-d]pyrimidine-6-carboxylic acid dimethylamide (3.8 g, 10.05 mmol) and (S)-2-methyl-piperazine-1-carboxylic acid tert-butyl ester (5.03 g, 25.13 mmol) gave (S)-4-[6-(7-cyclopentyl-6-dimethylcarbamoyl-7H-pyrrolo[2,3-d]pyrimidin-2-ylamino)-pyridin-3-ylmethyl]-2-methyl-piperazine-1-carboxylic acid tort-butyl ester as a white solid (2.45 g, 45%) [following SiO$_2$ chromatography, eluting with 50% EtOAc/petroleum ether). MS (ESI) m/z 563.3 (M+H)$^+$ Following General Procedure A, (S)-4-[6-(7-cyclopentyl-6-dimethylcarbamoyl-7H-pyrrolo[2,3-d]pyrimidin-2-ylamino)-pyridin-3-ylmethyl]-2-methyl-piperazine-1-carboxylic acid tert-butyl ester (2.45 g, 4.35 mmol) gave 7-cyclopentyl-2-[5-((S)-3-methyl-piperazin-1-ylmethyl)-pyridin-2-ylamino]-7H-pyrrolo[2,3-d]pyrimidine-6-carboxylic acid dimethylamide (1.3 g, 65%) [following SiO$_2$ chromatography, eluting with 5% (NH$_3$ 2.0M in MeOH)/dichloromethane). MS (EST) m/z 463.3 (M+H)$^|$ (method A).

$^1$H NMR (400 MHz, Me-d3-OD): 8.77 (1H, s), 8.42 (1H, d), 8.21 (1H, d), 7.80 (1H, dd), 6.65 (1H, s), 4.83-4.72 (1H, m), 3.54 (2H, s), 3.18 (6H, s), 3.03-2.92 (1H, m), 2.92-2.77 (4H, m), 2.67-2.51 (2H, m), 2.20-2.01 (5H, m), 1.86-1.70 (3H, m), 1.07 (3H, d).

EXAMPLE 76

7-Cyclopentyl-2-[5-(4-hydroxy-piperidin-1-ylmethyl)-pyridin-2-ylamino]-7H-pyrrolo[2,3-d]pyrimidine-6-carboxylic acid dimethylamide

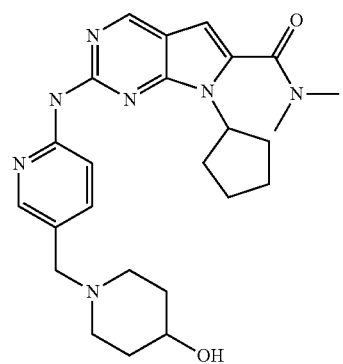 [SMILES: CN(C)C(=O)c1cc2cnc(Nc3ccc(CN4CCC(O)CC4)cn3)nc2n1C1CCCC1]

Following General Procedure B, 7-cyclopentyl-2-(5-formyl-pyridin-2-ylamino)-7H-pyrrolo[2,3-d]pyrimidine-6-carboxylic acid dimethylamide (0.2 g, 0.529 mmol) and piperidin-4-ol (56 mg, 0.556 mmol) gave 7-cyclopentyl-2-[5-(4-hydroxy-piperidin-1-ylmethyl)pyridin-2-ylamino]-7H-pyrrolo[2,3-d]pyrimidine-6-carboxylic acid dimethylamide is obtained as a white solid (25 mg, 10%) [following purification by preparative LCMS and further purification by SiO₂ chromatography, eluting with 0-7% (2N NH₃ in MeOH/EtOAc). MS (ESI) m/z 464.3 (M+H)⁺ (method B).

¹H NMR (400 MHz, Me-d3-OD): 8.77 (1H, s), 8.42 (1H, d), 8.20 (1H, d), 7.80 (1H, dd), 6.65 (1H, s), 4.83-4.72 (1H, m), 3.72-3.60 (1H, m), 3.54 (2H, s), 3.18 (6H, s), 2.83 (2H, d), 2.67-2.50 (2H, m), 2.24 (2H, t), 2.11 (4H, d), 1.89 (2H, d), 1.77 (2H, d), 1.69-1.51 (2H, m).

EXAMPLE 42

7-Cyclopentyl-2-(5-piperazin-1-ylmethyl-pyridin-2-ylamino)-7H-pyrrolo[2,3-d]pyrimidine-6-carboxylic acid dimethylamide

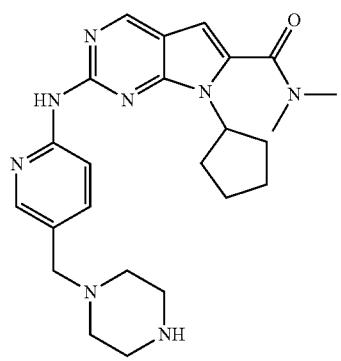 [SMILES: CN(C)C(=O)c1cc2cnc(Nc3ccc(CN4CCNCC4)cn3)nc2n1C1CCCC1]

Following General Procedure B, 7-cyclopentyl-2-(5-formyl-pyridin-2-ylamino)-7H-pyrrolo[2,3-d]pyrimidine-6-carboxylic acid dimethylamide (0.35 g, 0.926 mmol) and piperazine-1-carboxylic acid tert-butyl ester (0.19 g, 1.02 mmol) gave 4-[6-(7-cyclopentyl-6-dimethylcarbamoyl-7H-pyrrolo[2,3-d]pyrimidin-2-ylamino)-pyridin-3-ylmethyl]-piperazine-1-carboxylic acid tert-butyl ester as a white solid (0.333 g, 60%). The material is used directly in the next step. MS (ESI) m/z 549.3 (M+H)⁻

Following General Procedure A, 4-[6-(7-cyclopentyl-6-dimethylcarbamoyl-7H-pyrrolo[2,3-d]pyrimidin-2-ylamino)-pyridin-3-ylmethyl]-piperazine-1-carboxylic acid tert-butyl ester (0.333 g, 0.607 mmol) gave 7-cyclopentyl-2-(5-piperazin-1-ylmethyl-pyridin-2-ylamino)-7H-pyrrolo[2,3-d]pyrimidine-6-carboxylic acid dimethylamide as a white powder (135 mg, 50%) [following treatment with DOWEX 550A and further purification by SiO₂ chromatography, eluting with 0-12% (2N NH₃ in MeOH/dichloromethane). MS (ESI) m/z 449.4 (M+H)⁻ (method D).

¹H NMR (400 MHz, Me-d3-OD): 8.78 (1H, s), 8.43 (1H, d), 8.21 (1H, d), 7.80 (1H, dd), 6.65 (1H, s), 4.83-4.72 (1H, m), 3.54 (2H, s), 3.18 (6H, s), 2.88 (4H, t), 2.79-2.35 (6H, m), 2.11 (4H, d), 1.78 (2H, d).

EXAMPLE 43

7-Cyclopentyl-2-[5-(4-methyl-piperazin-1-ylmethyl)-pyridin-2-ylamino]-7H-pyrrolo[2,3-d]pyrimidine-6-carboxylic acid dimethylamide

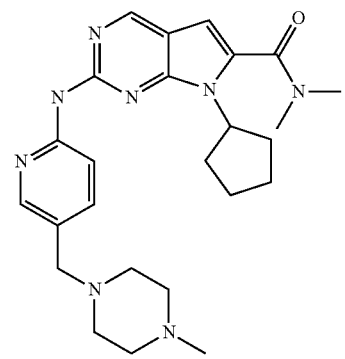 [SMILES: CN1CCN(Cc2ccc(Nc3ncc4cc(C(=O)N(C)C)n(C5CCCC5)c4n3)nc2)CC1]

Following General Procedure B, 7-cyclopentyl-2-(5-formyl-pyridin-2-ylamino)-7H-pyrrolo[2,3-d]pyrimidine-6-carboxylic acid dimethylamide (0.2 g, 0.529 mmol) and N-methyl piperazine (58 mg, 0.582 mmol) gave 7-cyclopentyl-2-[5-(4-methyl-piperazin-1-ylmethyl)-pyridin-2-ylamino]-7H-pyrrolo[2,3-d]pyrimidine-6-carboxylic acid dimethylamide as a white off solid (0.144 g, 60%) [following further purification by SiO₂ chromatography, eluting with 2-5% (2N NH₃ in MeOH/dichloromethane]. MS (ESI) m/z 463.3 (M+H)⁻ (method B).

¹H NMR (400 MHz, Me-d3-OD): 8.78 (1H, s), 8.43 (1H, d), 8.21 (1H, s), 7.79 (1H, dd), 6.65 (1H, s), 4.83-4.72 (1H, m), 3.56 (2H, s), 3.18 (6H, s), 2.98-2.35 (10H, m), 2.30 (3H, s), 2.11 (4H, d), 1.78 (2H, d).

EXAMPLE 73

7-Cyclopentyl-2-[5-(3,8-diaza-bicyclo[3.2.1]oct-3-ylmethyl)-pyridin-2-ylamino]-7H-pyrrolo[2,3-d]pyrimidine-6-carboxylic acid dimethylamide

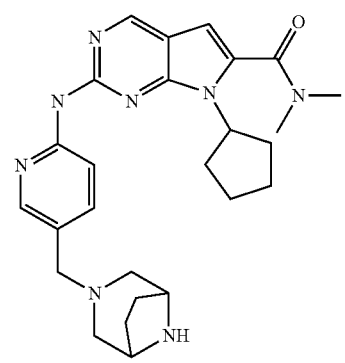 [SMILES: CN(C)C(=O)c1cc2cnc(Nc3ccc(CN4CC5CCC(C4)N5)cn3)nc2n1C1CCCC1]

Following General Procedure B, 7-cyclopentyl-2-(5-formyl-pyridin-2-ylamino)-7H-pyrrolo[2,3-d]pyrimidine-6- carboxylic acid dimethylamide (0.153 g, 0.405 mmol) and 3,8-diaza-bicyclo[3.2.1]octane-8-carboxylic acid tert-butyl ester (95 mg, 0.445 mmol) gave 3-[6-(7-cyclopentyl-6-dimethylcarbamoyl-7H-pyrrolo[2,3-d]pyrimidin-2-ylamino)-pyridin-3-ylmethyl]-3,8-diaza-bicyclo[3.2.1]octane-8-carboxylic acid tert-butyl ester as an off white solid (0.186 g, 80%) [following purification by SiO$_2$ chromatography, eluting with 0-5% MeOH/EtOAc]. MS (ESI) m/z 575.3 (M+H)$^+$ Following General Procedure A, 3-[6-(7-cyclopentyl-6-dimethylcarbamoyl-7H-pyrrolo[2,3-d]pyrimidin-2-ylamino)-pyridin-3-ylmethyl]-3,8-diaza-bicyclo[3.2.1]octane-8-carboxylic acid tert-butyl ester (0.186 g, 0.324 mmol) gave 7-cyclopentyl-2-[5-(3,8-diaza-bicyclo[3.2.1]oct-3-ylmethyl)-pyridin-2-ylamino]-7H-pyrrolo[2,3-d]pyrimidine-6-carboxylic acid dimethylamide as a white solid (0.105 g, 68%) [following purification by SiO$_2$ chromatography, eluting with 0-5% (2M NH$_3$ in MeOH)/dichloromethane]. MS (ESI) m/z 475.3 (M+H) (method B).

$^1$H NMR (400 MHz, Me-d3-OD): 8.77 (1H, s), 8.38 (1H, d), 8.18 (1H, s), 7.76 (1H, dd), 6.65 (1H, s), 4.83-4.72 (1H, m), 3.49 (2H, s), 3.42 (2H, s), 3.18 (6H, s), 2.68 (2H, dd), 2.64-2.50 (2H, m), 2.29 (2H, d), 2.23-2.01 (4H, m), 2.01-1.85 (2H, m), 1.77 (4H, d).

EXAMPLE 65

2-{5-[4-(2-Amino-acetyl)-piperazin-1-ylmethyl]-pyridin-2-ylamino}-7-cyclopentyl-7H-pyrrolo[2,3-d]pyrimidine-6-carboxylic acid dimethylamide

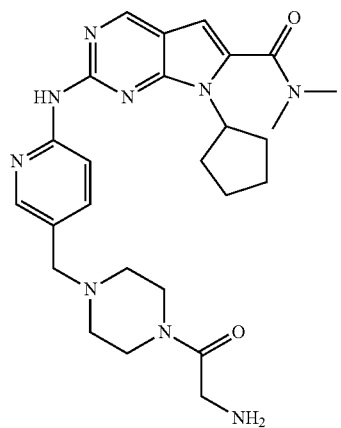 [SMILES: CN(C)C(=O)c1cc2cnc(Nc3ccc(CN4CCN(C(=O)CN)CC4)cn3)nc2n1C1CCCC1]

By repeating procedures outlined in Example 12, 7-cyclopentyl-2-(5-piperazin-1-ylmethyl-pyridin-2-ylamino)-7H-pyrrolo[2,3-d]pyrimidine-6-carboxylic acid dimethylamide (0.108 g, 0.241 mmol) and tert-butoxycarbonylamino-acetic acid (42 mg, 0.241 mmol) gave 2-{5-[4-(2-amino-acetyl)-piperazin-1-ylmethyl]-pyridin-2-ylamino}-7-cyclopentyl-7H-pyrrolo[2,3-d]pyrimidine-6-carboxylic acid dimethylamide as a white solid (87 mg, 69%). MS (ESI) m/z 506.3 (M+H)$^+$ (method B).

$^1$H NMR (400 MHz, Me-d3-OD): 8.78 (1H, s), 8.43 (1H, d), 8.22 (1H, s), 7.80 (1H, dd), 6.65 (1H, s), 4.83-4.72 (1H, m), 3.71-3.62 (2H, m), 3.58 (2H, s), 3.54-3.39 (4H, m), 3.18 (6H, s), 2.67-2.55 (2H, m), 2.55-2.41 (4H, m), 2.20-2.03 (4H, m), 1.86-1.68 (2H, m).

EXAMPLE 60

7-Cyclopentyl-2-[5-(4-methyl-3-oxo-piperazin-1-ylmethyl)-pyridin-2-ylamino]-7H-pyrrolo[2,3-d]pyrimidine-6-carboxylic acid dimethylamide

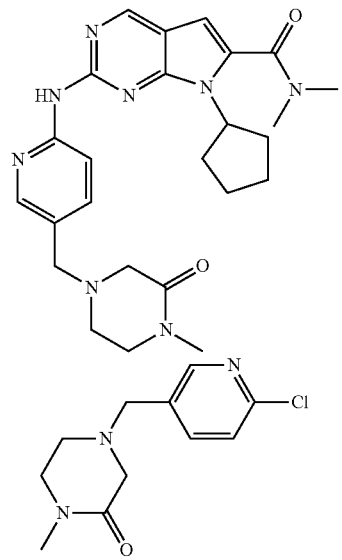

Following General Method B, 6-chloro-pyridine-3-carbaldehyde (500 mg, 3.532 mmol) and 1-methylpiperazine-2-one hydrochloride (559 mg, 3.709 mmol) gave 4-(6-chloro-pyridin-3-ylmethyl)-1-methyl-piperazin-2-one (712 mg, 84%) [following SiO$_2$ chromatography, eluting with 0-10% MeOH/dichloromethane]. MS (ESI) m/z 240.1 (M+H)$^-$

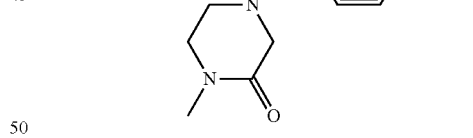

By repeating procedures outlined in Example C step 2 (except that benzhydrylidene intermediate is extracted using EtOAc), 4-(6-chloro-pyridin-3-ylmethyl)-1-methyl-piperazin-2-one (712 mg, 2.970 mmol) gave 4-(6-amino-pyridin-3-ylmethyl)-1-methyl-piperazin-2-one (31 mg, 28%) [following SiO$_2$ chromatography, eluting with 0-10% (2M NH$_3$ in MeOH)/dichloromethane].

MS (ESI) m/z 221.3 (M+H)$^+$

Following Buchwald method B, 4-(6-amino-pyridin-3-ylmethyl)-1-methyl-piperazin-2-one (30 mg, 0.136 mmol) and 2-chloro-7-cyclopentyl-7H-pyrrolo[2,3-d]pyrimidine-6-carboxylic acid dimethylamide (33 mg, 0.113 mmol) give 7-cyclopentyl-2-[5-(4-methyl-3-oxo-piperazin-1-ylmethyl)-pyridin-2-ylamino]-7H-pyrrolo[2,3-d]pyrimidine-6-carboxylic acid dimethylamide (11 mg, 21%) [following SiO$_2$ chromatography eluting with 1-10% (2M NH$_3$ in MeOH)/DCM]

MS (ESI) m/z 477.3 (M+H)[1] (method B)
$^1$H NMR (400 MHz, Me-d₃-OD): 8.78 (1H, s), 8.44 (1H, d), 8.23 (1H, d), 7.81 (1H, dd), 6.65 (1H, s), 4.83-4.76 (1H, m), 3.62 (2H, s), 3.40 (2H, t), 3.19-3.15 (8H, m), 2.97 (3H, s), 2.78 (2H, t), 2.64-2.53 (2H, m), 2.11 (4H, d), 1.77 (2H, d).
Demethylated Amide Series
General Procedure F 2-Chloro-7-cyclopentyl-7H-pyrrolo[2,3-d]pyrimidine-6-carboxylic acid dimethylamide

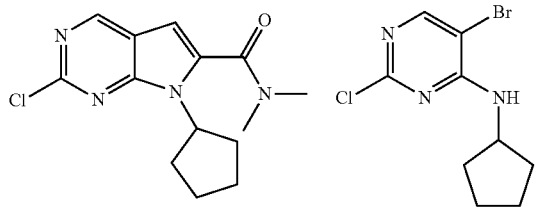

In a large sealed tube is added 5-bromo-2,4-dichloropyrimidine (3 g, 13.2 mmol) in 100 mL of EtOH. Then cyclopentyl amine (1.95 mL, 19.75 mmol) and N,N'-diisopropylethylamine (3.36 mL, 19.8 mmol) are added to the solution at rt. The solution is then stirred rt overnight. Solvent is evaporated and the crude is purified using silica gel chromatography (15% ethyl acetate/85% hexane) to give (5-bromo-2-chloro-pyrimidin-4-yl)-cyclopentyl-amine as a white solid (3.25 g, 89%). MS (ESI) m/z 278.4 (M+H)⁺

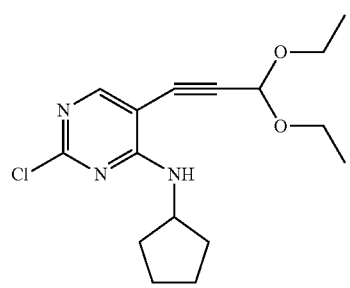 [SMILES: CCOC(C#Cc1cnc(Cl)nc1NC1CCCC1)OCC]

A mixture of (5-bromo-2-chloro-pyrimidin-4-yl)-cyclopentyl amine (1 g, 3.6 mmol), propiolaldehydediethylacetel (550 mg, 4.3 mmol), PdCl₂(PPh₃)₂ (252 mg, 0.36 mmol), CuI (70 mg, 0.36 mmol), 20 mL of Et₃N and 5 mL of DMF is degassed and heated to 100° C. After 13 h, solvent are removed and column is run using 5% ethyl acetate in heptane to 10% ethyl acetate in heptane. Product concentrated to give [2-chloro-5-(3,3-diethoxy-prop-1-ynyl)-pyrimidin-4-yl]-cyclopentyl amine (500 mg, 43%). MS (ESI) m/z 324.5 (M+H)⁺

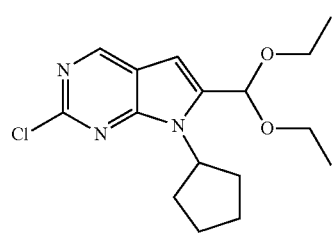 [SMILES: CCOC(OCC)c1cc2cnc(Cl)nc2n1C1CCCC1]

A mixture of [2-chloro-5-(3,3-diethoxy-prop-1-ynyl)-pyrimidin-4-yl]-cyclopentyl amine (5.21 g, 16 mmol) in THF is added 1M tetra-n-butylammonium fluoride in THF (TBAF) (97 mL, 97 mmol) and heated to 65° C. for 2 hour. Solvent is removed and column is run using heptane/ethyl acetate from 5% to 15% to give 2-chloro-7-cyclopentyl-6-diethoxymethyl-7H-pyrrolo[2,3-d]pyrimidine (4.26 g, 82%). MS (ESI) m/z 324.5 (M+H)⁺

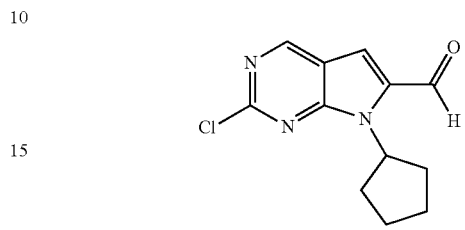

A mixture of 2-chloro-7-cyclopentyl-6-diethoxymethyl-7H-pyrrolo[2,3-d]pyrimidine (4.26 g, 13 mmol) in dioxane is added concentrated HCl. After reaction is completed within 10 min, water is added and then extracted with ethyl acetate. Solvent is removed to give a brown color crude product. Column is run using heptane/ethyl acetate (6:4) to give 2-chloro-7-cyclopentyl-7H-pyrrolo[2,3-d]pyrimidine-6-carbaldehyde (2.69 g, 82%). MS (ESI) m/z 350.4 (M+H)⁺

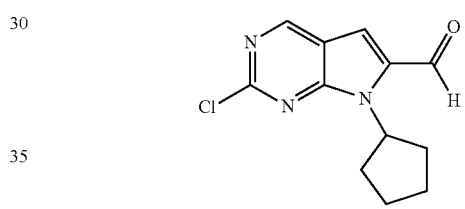

A mixture of 2-chloro-7-cyclopentyl-7H-pyrrolo[2,3-d]pyrimidine-6-carbaldehyde (2.69 g, 11 mmol) in DMF is added oxone (7.2 g, 12 mmol) and stirred for 6 h. After the reaction is complete, water is added and a yellow solid is precipitated to give 2-chloro-7-cyclopentyl-7H-pyrrolo[2,3-d]pyrimidine-6-carboxylic acid (2.69 g, 85%). MS (ESI) m/z 266.4 (M+H)⁺

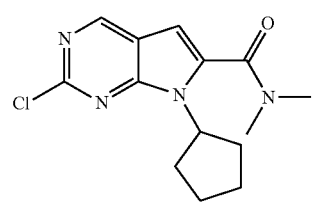 [SMILES: CN(C)C(=O)c1cc2cnc(Cl)nc2n1C1CCCC1]

2-Chloro-7-cyclopentyl-7H-pyrrolo[2,3-d]pyrimidine-6-carboxylic acid (1.07 g, 4.03 mmol), HBTU (1.53 g, 4.03 mmol) and diisopropylethylamine (2 mL, 12.1 mmol) are dissolves in dimethylformamide (20 mL). 2 M solution of dimethylamine in ethanol (2.4 mL, 4.8 mmol) is added and the mixture is stirred for 30 minutes to achieve complete conversion. The reaction mixture is diluted with ethyl acetate and washed with saturated aqueous sodium hydrogen carbonate, water, then brine. The organic phase is dried (Na₂SO₄), filtered and concentrated. Purification by chromatography on silicagel (ethyl acetate:heptane) provides 2-Chloro-7-cyclopentyl-7H-pyrrolo[2,3-d]pyrimidine-6-carboxylic acid dimethylamide (927 mg, 79% yield) MS (ESI) m/z 293.1 (M+H)+

EXAMPLE 1

7-Cyclopentyl-2-(pyridin-2-ylamino)-7H-pyrrolo[2,3-d]pyrimidine-6-carboxylic acid dimethylamide

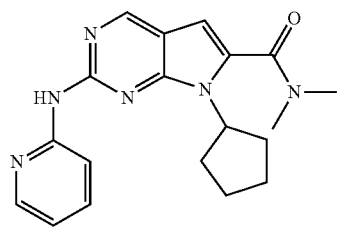 [SMILES: CN(C)C(=O)c1cc2cnc(Nc3ccccn3)nc2n1C1CCCC1]

Following Buchwald Method B, 2-chloro-7-cyclopentyl-7H-pyrrolo[2,3-d]pyrimidine-6-carboxylic acid dimethylamide (100 mg, 0.34 mmol) and pyridine-2-ylamine (64 mg, 0.68 mmol) gave 7-cyclopentyl-2-(pyridin-2-ylamino)-7H-pyrrolo[2,3-d]pyrimidine-6-carboxylic acid dimethylamide (350 mg, 84%).

MS (ESI) m/z 351.1 (M+H)+

EXAMPLE 74

7-Cyclopentyl-2-(5-piperazin-1-yl-pyridin-2-ylamino)-7H-pyrrolo[2,3-d]pyrimidine-6-carboxylic acid dimethylamide

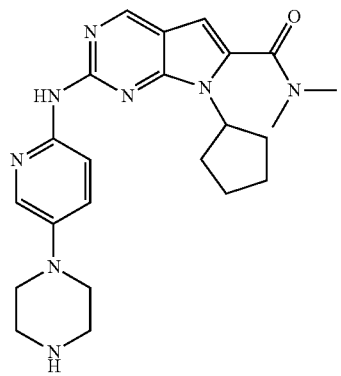 [SMILES: CN(C)C(=O)c1cc2cnc(Nc3ccc(N4CCNCC4)cn3)nc2n1C1CCCC1]

Following Buchwald Method B, then General Procedure A, 2-chloro-7-cyclopentyl-7H-pyrrolo[2,3-d]pyrimidine-6-carboxylic acid dimethylamide (300 mg, 1.02 mmol) and 5-piperazin-1-yl-pyridin-2-ylamine (314 mg, 1.13 mmol) gave 7-cyclopentyl-2-(5-piperazin-1-yl-pyridin-2-ylamino)-7H-pyrrolo[2,3-d]pyrimidine-6-carboxylic acid dimethylamide (142 mg, 36%). MS (EST) m/z 435.3 (M+H)+

Alkylated Analogues
General Procedure D

EXAMPLE 78

7-Cyclopentyl-2-[5-(4-ethyl-piperazin-1-yl)-pyridin-2-ylamino]-7H-pyrrolo[2,3d]pyrimidine-6-carboxylic acid dimethylamide

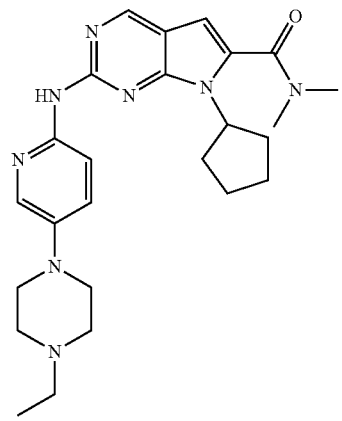 [SMILES: CCN1CCN(c2ccc(Nc3ncc4cc(C(=O)N(C)C)n(C5CCCC5)c4n3)nc2)CC1]

To a solution of 7-cyclopentyl-2-(5-piperazin-1-yl-pyridin-2-ylamino)-7H-pyrrolo[2,3-d]pyrimidine-6-carboxylic acid dimethylamide (100 mg, 0.229 mmol) in 20 mL of THF is added potassium carbonate (100 mg, 0.689 mmol) then bromoethane (75 mg, 0.687 mmol). The reaction mixture is heated at 70° C. for 18 h. Following SiO2 chromatography, eluting with 0-10% (2M NH3 in MeOH)/dichloromethan] gave 7-cyclopentyl-2-[5-(4-ethyl-piperazin-1-yl)-pyridin-2-ylamino]-7H pyrrolo[2,3d]pyrimidine-6-carboxylic acid dimethylamide (67 mg, 63%). MS (ESI) m/z 463.3 (M+H)+

EXAMPLE 86

7-Cyclopentyl-2-{5-[4-(2-fluoro-ethyl)-piperazin-1-yl]-pyridin-2-ylamino}-7H-pyrrolo[2,3-d]pyrimidine-6-carboxylic acid dimethylamide

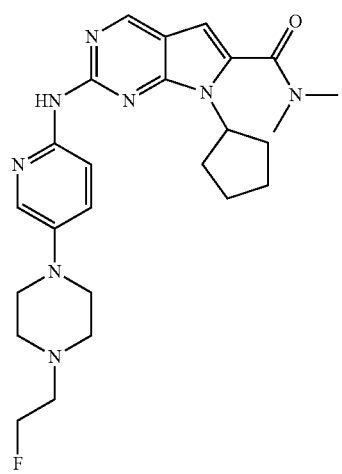 [SMILES: CN(C)C(=O)c1cc2cnc(Nc3ccc(N4CCN(CCF)CC4)cn3)nc2n1C1CCCC1]

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.229 mmol) and 1-bromo-2-fluoroethane (88 mg, 0.687 mmol) gave 7-cyclopentyl-2-{5-[4-(2-fluoro-ethyl)-piperazin-1-yl]-pyridin-2-ylamino}-7H-pyrrolo[2,3-d]pyrimidine-6-carboxylic acid dimethylamide (51 mg, 80%).
MS (ESI) m/z 481.3 (M+H)+

EXAMPLE 26

7-Cyclopentyl-2-{5-[4-(2-hydroxy-ethyl)-piperazin-1-yl]-pyridin-2-ylamino}-7H-pyrrolo[2,3-d]pyrimidine-6-carboxylic acid dimethylamide

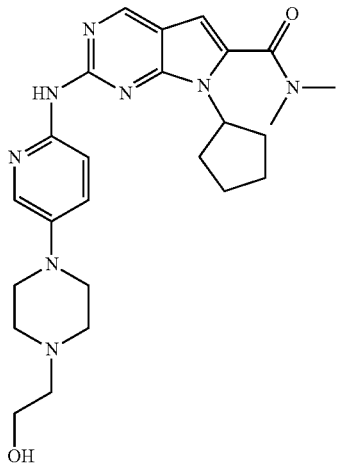

Following General Procedure D, 7-cyclopentyl-2-(5-piperazin-1-yl-pyridin-2-ylamino)-7H-pyrrolo[2,3-d]pyrimidine-6-carboxylic acid dimethylamide (34 mg, 0.072 mmol) and 2-bromo ethanol (9 mg, 0.216 mmol) gave 7-cyclopentyl-2-{5-[4-(2-hydroxy-ethyl)-piperazin-1-yl]-pyridin-2-ylamino}-7H-pyrrolo[2,3-d]pyrimidine-6-carboxylic acid dimethylamide (12 mg, 32%). MS (ESI) m/z 479.3 (M+H)+

EXAMPLE 95

7-Cyclopentyl-2-{5-[4-(2-isopropoxy-ethyl)-piperazin-1-yl]-pyridin-2-ylamino}-7H-pyrrolo[2,3-d]pyrimidine-6-carboxylic acid dimethylamide

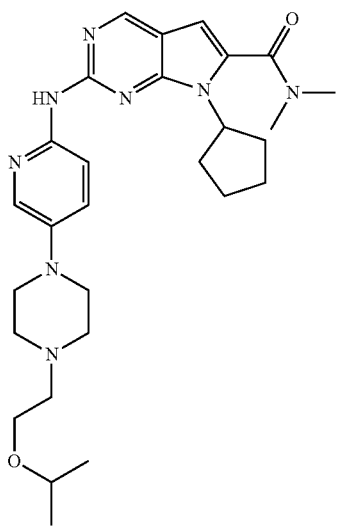 [SMILES: CC(C)OCCN1CCN(c2ccc(Nc3ncc4cc(C(=O)N(C)C)n(C5CCCC5)c4n3)nc2)CC1]

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.229 mmol) and 2-(2-bromoethoxy)propane (200 mg, 0.252 mmol) gave 7-cyclopentyl-2-{5-[4-(2-isopropoxy-ethyl)-piperazin-1-yl]-pyridin-2-ylamino}-7H-pyrrolo[2,3-d]pyrimidine-6-carboxylic acid dimethylamide (103 mg, 86%). MS (ESI) m/z 521.3 (M+H)¹

General Procedure E

EXAMPLE 57

7-Cyclopentyl-2-{5-[4-((R)-2-hydroxy-propyl)-piperazin-1-yl]-pyridin-2-ylamino}-7H-pyrrolo[2,3-d]pyrimidine-6-carboxylic acid dimethylamide

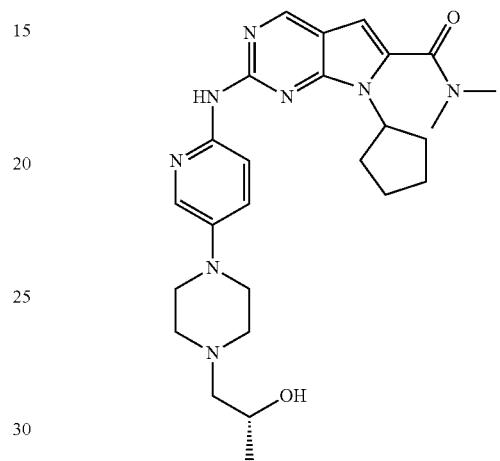

To a solution of 7-cyclopentyl-2-(5-piperazin-1-yl-pyridin-2-ylamino)-7H-pyrrolo[2,3-d]pyrimidine-6-carboxylic acid dimethylamide (55 mg, 0.123 mmol) and (R)-2-methyl-oxirane (250 mg, 4.3 mmol) in 5 mL of ethanol is heated at 70° C. for 18 h. Following SiO$_2$ chromatography, eluting with 0-10% (2M NH$_3$ in MeOH)/dichloromethane] gave 7-cyclopentyl-2-{5-[4-((R)-2-hydroxy-propyl)-piperazin-1-yl]-pyridin-2-ylamino}-7H-pyrrolo[2,3-d]pyrimidine-6-carboxylic acid dimethylamide (10 mg, 16%). MS (ESI) m/z 493.3 (M+H)+

¹H NMR (400 MHz, CDCl$_3$): 8.70 (1H, s), 8.32 (1H, d), 7.96 (1H, s), 7.80 (1H, s), 7.28 (1H, d), 6.45 (1H, s), 5.32 (1H, s), 4.86-4.77 (1H, s), 3.85 (2H, t), 3.44 (2H, t), 3.18 (6H, s), 2.98 (3H, s), 2.62-2.59 (2H, m), 2.11-2.02 (3H, m); 1.74-1.63 (3H, m).

EXAMPLE 56

7-Cyclopentyl-2-{5-[4-((S)-2-hydroxy-propyl)-piperazin-1-yl]-pyridin-2-ylamino}-7H-pyrrolo[2,3-d]pyrimidine-6-carboxylic acid dimethylamide

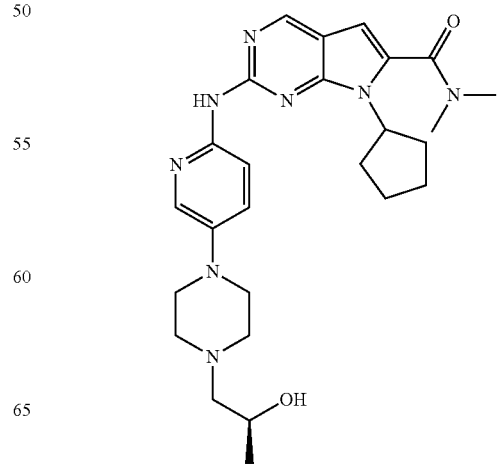

Following General Procedure E, 7-cyclopentyl-2-(5-piperazin-1-yl-pyridin-2-ylamino)-7H-pyrrolo[2,3-d]pyrimidine-6-carboxylic acid dimethylamide (48 mg, 0.110 mmol) and (S)-2-methyl oxirane (121 mg, 0.22 mmol) gave 7-cyclopentyl-2-{5-[4-((S)-2-hydroxy-propyl)-piperazin-1-yl]-pyridin-2-ylamino}-7H-pyrrolo[2,3-d]pyrimidine-6-carboxylic acid dimethylamide (10 mg, 16%).
MS (ESI) m/z 493.3 (M+H)⁺

EXAMPLE 71

7-Cyclopentyl-2-{5-[4-(2-hydroxy-2-methyl-propyl)-piperazin-1-yl]-pyridin-2-ylamino}-7H-pyrrolo[2,3-d]pyrimidine-6-carboxylic acid dimethylamide

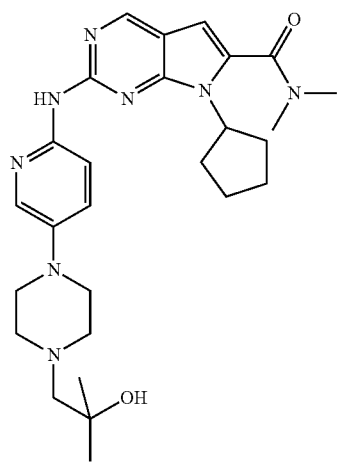 [SMILES: CN(C)C(=O)c1cc2cnc(Nc3ccc(N4CCN(CC(C)(C)O)CC4)cn3)nc2n1C1CCCC1]

Following General Procedure E, 7-cyclopentyl-2-(5-piperazin-1-yl-pyridin-2-ylamino)-7H-pyrrolo[2,3-d]pyrimidine-6-carboxylic acid dimethylamide (50 mg, 0.115 mmol) and 2,2-dimethyloxirane (72 mg, 0.805 mmol) gave 7-cyclopentyl-2-{5-[4-(2-hydroxy-2-methyl-propyl)-piperazin-1-yl]-pyridin-2-ylamino}-7H-pyrrolo[2,3-d]pyrimidine-6-carboxylic acid dimethylamide (17 mg, 29%). MS (ESI) m/z 507.3 (M+H)⁺

EXAMPLE 21

7-Cyclopentyl-2-{5-[4-(3-hydroxy-propyl)-piperazin-1-yl]-pyridin-2-ylamino}-7H-pyrrolo[2,3-d]pyrimidine-6-carboxylic acid dimethylamide

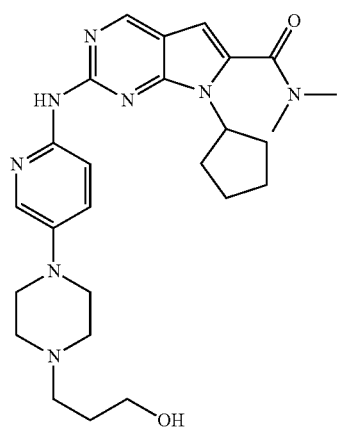 [SMILES: CN(C)C(=O)c1cc2cnc(Nc3ccc(N4CCN(CCCO)CC4)cn3)nc2n1C1CCCC1]

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.229 mmol) and 3-bromo propan-1-ol (80 mg, 0.574 mmol) gave 7-cyclopentyl-2-{5-[4-(2-hydroxy-2-methylpropyl)-piperazin-1-yl]-pyridin-2-ylamino}-7H-pyrrolo[2,3-d]pyrimidine-6-carboxylic acid dimethylamide (55 mg, 50%). MS (ESI) m/z 493.3 (M+H)⁺

EXAMPLE 44

7-Cyclopentyl-2-{5-[4-(3-hydroxy-propyl)-piperazin-1-yl]-pyridin-2-ylamino}-7H-pyrrolo[2,3-d]pyrimidine-6-carboxylic acid dimethylamide

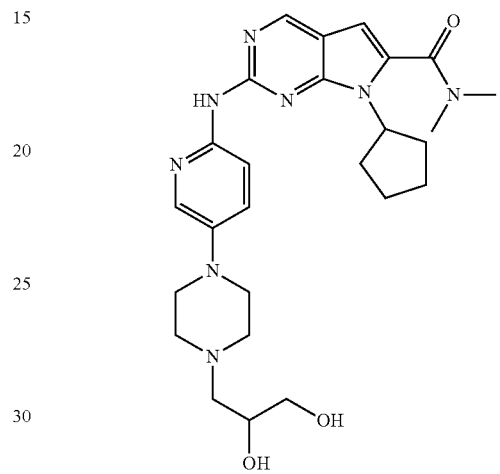

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.229 mmol) and 3-bromo propane-1,2-diol (106 mg, 0.687 mmol) gave 7-cyclopentyl-2-{5-[4-(2-hydroxy-2-methyl-propyl)-piperazin-1-yl]-pyridin-2-ylamino}-7H-pyrrolo[2,3-d]pyrimidine-6-carboxylic acid dim ethyl amide (29 mg, 24%). MS (ESI) m/z 509.3 (M+H)⁺

EXAMPLE 46

7-Cyclopentyl-2-{5-[4-((R)-2,3-dihydroxy-propyl)-piperazin-1-yl]-pyridin-2-ylamino}-7H-pyrrolo[2,3-d]pyrimidine-6-carboxylic acid dimethylamide

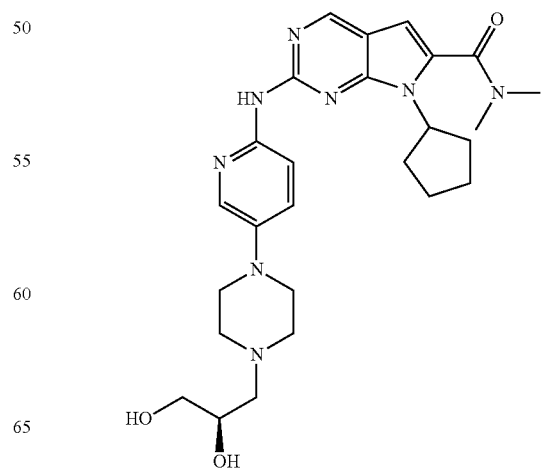

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and R-(+)glycidol (51 mg, 0.691 mmol) gave 7-cyclopentyl-2-{5-[4-((R)-2,3-dihydroxy-propyl)-piperazin-1-yl]-pyridin-2-ylamino}-7H-pyrrolo[2,3-d]pyrimidine-6-carboxylic acid dimethylamide (56 mg, 47%). MS (ESI) m/z 509.3 (M+H)+

EXAMPLE 29

7-Cyclopentyl-2-{5-[4-((S)-2,3-dihydroxy-propyl)-piperazin-1-yl]-pyridin-2-ylamino}-7H-pyrrolo[2,3-d]pyrimidine-6-carboxylic acid dimethylamide

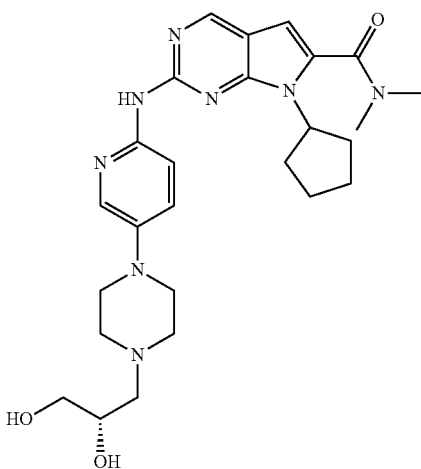 [SMILES: CN(C)C(=O)c1cc2cnc(Nc3ccc(N4CCN(C[C@H](O)CO)CC4)cn3)nc2n1C1CCCC1]

Following General Procedure E, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and (S)-(+)glycidol (51 mg, 0.691 mmol) gave 7-cyclopentyl-2-{5-[4-((S)-2,3-dihydroxy-propyl)-piperazin-1-yl]-pyridin-2-ylamino}-7H-pyrrolo[2,3-d]pyrimidine-6-carboxylic acid dimethylamide (60 mg, 50%). MS (ESI) m/z 509.3 (M+H)+

EXAMPLE 79

7-Cyclopentyl-2-[5-(4-cyclopentyl-piperazin-1-yl)-pyridin-2-ylamino]-7H-pyrrolo[2,3-d]pyrimidine-6-carboxylic acid dimethylamide

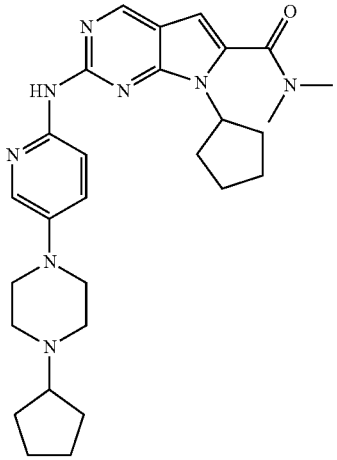 [SMILES: CN(C)C(=O)c1cc2cnc(Nc3ccc(N4CCN(C5CCCC5)CC4)cn3)nc2n1C1CCCC1]

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and bromo cyclopentane (103 mg, 0.691 mmol) gave 7-cyclopentyl-2-[5-(4-cyclopentyl-piperazin-1-yl)-pyridin-2-ylamino]-7H-pyrrolo[2,3-d]pyrimidine-6-carboxylic acid dimethylamide (85 mg, 71%). MS (ESI) m/z 503.3 (M+H)+

EXAMPLE 63

7-Cyclopentyl-2-[5-(4-isopropyl-piperazin-1-yl)-pyridin-2-ylamino]-7H-pyrrolo[2,3-d]pyrimidine-6-carboxylic acid dimethylamide

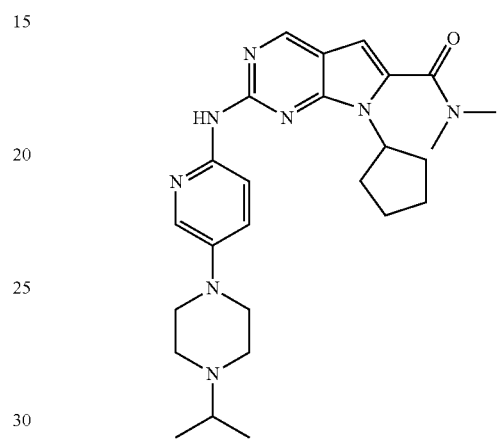

To a solution of 7-cyclopentyl-2-(5-piperazin-1-yl-pyridin-2-ylamino)-7H-pyrrolo[2,3-d]pyrimidine-6-carboxylic acid dimethylamide (30 mg, 0.069 mmol) in 10 mL of dichloromethane is added 1 mL of acetone and NaB(OAc)$_3$H (30 mg, 0.138 mmol). The resulting mixture is stirred at room temperature for 18 h. Following purification by preparative LCMS gave 7-cyclopentyl-2-[5-(4-isopropyl-piperazin-1-yl)-pyridin-2-ylamino]-7H-pyrrolo[2,3-d]pyrimidine-6-carboxylic acid dimethylamide (20 mg, 61%). MS (ESI) m/z 477.3 (M+H)¹

EXAMPLE 36

7-Cyclopentyl-2-{5-[4-(2-hydroxy-1-methyl-ethyl)-piperazin-1-yl]-pyridin-2-ylamino}-7H-pyrrolo[2,3-d]pyrimidine-6-carboxylic acid dimethylamide

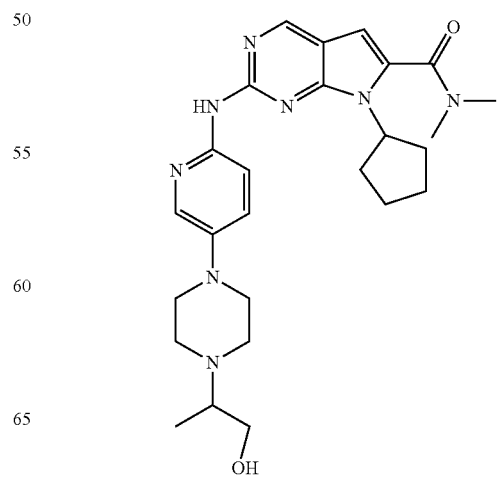

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and 2-bromo propan-1-ol (96 mg, 0.690 mmol) gave 7-cyclopentyl-2-{5-[4-(2-hydroxy-1-methyl-ethyl)-piperazin-1-yl]-pyridin-2-ylamino}-7H-pyrrolo[2,3-d]pyrimidine-6-carboxylic acid dimethylamide (28 mg, 25%). MS (ESI) m/z 493.4 (M+H)⁺

EXAMPLE 101

2-{4-[6-(7-Cyclopentyl-6-dimethylcarbamoyl-7H-pyrrolo[2,3-d]pyrimidin-2-ylamino)-pyridin-3-yl]-piperazin-1-yl}-propionic acid methyl ester

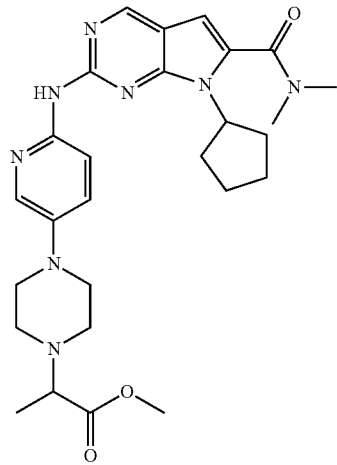 [SMILES: COC(=O)C(C)N1CCN(c2ccc(Nc3ncc4cc(C(=O)N(C)C)n(C5CCCC5)c4n3)nc2)CC1]

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and 2-bromo propionic acid methyl ester (31 mL, 0.28 mmol) gave 2-{4-[6-(7-cyclopentyl-6-dimethylcarbamoyl-7H-pyrrolo[2,3-d]pyrimidin-2-ylamino)-pyridin-3-yl]-piperazin-1-yl}-propionic acid methyl ester (46 mg, 39%). MS (ESI) m/z 521.4 (M+H)⁺

EXAMPLE 103

2-{4-[6-(7-Cyclopentyl-6-dimethylcarbamoyl-7H-pyrrolo[2,3-d]pyrimidin-2-ylamino)-pyridin-3-yl]-piperazin-1-yl}-propionic acid

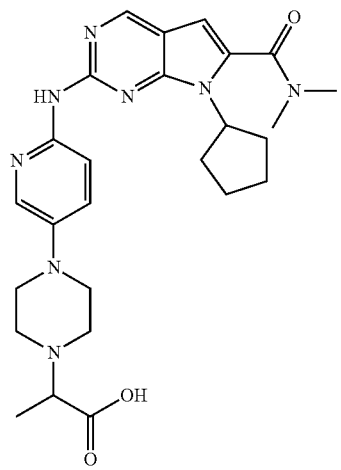 [SMILES: CC(C(=O)O)N1CCN(c2ccc(Nc3ncc4cc(C(=O)N(C)C)n(C5CCCC5)c4n3)nc2)CC1]

To a solution of 2-{4-[6-(7-cyclopentyl-6-dimethylcarbamoyl-7H-pyrrolo[2,3-d]pyrimidin-2-ylamino)-pyridin-3-yl]-piperazin-1-yl}-propionic acid methyl ester (250 mg, 0.48 mmol) in 10 mL of THF is added a solution of LiOH (19 mg, 48 mmol) in 10 mL of H₂O. After 18 h stirring at room temperature, the resulting mixture is concentrated and diluted with H₂O and adjusted to pH=6 with 1 N HCl. Ished with dichloromethane then solids precipitated and collected to give 2-{4-[6-(7-cyclopentyl-6-dimethylcarbamoyl-7H-pyrrolo[2,3-d]pyrimidin-2-ylamino)-pyridin-3-yl]-piperazin-1-yl}-propionic acid (225 mg, 94%). MS (EST) m/z 507.3 (M+H)⁺

EXAMPLE 69

2-[5-(4-Cyclohexylmethyl-piperazin-1-yl)-pyridin-2-ylamino]-7-cyclopentyl-7H-pyrrolo[2,3-d]pyrimidine-6-carboxylic acid dimethylamide

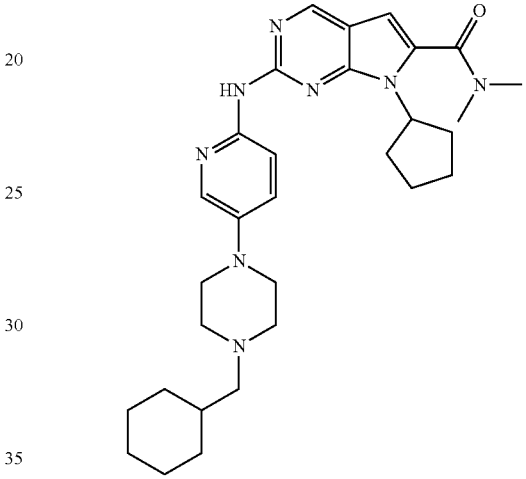

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and bromomethyl cyclohexane (122 mg, 0.690 mmol) gave 2-[5-(4-cyclohexylmethyl-piperazin-1-yl)-pyridin-2-ylamino]-7-cyclopentyl-7H-pyrrolo[2,3-d]pyrimidine-6-carboxylic acid dimethylamide (75 mg, 63%). MS (ESI) m/z 531.4 (M+H)⁺

EXAMPLE 92

7-Cyclopentyl-2-[5-(4-isobutyl-piperazin-1-yl)-pyridin-2-ylamino]-7H-pyrrolo[2,3-d]pyrimidine-6-carboxylic acid dimethylamide

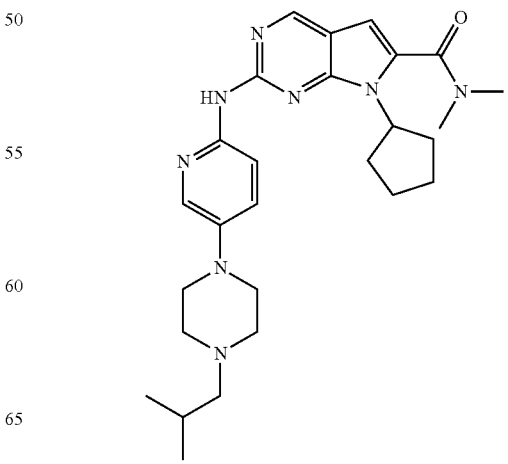

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and 1-bromo-2-methyl propane (94 mg, 0.690 mmol) gave 7-cyclopentyl-2-[5-(4-isobutyl-piperazin-1-yl)-pyridin-2-ylamino]-7H-pyrrolo[2,3-d]pyrimidine-6-carboxylic acid dimethylamide (45 mg, 41%). MS (ESI) m/z 491.3 (M+H)+

EXAMPLE 99

7-Cyclopentyl-2-{5-[4-(2-methyl-butyl)-piperazin-1-yl]-pyridin-2-ylamino}-7H-pyrrolo[2,3-d]pyrimidine-6-carboxylic acid dimethylamide

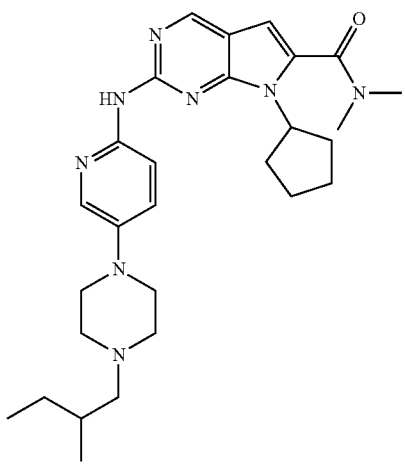 [SMILES: CCC(C)CN1CCN(c2ccc(Nc3ncc4cc(C(=O)N(C)C)n(C5CCCC5)c4n3)nc2)CC1]

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and 1-bromo-2-methyl butane (103 mg, 0.690 mmol) gave 7-cyclopentyl-2-{5-[4-(2-methyl-butyl)-piperazin-1-yl]-pyridin-2-ylamino}-7H-pyrrolo[2,3-d]pyrimidine-6-carboxylic acid dimethylamide (50 mg, 42%).
MS (ESI) m/z 505.3 (M+H)

EXAMPLE 68

7-Cyclopentyl-2-{5-[4-(4-methyl-pentyl)-piperazin-1-yl]-pyridin-2-ylamino}-7H-pyrrolo[2,3-d]pyrimidine-6-carboxylic acid dimethylamide

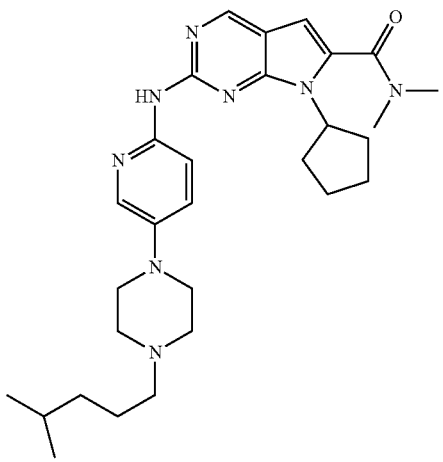 [SMILES: CC(C)CCCN1CCN(c2ccc(Nc3ncc4cc(C(=O)N(C)C)n(C5CCCC5)c4n3)nc2)CC1]

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and 1-bromo-4-methyl pentane (103 mg, 0.690 mmol) gave 7-cyclopentyl-2-{5-[4-(4-methyl-pentyl)-piperazin-1-yl]-pyridin-2-ylamino}-7H-pyrrolo[2,3-d]pyrimidine-6-carboxylic acid dimethylamide (50 mg, 42%). MS (ESI) m/z 519.4 (M+H)+

EXAMPLE 10

2-[5-(4-Carbamoylmethyl-piperazin-1-yl)-pyridin-2-ylamino]-7-cyclopentyl-7H-pyrrolo[2,3-d]pyrimidine-6-carboxylic acid dimethylamide

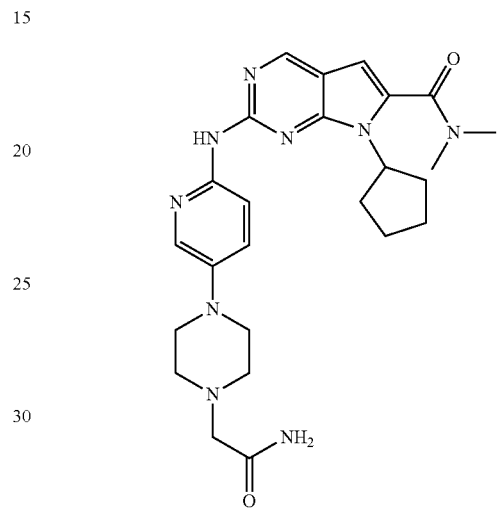

Following General Procedure D, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and 2-bromo acetamide (95 mg, 0.690 mmol) gave 2-[5-(4-carbamoylmethyl piperazin-1-yl)-pyridin-2-ylamino]-7-cyclopentyl-7H-pyrrolo[2,3-d]pyrimidine-6-carboxylic acid dimethylamide (50 mg, 45%).
MS (ESI) m/z 492.4 (M+H)+

EXAMPLE 7

2-[5-(4-Acetyl piperazin-1-yl)-pyridin-2-ylamino]-7-cyclopentyl-7H-pyrrolo[2,3-d]pyrimidine-6-carboxylic acid dimethylamide

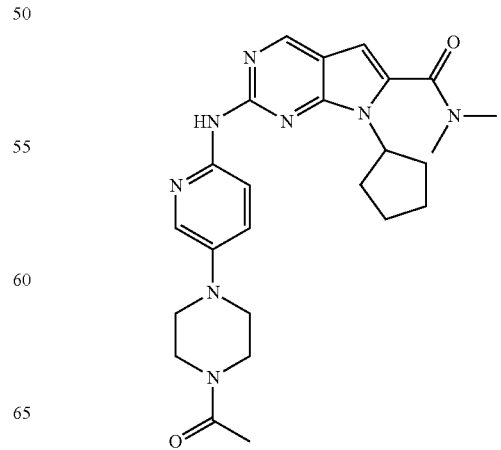

7-cyclopentyl-2-(5-piperazin-1-yl-pyridin-2-ylamino)-7H-pyrrolo[2,3-d]pyrimidine-6-carboxylic acid dimethylamide (30 mg, 0.230 mmol) in 5 mL of dichloromethane. Added 0.5 mL of acetic anhydride. After 10 min, reaction is complete and trituration with acetonitrile gave 2-[5-(4-acetyl-piperazin-1-yl)-pyridin-2-ylamino]-7-cyclopentyl-7H-pyrrolo[2,3-d]pyrimidine-6-carboxylic acid dimethylamide (30 mg, 91%). MS (ESI) m/z 477.3 (M+H)

General Procedure G

EXAMPLE 27

7-Cyclopentyl-2-[5-(4-cyclopropanecarbonyl-piperazin-1-yl)-pyridin-2-ylamino]-7H-pyrrolo[2,3-d]pyrimidine-6-carboxylic acid dimethylamide

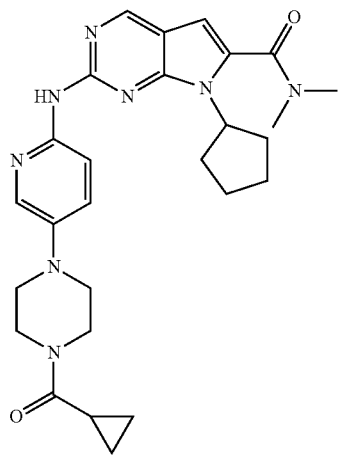 [SMILES: CN(C)C(=O)c1cc2cnc(Nc3ccc(N4CCN(C(=O)C5CC5)CC4)cn3)nc2n1C1CCCC1]

To a solution of 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and cyclopropanecarbonyl chloride (22 mL, 0.690 mmol) in 5 mL of $CH_2Cl_2$ is added a solution of $Et_3N$ (64 mL, 0.459 mmol) and stirred at rt for 18 h. The resulting mixture is concentrated and diluted with saturated $NaHCO_3$ and extracted with ethyl acetate (3×100 mL). The combine organics are dried over $Na_2CO_3$ and preparative HPLC to give 2-[5-(4-carbamoylmethyl-piperazin-1-yl)-pyridin-2-ylamino]-7-cyclopentyl-7H-pyrrolo[2,3-d]pyrimidine-6-carboxylic acid dimethylamide (81 mg, 68%). MS (ESI) m/z 503.3 (M+H)$^+$

EXAMPLE 23

2-[5-(4-Cyclohexanecarbonyl-piperazin-1-yl)-pyridin-2-ylamino]-7-cyclopentyl-7H-pyrrolo[2,3-d]pyrimidine-6-carboxylic acid dimethylamide

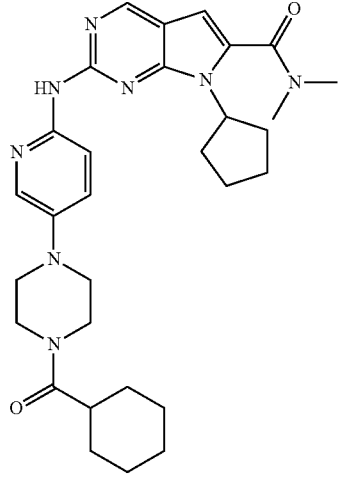 [SMILES: CN(C)C(=O)c1cc2cnc(Nc3ccc(N4CCN(C(=O)C5CCCCC5)CC4)cn3)nc2n1C1CCCC1]

Following General Procedure G, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and cyclohexane carbonyl chloride (37 mg, 0.690 mmol) gave 2-[5-(4-cyclohexanecarbonyl-piperazin-1-yl)-pyridin-2-ylamino]-7-cyclopentyl-7H-pyrrolo[2,3-d]pyrimidine-6-carboxylic acid dimethylamide (63 mg, 49%). MS (ESI) m/z 545.3 (M+H)$^+$

EXAMPLE 90

2-{5-[4-(2-Cyclohexyl-acetyl)-piperazin-1-yl]-pyridin-2-ylamino}-7-cyclopentyl-7H-pyrrolo[2,3-d]pyrimidine-6-carboxylic acid dimethylamide

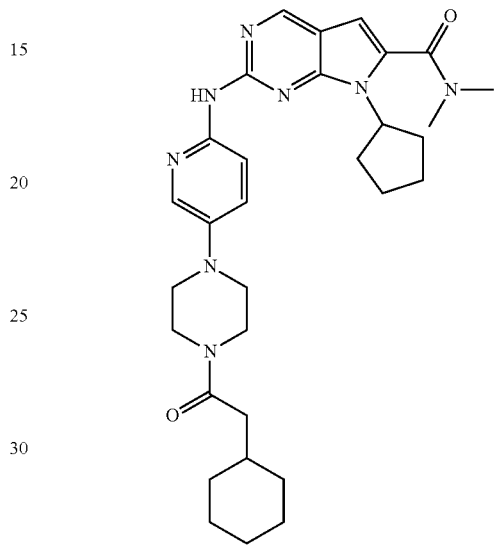

Following General Procedure G, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and cyclohexyl acetyl chloride (39 mL, 0.690 mmol) gave 2-{5-[4-(2-cyclohexyl acetyl)-piperazin-1-yl]-pyridin-2-ylamino}-7-cyclopentyl-7H-pyrrolo[2,3-d]pyrimidine-6-carboxylic acid dimethylamide (61 mg, 47%). MS (ESI) m/z 559.4 (M+H)$^+$

EXAMPLE 91

7-Cyclopentyl-2-{5-[4-(3-cyclopentyl-propionyl)-piperazin-1-yl]-pyridin-2-ylamino}-7H-pyrrolo[2,3-d]pyrimidine-6-carboxylic acid dimethylamide

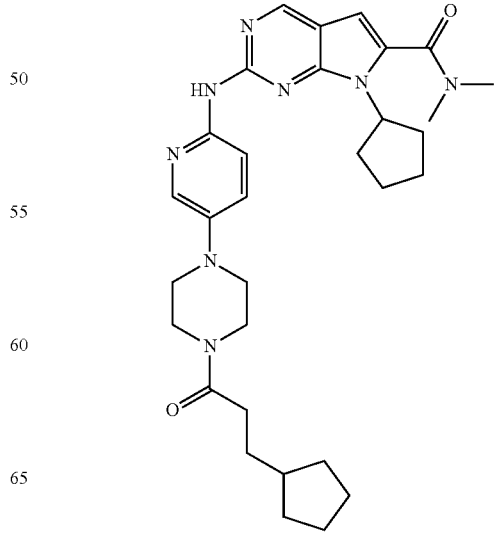

Following General Procedure G, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and 3-cyclopentyl propionyl chloride (39 mL, 0.690 mmol) gave 7-cyclopentyl-2-{5-[4-(3-cyclopentyl-propionyl)-piperazin-1-yl]-pyridin-2-ylamino}-7H-pyrrolo[2,3-d]pyrimidine-6-carboxylic acid dimethylamide (57 mg, 44%). MS (ESI) m/z 559.4 (M+H)⁺

EXAMPLE 22

7-Cyclopentyl-2-{5-[4-(pyrrolidine-1-carbonyl)-piperazin-1-yl]-pyridin-2-ylamino}-7H-pyrrolo[2,3-d]pyrimidine-6-carboxylic acid dimethylamide

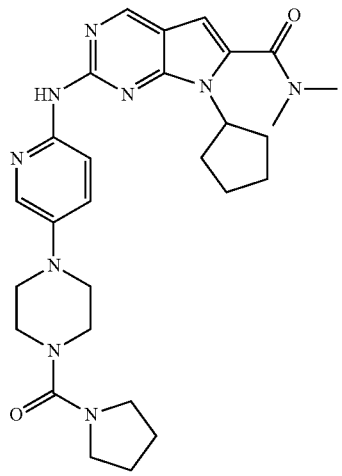 [SMILES: CN(C)C(=O)c1cc2cnc(Nc3ccc(N4CCN(C(=O)N5CCCC5)CC4)cn3)nc2n1C1CCCC1]

Following General Procedure G, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and pyrrolidine-1-carbonyl chloride (25 mL, 0.690 mmol) gave 7-cyclopentyl-2-{5-[4-(pyrrolidine-1-carbonyl)-piperazin-1-yl]-pyridin-2-ylamino}-7H-pyrrolo[2,3-d]pyrimidine-6-carboxylic acid dimethylamide (84 mg, 70%). MS (ESI) m/z 532.3 (M+H)⁺

EXAMPLE 94

7-Cyclopentyl-2-{5-[4-(piperidine-1-carbonyl)-piperazin-1-yl]-pyridin-2-ylamino}-7H-pyrrolo[2,3-d]pyrimidine-6-carboxylic acid dimethylamide

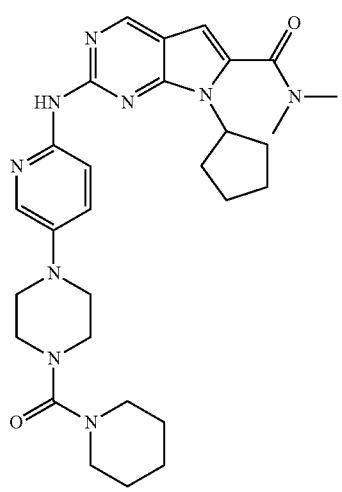 [SMILES: CN(C)C(=O)c1cc2cnc(Nc3ccc(N4CCN(C(=O)N5CCCCC5)CC4)cn3)nc2n1C1CCCC1]

Following General Procedure G, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and piperidine-1-carbonyl bromide (32 mL, 0.690 mmol) gave 7-cyclopentyl-2-{5-[4-(piperidine-1-carbonyl)-piperazin-1-yl]-pyridin-2-ylamino}-7H-pyrrolo[2,3-d]pyrimidine-6-carboxylic acid dimethylamide (83 mg, 64%). MS (ESI) m/z 546.3 (M+H)⁺

EXAMPLE 38

7-Cyclopentyl-2-{5-[4-(morpholine-4-carbonyl)-piperazin-1-yl]-pyridin-2-ylamino}-7H-pyrrolo[2,3-d]pyrimidine-6-carboxylic acid dimethylamide

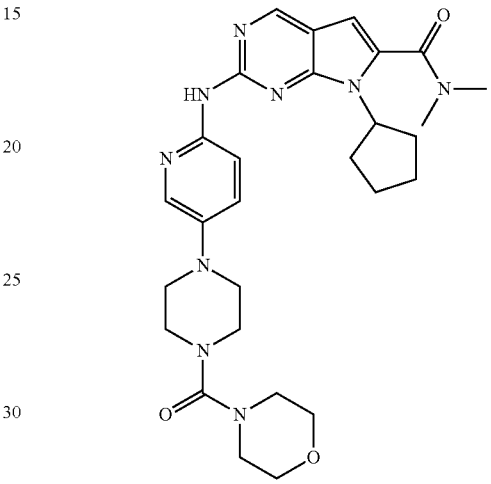

Following General Procedure G, 7-cyclopentyl-2-(5-piperazin-1-yl-pyridin-2-ylamino)-7H-pyrrolo[2,3-d]pyrimidine-6-carboxylic acid dimethylamide (100 mg, 0.230 mmol) and morpholine-4-carbonyl chloride (38 mg, 0.690 mmol) gave 7-cyclopentyl-2-{5-[4-(morpholine-4-carbonyl)-piperazin-1-yl]-pyridin-2-ylamino}-7H-pyrrolo[2,3-d]pyrimidine-6-carboxylic acid dimethylamide (80 mg, 62%). MS (ESI) m/z 548.3 (M+H)⁺

EXAMPLE 30

(R)-4-[6-(7-Cyclopentyl-6-dimethylcarbamoyl-7H-pyrrolo[2,3-d]pyrimidin-2-ylamino)-pyridin-3-yl]-2-methyl-piperazine-1-carboxylic acid tert-butyl ester

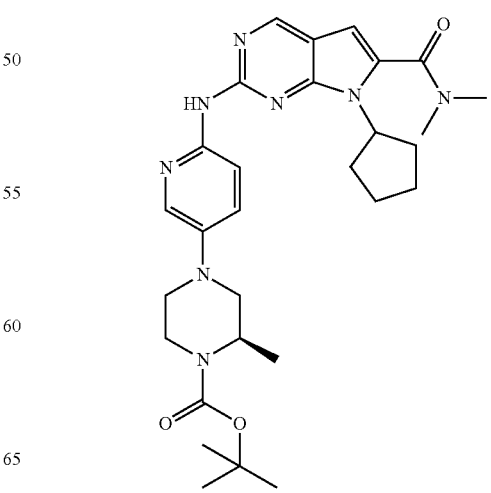

Following Buchwald Method B, 2-chloro-7-cyclopentyl-7H-pyrrolo[2,3-d]pyrimidine-6-carboxylic acid dimethylamide (200 mg, 0.200 mmol) and (R)-2-methyl-piperazine-1-carboxylic acid tert-butyl ester (200 mg, 0.682 mmol) gave (R)-4-[6-(7-cyclopentyl-6-dimethylcarbamoyl-7H-pyrrolo[2,3-d]pyrimidin-2-ylamino)-pyridin-3-yl]-2-methyl-piperazine-1-carboxylic acid tert-butyl ester (131 mg, 35%). MS (ESI) m/z 549.5 (M+H)+

EXAMPLE 31

(S)-4-[6-(7-Cyclopentyl-6-dimethylcarbamoyl-7H-pyrrolo[2,3-d]pyrimidin-2-ylamino)-pyridin-3-yl]-2-methyl-piperazine-1-carboxylic acid tert-butyl ester

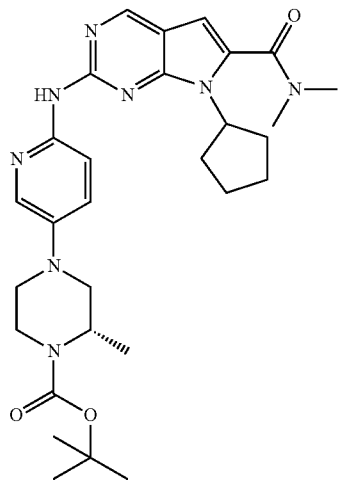 [SMILES: C[C@H]1CN(c2ccc(Nc3ncc4cc(C(=O)N(C)C)n(C5CCCC5)c4n3)nc2)CCN1C(=O)OC(C)(C)C]

Following Buchwald Method B, 2-chloro-7-cyclopentyl-7H-pyrrolo[2,3-d]pyrimidine-6-carboxylic acid dimethylamide (200 mg, 0.200 mmol) and (S)-2-methyl-piperazine-1-carboxylic acid tert-butyl ester (200 mg, 0.682 mmol) gave (S)-4-[6-(7-cyclopentyl-6-dimethylcarbamoyl-7H-pyrrolo[2,3-d]pyrimidin-2-ylamino)-pyridin-3-yl]-2-methyl-piperazine-1-carboxylic acid tert-butyl ester (157 mg, 42%). MS (ESI) m/z 549.5 (M+H)ⁱ

EXAMPLE 16

7-Cyclopentyl-2-[5-((R)-3-methyl-piperazin-1-yl)-pyridin-2-ylamino]-7H-pyrrolo[2,3-d]pyrimidine-6-carboxylic acid dimethylamide

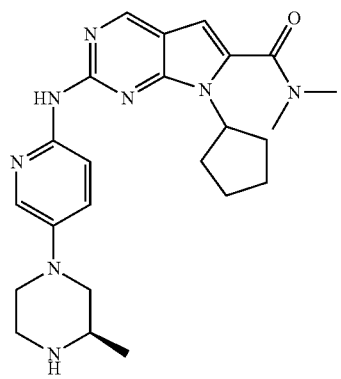 [SMILES: C[C@@H]1CN(c2ccc(Nc3ncc4cc(C(=O)N(C)C)n(C5CCCC5)c4n3)nc2)CCN1]

Following General Procedure A, (R)-4-[6-(7-cyclopentyl-6-dimethylcarbamoyl-7H-pyrrolo[2,3-d]pyrimidin-2-ylamino)-pyridin-3-yl]-2-methyl-piperazine-1-carboxylic acid tert-butyl ester (131 mg, 0.200 mmol) gave 7-cyclopentyl-2-[5-((R)-3-methyl-piperazin-1-yl)-pyridin-2-ylamino]-7H-pyrrolo[2,3-d]pyrimidine-6-carboxylic acid dimethylamide (55 mg, 50%). MS (ESI) m/z 449.3 (M+H)+

¹H NMR (400 MHz, CDCl₃): 8.71 (1H, s), 8.38 (1H, d), 8.03 (1H, s), 7.80 (1H, s), 7.36 (1H, d), 6.46 (1H, s), 4.84-4.80 (1H, m), 3.46 (3H, d), 3.18 (6H, s), 3.14-3.05 (2H, m), 2.82-2.75 (1H, m), 2.60-2.55 (3H, m), 2.47-2.41 (1H, m), 2.10-2.04 (4H, m), 1.94-1.67 (4H, m).

EXAMPLE 81

7-Cyclopentyl-2-{5-[(R)-4-(2-hydroxy-ethyl)-3-methyl-piperazin-1-yl]-pyridin-2-ylamino}-7H-pyrrolo[2,3-d]pyrimidine-6-carboxylic acid dimethylamide

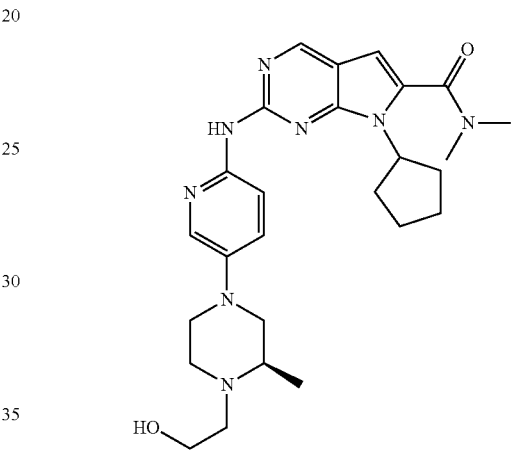

Following General Procedure D, 7-cyclopentyl-2-[5-((R)-3-methyl-piperazin-1-yl)-pyridin-2-ylamino]-7H-pyrrolo[2,3-d]pyrimidine-6-carboxylic acid dimethylamide (43 mg, 0.095 mmol) and 2-bromo ethanol (13 mg, 0.105 mmol) gave 7-cyclopentyl-2-{5-[(R)-4-(2-hydroxy-ethyl)-3-methyl-piperazin-1-yl]-pyridin-2-ylamino}-7H-pyrrolo[2,3-d]pyrimidine-6-carboxylic acid dimethylamide (32 mg, 68%). MS (ESI) m/z 493.3 (M+H)+

EXAMPLE 17

7-Cyclopentyl-2-[5-((S)-3-methyl-piperazin-1-yl)-pyridin-2-ylamino]-7H-pyrrolo[2,3-d]pyrimidine-6-carboxylic acid dimethylamide

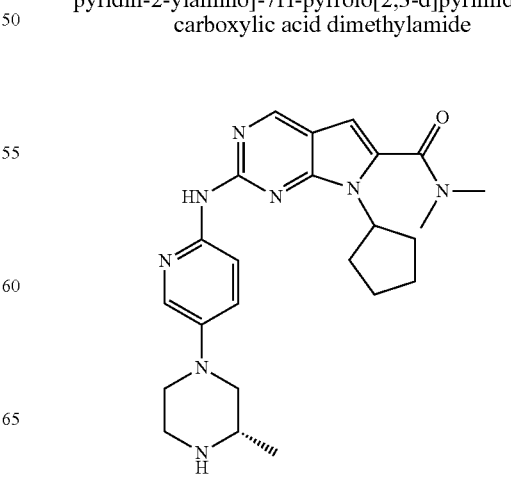

Following General Procedure A, (S)-4-[6-(7-cyclopentyl-6-dimethylcarbamoyl-7H-pyrrolo[2,3-d]pyrimidin-2-ylamino)-pyridin-3-yl]-2-methyl-piperazine-1-carboxylic acid tert-butyl ester (145 mg, 0.200 mmol) gave 7-cyclopentyl-2-[5-((S)-3-methyl-piperazin-1-yl)-pyridin-2-ylamino]-7H-pyrrolo[2,3-d]pyrimidine-6-carboxylic acid dimethylamide (86 mg, 72%). MS (ESI) m/z 449.3 (M+H)+

EXAMPLE 82

7-Cyclopentyl-2-{5-[(S)-4-(2-hydroxy-ethyl)-3-methyl-piperazin-1-yl]-pyridin-2-ylamino}-7H-pyrrolo[2,3-d]pyrimidine-6-carboxylic acid dimethylamide

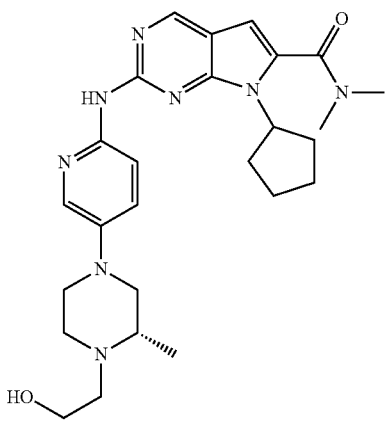 [SMILES: C[C@H]1CN(c2ccc(Nc3ncc4cc(C(=O)N(C)C)n(C5CCCC5)c4n3)nc2)CCN1CCO]

Following General Procedure D, 7-cyclopentyl-2-[5-((S)-3-methyl-piperazin-1-yl)-pyridin-2-ylamino]-7H-pyrrolo[2,3-d]pyrimidine-6-carboxylic acid dimethylamide (74 mg, 0.17 mmol) and 2-bromo ethanol (23 mg, 0.18 mmol) gave 7-cyclopentyl-2-{5-[(S)-4-(2-hydroxy-ethyl)-3-methyl-piperazin-1-yl]-pyridin-2-ylamino}-7H-pyrrolo[2,3-d]pyrimidine-6-carboxylic acid dimethylamide (34 mg, 42%). MS (ESI) m/z 493.3 (M+H)+

EXAMPLE 72

7-Cyclopentyl-2-[5-(3,3-dimethyl-piperazin-1-yl)-pyridin-2-ylamino]-7H-pyrrolo[2,3-d]pyrimidine-6-carboxylic acid dimethylamide

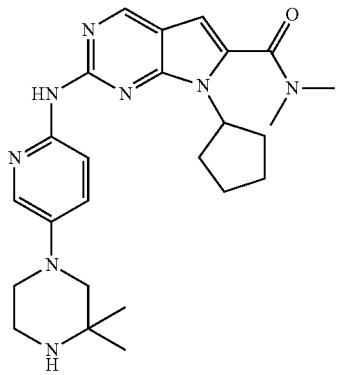 [SMILES: CN(C)C(=O)c1cc2cnc(Nc3ccc(N4CCNC(C)(C)C4)cn3)nc2n1C1CCCC1]

Following Buchwald Method B, 2-chloro-7-cyclopentyl-7H-pyrrolo[2,3-d]pyrimidine-6-carboxylic acid dimethylamide (50 mg, 0.17 mmol) and 4-(6-amino-pyridin-3-yl)-2,2-dimethyl-piperazine-1-carboxylic acid tert-butyl ester (58 mg, 0.15 mmol) gave 7-cyclopentyl-2-[5-(3,3-dimethyl-piperazin-1-yl)-pyridin-2-ylamino]-7H-pyrrolo[2,3-d]pyrimidine-6-carboxylic acid dimethylamide (20 mg, 25%). MS (ESI) m/z 463.3 (M+H)+

EXAMPLE 24

7-Cyclopentyl-2-[5-(3,5-dimethyl-piperazin-1-yl)-pyridin-2-ylamino]-7H-pyrrolo[2,3-d]pyrimidine-6-carboxylic acid dimethylamide

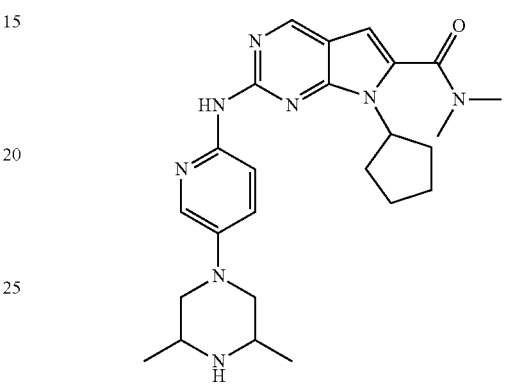

Following General Procedure A, 4-[6-(7-Cyclopentyl-6-dimethylcarbamoyl-7H-pyrrolo[2,3-d]pyrimidin-2-ylamino)-pyridin-3-yl]-2,6-dimethyl-piperazine-1-carboxylic acid tert-butyl ester (150 mg, 0.27 mmol) gave 7-cyclopentyl-2-[5-(3,5-dimethyl-piperazin-1-yl)-pyridin-2-ylamino]-7H-pyrrolo[2,3-d]pyrimidine-6-carboxylic acid dimethylamide (70 mg, 58%).

MS (ESI) m/z 463.3 (M+H)+

1H NMR (400 MHz, DMSO-d6): 9.33 (1H, s), 8.76 (1H, s), 8.15 (1H, d), 7.98 (1H, s), 7.43, (1H, d), 6.61 (1H, s), 4.76-4.72 (1H, m), 3.50-3.48 (2H, m), 3.08-3.05 (3H, m), 2.89-2.86 (2H, m), 2.50 (12H, s), 2.48-2.43 (2H, m), 2.14-2.05 (2H, m), 2.00-1.90 (2H, m), 1.70-1.60 (1H, m).

EXAMPLE 4

7-Cyclopentyl-2-[5-(3-oxo-piperazin-1-yl)-pyridin-2-ylamino]-7H-pyrrolo[2,3-d]pyrimidine-6-carboxylic acid dimethylamide

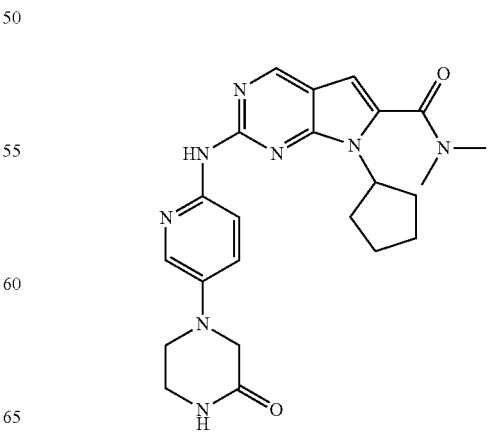

Following Buchwald Method B, 2-chloro-7-cyclopentyl-7H-pyrrolo[2,3-d]pyrimidine-6-carboxylic acid dimethylamide (100 mg, 0.34 mmol) and 4-(6-amino-pyridin-3-yl)-piperazin-2-one (111 mg, 0.578 mmol) gave 7-cyclopentyl-2-[5-(3-oxo-piperazin-1-yl)-pyridin-2-ylamino]-7H-pyrrolo[2,3-d]pyrimidine-6-carboxylic acid dimethylamide (35 mg, 35%). MS (ESI) m/z 449.2 (M+H)+

EXAMPLE 39

7-Cyclopentyl-2-[5-((S)-3-hydroxy-pyrrolidin-1-yl)-pyridin-2-ylamino]-7H-pyrrolo[2,3-d]pyrimidine-6-carboxylic acid dimethylamide

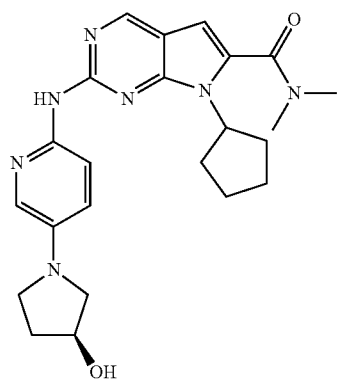 [SMILES: CN(C)C(=O)c1cc2cnc(Nc3ccc(N4CC[C@H](O)C4)cn3)nc2n1C1CCCC1]

Following Buchwald Method B, 2-chloro-7-cyclopentyl-7H-pyrrolo[2,3-d]pyrimidine-6-carboxylic acid dimethylamide (101 mg, 0.35 mmol) and N-{(E)-2-[(S)-3-(tert-butyl-dimethyl-silanyloxy)-pyrrolidin-1-yl]-vinyl}-acrylamidine (153 mg, 0.52 mmol), followed by deprotection with TBAF to give 7-cyclopentyl-2-[5-((S)-3-hydroxy-pyrrolidin-1-yl)-pyridin-2-ylamino]-7H-pyrrolo[2,3-d]pyrimidine-6-carboxylic acid dimethylamide (98 mg, 65%). MS (ESI) m/z 436.3 (M+H)+

EXAMPLE 32

7-Cyclopentyl-2-[5-(3-hydroxy-azetidin-1-yl)-pyridin-2-ylamino]-7H-pyrrolo[2,3-d]pyrimidine-6-carboxylic acid dimethylamide

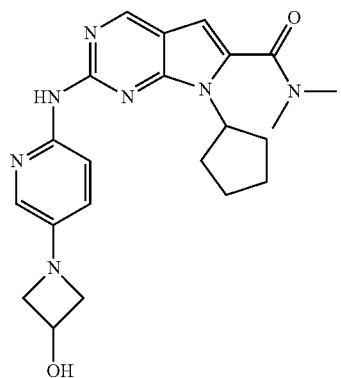 [SMILES: CN(C)C(=O)c1cc2cnc(Nc3ccc(N4CC(O)C4)cn3)nc2n1C1CCCC1]

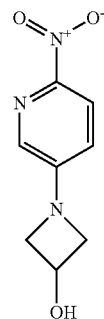

To a solution of 5-bromo-2-nitropyridine (0.54 g, 2.66 mmol), azetidin-3-ol hydrochloride (0.46 g, 4.17 mmol) and tetrabutylammonium iodide (0.103 g, 0.278 mmol) in 6 mL of DMSO is added potassium carbonate (1.06 g, 7.68 mmol). The resulting mixture is heated to 80° C. for 3 h. Poured into ethyl acetate/NaHCO₃ solution. Extracted with ethyl acetate (2×250 mL). The organic layer is ished with brine and dried over Na₂SO₄. Concentrated to give 1-(6-nitro-pyridin-3-yl)-azetidin-3-ol (153 mg, 29%). MS (ESI) m/z 240.1 (M+H)+

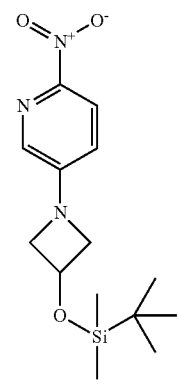 [SMILES: CC(C)(C)[Si](C)(C)OC1CN(c2ccc([N+](=O)[O-])nc2)C1]

To a solution of 1-(6-nitro-pyridin-3-yl)-azetidin-3-ol (154 mg, 0.779 mmol) in 2 mL of DMF is added Et₃N (0.2 mL, 0.15 mmol), TBDMSCl (117 mg, 0.776 mmol). The resulting mixture is stirred at room temperature for 2 h. Poured into EtOAc/NaHCO₃, the aqueous layer is extracted with ethyl acetate (2×50 mL). The combined organic layers are ished with brine, dried over Na₂SO₄. Concentrated to give 5-[3-(tert-butyl-dimethyl-silanyloxy)-azetidin-1-yl]-2-nitro-pyridine (175 mg, 73%).

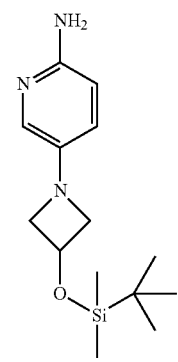 [SMILES: CC(C)(C)[Si](C)(C)OC1CN(c2ccc(N)nc2)C1]

To a suspension of 5-[3-(tert-butyl-dimethyl-silanyloxy)-azetidin-1-yl]-2-nitro-pyridine (124 mg, 0.401 mmol) in 5 mL of ethanol is added iron powder (206 mg, 3.68 mmol) then 2 mL of NH$_4$Cl solution. The resulting mixture is heated at 80° C. for 3 h and filtered through celite and concentrated. The resulting dark solid is divided between ethyl acetate and water. The aqueous phase is extracted with ethyl acetate (2×50 mL). The combine organic layers are ished with brine, dried over Na$_2$SO$_4$ and concentrated to give 5-[3-(tert-butyl-dimethyl-silanyloxy)-azetidin-1-yl]-pyridin-2-ylamine (105 mg, 94%).

Following Buchwald Method B, 2-chloro-7-cyclopentyl-7H-pyrrolo[2,3-d]pyrimidine-6-carboxylic acid dimethylamide (120 mg, 0.411 mmol) and N-{(E)-2-[(S)-3-(tert-butyl-dimethyl-silanyloxy)-pyrrolidin-1-yl]-vinyl}-acrylamidine (112 mg, 0.401 mmol), followed by deprotection with 2 mL of TBAF to give 7-cyclopentyl-2-[5-(3-hydroxy-azetidin-1-yl)-pyridin-2-ylamino]-7H-pyrrolo[2,3-d]pyrimidine-6-carboxylic acid dimethylamide (18 mg, 46%). MS (ESI) m/z 422.5 (M+H)$^+$

EXAMPLE 59

2-{5-[(2-Amino-ethyl)-methyl-amino]-pyridin-2-ylamino}-7-cyclopentyl-7H-pyrrolo[2,3-d]pyrimidine-6-carboxylic acid dimethylamide

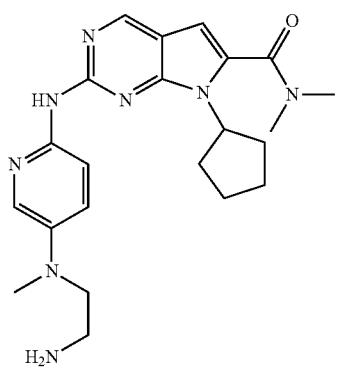 [SMILES: CN(C)C(=O)c1cc2cnc(Nc3ccc(N(C)CCN)cn3)nc2n1C1CCCC1]

Following Buchwald Method B, 2-chloro-7-cyclopentyl-7H-pyrrolo[2,3-d]pyrimidine-6-carboxylic acid dimethylamide (200 mg, 0.68 mmol) and {2-[(6-amino-pyridin-3-yl)-methyl-amino]-ethyl}-carbamic acid tert-butyl ester (200 mg, 0.75 mmol), followed by deprotection using General Procedure A to give 2-{5-[(2-amino-ethyl)-methyl-amino]-pyridin-2-ylamino}-7-cyclopentyl-7H-pyrrolo[2,3-d]pyrimidine-6-carboxylic acid dimethylamide (100 mg, 34%). MS (ESI) m/z 423.4 (M+H)$^+$

EXAMPLE 83

7-Cyclopentyl-2-{5-[(2-hydroxy-ethyl)-methyl-amino]-pyridin-2-ylamino}-7H-pyrrolo[2,3-d]pyrimidine-6-carboxylic acid dimethylamide

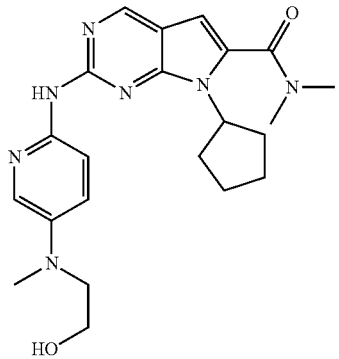 [SMILES: CN(C)C(=O)c1cc2cnc(Nc3ccc(N(C)CCO)cn3)nc2n1C1CCCC1]

Following Buchwald Method B, 2-chloro-7-cyclopentyl-7H-pyrrolo[2,3-d]pyrimidine-6-carboxylic acid dimethylamide (25 mg, 0.85 mmol) and [2-(tert-butyl dimethyl silanyloxy)-ethyl]-methyl amine (27 mg, 0.094 mmol), followed by deprotection using 0.6 mL of TBAF in 2 mL of THF to give 7-cyclopentyl-2-{5-[(2-hydroxy-ethyl)-methyl-amino]-pyridin-2-ylamino}-7H-pyrrolo[2,3-d]pyrimidine-6-carboxylic acid dimethylamide (18 mg, 72%). MS (EST) m/z 424.2 (M+H)$^|$ $^1$H NMR (400 MHz, CDCl$_3$): 8.78 (1H, s), 8.59-8.41 (2H, m), 8.23 (1H, d), 7.65 (1H, dd), 6.47 (1H, s), 4.88-4.72 (1H, m), 4.55-4.42 (1H, m), 3.84-3.42 (4H, m), 3.17 (6H, s), 3.02 (2H, t), 2.68-2.53 (2H, m), 2.07 (4H, d), 1.73 (2H, d).

EXAMPLE 3

7-Cyclopentyl-2-[5-(piperidin-4-ylcarbamoyl)-pyridin-2-ylamino]-7H-pyrrolo[2,3-d]pyrimidine-6-carboxylic acid dimethylamide

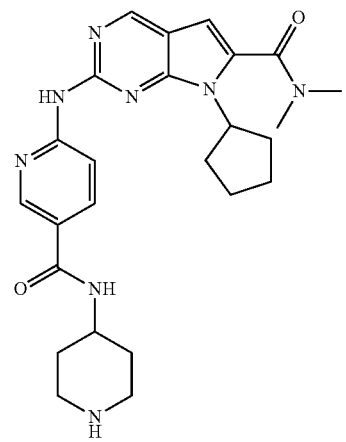 [SMILES: CN(C)C(=O)c1cc2cnc(Nc3ccc(C(=O)NC4CCNCC4)cn3)nc2n1C1CCCC1]

Following Buchwald Method B, 2-chloro-7-cyclopentyl-7H-pyrrolo[2,3-d]pyrimidine-6-carboxylic acid dimethylamide (25 mg, 0.85 mmol) and 4-[(6-amino-pyridine-3-carbonyl)-amino]-piperidine-1-carboxylic acid tert-butyl ester (27 mg, 0.094 mmol), followed by deprotection using 0.6 mL of TBAF in 2 mL of THF to give 7-cyclopentyl-2-[5-(piperidin-4-ylcarbamoyl)-pyridin-2-ylamino]-7H-pyrrolo[2,3-d]pyrimidine-6-carboxylic acid dimethylamide (18 mg, 72%). MS (ESI) m/z 424.2 (M+H)$^+$

EXAMPLE 53

7-Cyclopentyl-2-[5-(methyl-piperidin-4-yl-carbamoyl)-pyridin-2-ylamino]-7H-pyrrolo[2,3-d]pyrimidine-6-carboxylic acid dimethylamide

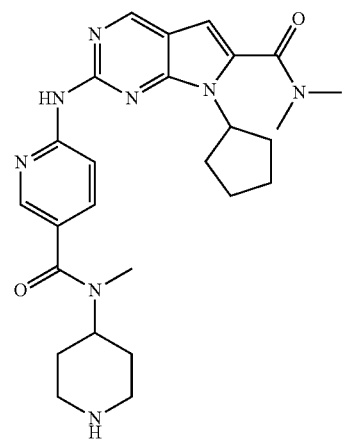 [SMILES: CN(C)C(=O)c1cc2cnc(Nc3ccc(C(=O)N(C)C4CCNCC4)cn3)nc2n1C1CCCC1]

Following Buchwald Method B, 2-chloro-7-cyclopentyl-7H-pyrrolo[2,3-d]pyrimidine-6-carboxylic acid dimethylamide (170 mg, 0.58 mmol) and 4-[(6-amino-pyridine-3-carbonyl)-methyl-amino]-piperidine-1-carboxylic acid tert-butyl ester (292 mg, 0.87 mmol), followed by deprotection using General Procedure A to give 7-cyclopentyl-2-[5-(methyl-piperidin-4-yl-carbamoyl)-pyridin-2-ylamino]-7H-pyrrolo[2,3-d]pyrimidine-6-carboxylic acid dimethylamide (46 mg, 16%). MS (ESI) m/z 491.3 (M+H)+

EXAMPLE 49

7-Cyclopentyl-2-[5-(piperazine-1-carbonyl)-pyridin-2-ylamino]-7H-pyrrolo[2,3-d]pyrimidine-6-carboxylic acid dimethylamide

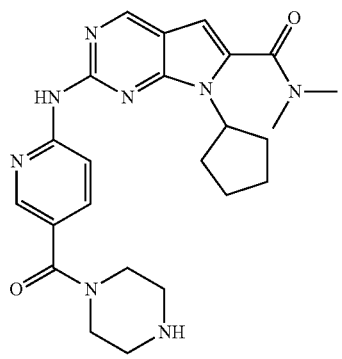 [SMILES: CN(C)C(=O)c1cc2cnc(Nc3ccc(C(=O)N4CCNCC4)cn3)nc2n1C1CCCC1]

Following Buchwald Method B, 2-chloro-7-cyclopentyl-7H-pyrrolo[2,3-d]pyrimidine-6-carboxylic acid dimethylamide (205 mg, 0.7 mmol) and 4-(6-amino-pyridine-3-carbonyl)-piperazine-1-carboxylic acid tort-butyl ester (236 mg, 0.8 mmol), followed by deprotection using General Procedure A to give 7-cyclopentyl-2-[5-(piperazine-1-carbonyl)-pyridin-2-ylamino]-7H-pyrrolo[2,3-d]pyrimidine-6-carboxylic acid dimethylamide (13 mg, 41%).
MS (ESI) m/z 463.3 (M+H)¹

EXAMPLE 96

7-Cyclopentyl-2-{5-[4-(2-hydroxy-ethyl)-piperazine-1-carbonyl]-pyridin-2-ylamino}-7H-pyrrolo[2,3-d]pyrimidine-6-carboxylic acid dimethylamide

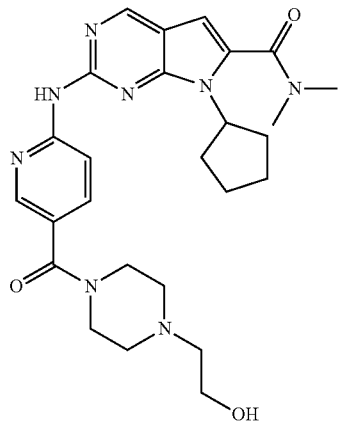 [SMILES: CN(C)C(=O)c1cc2cnc(Nc3ccc(C(=O)N4CCN(CCO)CC4)cn3)nc2n1C1CCCC1]

Following General Procedure D, 7-cyclopentyl-2-[5-(piperazine-1-carbonyl)-pyridin-2-ylamino]-7H-pyrrolo[2,3-d]pyrimidine-6-carboxylic acid dimethylamide (200 mL, 0.43 mmol) and 2-bromo ethanol (37 mg, 0.52 mmol) to give 7-cyclopentyl-2-{5-[4-(2-hydroxy-ethyl)-piperazine-1-carbonyl]-pyridin-2-ylamino}-7H-pyrrolo[2,3-d]pyrimidine-6-carboxylic acid dimethylamide (100 mg, 48%). MS (ESI) m/z 478.3 (M+H)¹

EXAMPLE D 6-(7-Cyclopentyl-6-dimethylcarbamoyl-7H-pyrrolo[2,3-d]pyrimidin-2-ylamino)-nicotinic acid

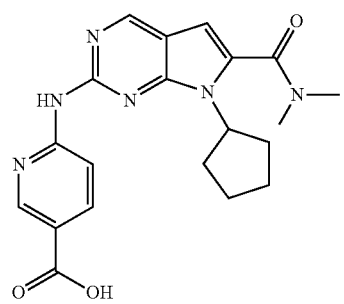 [SMILES: CN(C)C(=O)c1cc2cnc(Nc3ccc(C(=O)O)cn3)nc2n1C1CCCC1]

Following General Procedure D, 7-cyclopentyl-2-[5-(piperazine-1-carbonyl)-pyridin-2-ylamino]-7H-pyrrolo[2,3-d]pyrimidine-6-carboxylic acid dimethylamide (2 g, 6.83 mmol) and 6-amino-nicotinic acid methyl ester (1.15 g, 7.51 mmol). Followed by treatment with LiOH (1 g, 25 mmol) in 320 mL of THF/H₂O gave 6-(7-cyclopentyl-6-dimethylcarbamoyl-7H-pyrrolo[2,3-d]pyrimidin-2-ylamino) nicotinic acid (1.2 g, 55%). MS (ESI) m/z 395.3 (M+H)+

EXAMPLE 50

7-Cyclopentyl-2-[5-(4-dimethylamino-piperidine-1-carbonyl)-pyridin-2-ylamino]-7H-pyrrolo[2,3-d]pyrimidine-6-carboxylic acid dimethylamide

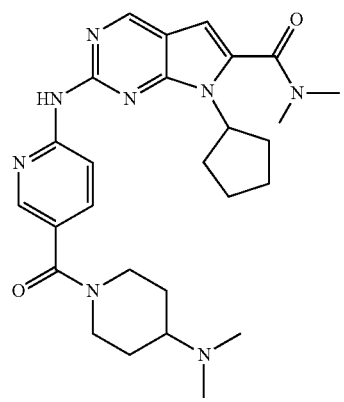 [SMILES: CN(C)C(=O)c1cc2cnc(Nc3ccc(C(=O)N4CCC(N(C)C)CC4)cn3)nc2n1C1CCCC1]

To a solution of 6-(7-cyclopentyl-6-dimethylcarbamoyl-7H-pyrrolo[2,3-d]pyrimidin-2-ylamino)-nicotinic acid (100 mg, 0.25 mmol) (Example D) in 3 mL of DMF is added dimethyl-piperidin-4-yl-amine (33 mg, 0.25 mmol), HBTU (140 mg, 0.38 mmol), and DIPEA (0.088 mL, 0.51 mmol). After 48 h stirring at room temperature, the resulting mixture is concentrated and diluted with saturated NaHCO$_3$ and extracted with ethyl acetate (3×100 mL). The combine organics are dried over Na$_2$CO$_3$ and concentrated to give a reddish residue. Preparative HPLC to give 7-cyclopentyl-2-[5-(4-dimethylamino-piperidine-1-carbonyl)-pyridin-2-ylamino]-7H-pyrrolo[2,3-d]pyrimidine-6-carboxylic acid dimethylamide (60 mg, 46%). MS (ESI) m/z 505.5 (M+H)$^+$ $^1$H NMR (400 MHz, DMSO-d6): 9.97 (1H, s), 8.85 (1H, s), 8.34 (1H, d), 7.83 (1H, d), 6.65 (1H, s), 4.80-4.72 (1H, m), 4.06-4.00 (1H, s), 3.06 (6H, s), 2.48-2.40 (2H, m), 2.39-2.30 (2H, m), 2.18 (6H, s), 2.05-1.95 (5H, m), 1.82-1.70 (2h, m), 1.69-1.60 (2H, m), 1.41-1.32 (2H, m), 1.19-1.16 (2h, m).

EXAMPLE 87

7-Cyclopentyl-2-[5-(4-hydroxy-piperidine-1-carbonyl)-pyridin-2-ylamino]-7H-pyrrolo[2,3-d]pyrimidine-6-carboxylic acid dimethylamide

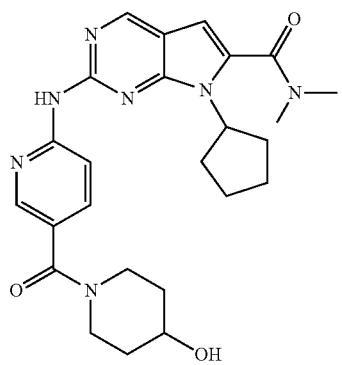 [SMILES: CN(C)C(=O)c1cc2cnc(Nc3ccc(C(=O)N4CCC(O)CC4)cn3)nc2n1C1CCCC1]

To a solution of 6-(7-cyclopentyl-6-dimethylcarbamoyl-7H-pyrrolo[2,3-d]pyrimidin-2-ylamino)-nicotinic acid methyl ester (200 mg, 0.49 mmol) and piperidin-4-ol (500 mg, 4.9 mmol) in 5 mL of CH$_2$Cl$_2$ is added dropwise a solution of iPrMgCl (2.45 mL, 4.9 mmol) at 0° C. and allow to warm up to room temperature overnight. After 18 h, added another 10 equivalents of i-PrMgCl and stirred for another 5 h. The reaction mixture is quenched with saturated NH$_4$Cl and extracted with dichloromethane (3×100 mL). The combine organic ished with NaCl and dried over Na$_2$SO$_4$ and concentrated. Following SiO$_2$ chromatography, eluting with 85/15% (CH$_2$Cl$_2$/MeOH) gave 7-cyclopentyl-2-[5-(4-hydroxy-piperidine-1-carbonyl)-pyridin-2-ylamino]-7H-pyrrolo[2,3-d]pyrimidine-6-carboxylic acid dimethylamide (120 mg, 51%). MS (ESI) m/z 478.3 (M+H)$^+$

EXAMPLE 41

2-{5-[(2-Amino-ethyl)-methyl-carbamoyl]-pyridin-2-ylamino}-7-cyclopentyl-7H-pyrrolo[2,3-d]pyrimidine-6-carboxylic acid dimethylamide

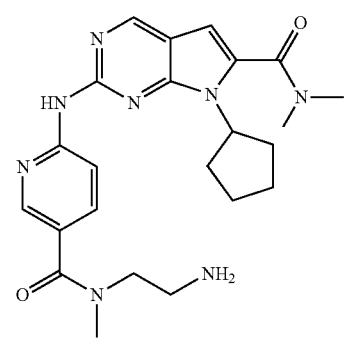 [SMILES: CN(C)C(=O)c1cc2cnc(Nc3ccc(C(=O)N(C)CCN)cn3)nc2n1C1CCCC1]

A solution of 6-(7-cyclopentyl-6-dimethylcarbamoyl-7H-pyrrolo[2,3-d]pyrimidin-2-ylamino)-nicotinic acid (100 mg, 0.25 mmol) in DMF is added (2-methylamino ethyl)-carbamic acid tert-butyl ester (53 mg, 0.25 mmol), HBTU (140 mg, 0.38 mmol), and DIPEA (0.088 mL, 0.51 mmol). After 48 h stirring at room temperature, the resulting mixture is concentrated and diluted with saturated NaHCO$_3$ solution and extracted with ethyl acetate (3×100 mL). The combine organics are dried over Na$_2$CO$_3$ and concentrated to give a reddish residue. Followed by deprotection using General Procedure A to give 2-{5-[(2-amino-ethyl)-methyl-carbamoyl]-pyridin-2-ylamino}-7-cyclopentyl-7H-pyrrolo[2,3-d]pyrimidine-6-carboxylic acid dimethylamide (100 mg, 77%). MS (ESI) m/z 451.3 (M+H)$^|$

EXAMPLE 6

7-Cyclopentyl-2-(4-dimethylamino-3,4,5,6-tetrahydro-2H-[1,3']bipyridinyl-6'-ylamino)-7H-pyrrolo[2,3-d]pyrimidine-6-carboxylic acid dimethylamide

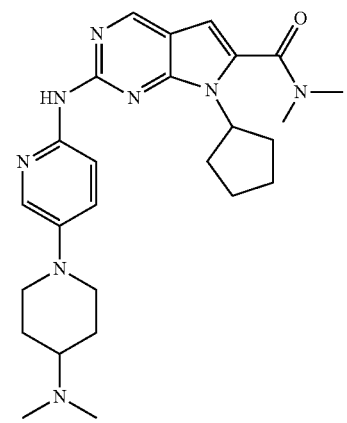 [SMILES: CN(C)C(=O)c1cc2cnc(Nc3ccc(N4CCC(N(C)C)CC4)cn3)nc2n1C1CCCC1]

Following Buchwald Method B, 2-chloro-7-cyclopentyl-7H-pyrrolo[2,3-d]pyrimidine-6-carboxylic acid dimethylamide (100 mg, 0.34 mmol) and N-4,N-4-dimethyl-3,4,5,6-tetrahydro-2H-[1,3']bipyridinyl-4,6'-diamine (113 mg, 0.51 mmol) to give 7-cyclopentyl-2-(4-dimethylamino-3,4,5,6-tetrahydro-2H-[1,3']bipyridinyl-6'-ylamino)-7H-pyrrolo[2,3-d]pyrimidine-6-carboxylic acid dimethylamide (80 mg, 50%). MS (ESI) m/z 477.3 (M+H)⁺

¹H NMR (400 MHz, DMSO-d6): 9.20 (1H, s), 8.74 (1H, s), 8.13 (1H, d), 7.98 (1H, s), 7.43 (1H, d), 6.59 (1H, s), 4.80-4.68 (1H, m), 3.66 (2H, d), 3.10 (6H, s), 2.70-2.60 (2h, m), 2.40-2.30 (2H, m), 2.20 (6H, s), 2.00-2.80 (4H, m), 1.85-1.75 (2H, m), 1.70-1.60 (2H, m), 1.65-1.45 (2H, m).

EXAMPLE 20

7-Cyclopentyl-2-(4-hydroxy-3,4,5,6-tetrahydro-2H-[1,3']bipyridinyl-6'-ylamino)-7H-pyrrolo[2,3-d]pyrimidine-6-carboxylic acid dimethylamide

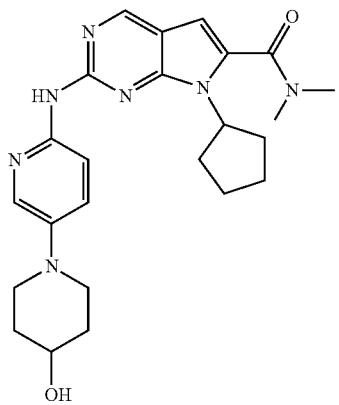 [SMILES: CN(C)C(=O)c1cc2cnc(Nc3ccc(N4CCC(O)CC4)cn3)nc2n1C1CCCC1]

Following Buchwald Method B, 2-chloro-7-cyclopentyl-7H-pyrrolo[2,3-d]pyrimidine-6-carboxylic acid dimethylamide (290 mg, 0.939 mmol) and 4-(tert-butyl-dimethyl-silanyloxy)-3,4,5,6-tetrahydro-2H-[1,3']bipyridinyl-6'-ylamine (336 mg, 1.09 mmol). Followed by deprotection using 7 mL of TBAF in 28 mL of THF to give 7-cyclopentyl-2-(4-dimethylamino-3,4,5,6-tetrahydro-2H-[1,3']bipyridinyl-6'-ylamino)-7H-pyrrolo[2,3-d]pyrimidine-6-carboxylic acid dimethylamide (110 mg, 61%). MS (ESI) m/z 450.3 (M+H)⁺

EXAMPLE 35

7-Cyclopentyl-2-[4-(2-hydroxy-ethyl)-3,4,5,6-tetrahydro-2H-[1,3']bipyridinyl-6'-ylamino]-7H-pyrrolo[2,3-d]pyrimidine-6-carboxylic acid dimethylamide

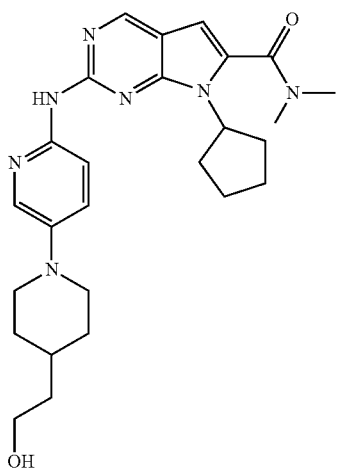 [SMILES: CN(C)C(=O)c1cc2cnc(Nc3ccc(N4CCC(CCO)CC4)cn3)nc2n1C1CCCC1]

Following Buchwald Method B, 2-chloro-7-cyclopentyl-7H-pyrrolo[2,3-d]pyrimidine-6-carboxylic acid dimethylamide (100 mg, 0.34 mmol) and 2-(6'-amino-3,4,5,6-tetrahydro-2H-[1,3']bipyridinyl-4-yl)-ethanol (90 mg, 0.38 mmol) to give 7-cyclopentyl-2-[4-(2-hydroxy-ethyl)-3,4,5,6-tetrahydro-2H-[1,3']bipyridinyl-6'-ylamino]-7H-pyrrolo[2,3-d]pyrimidine-6-carboxylic acid dimethylamide (80 mg, 93%). MS (ESI) m/z 478.3 (M+H)⁺

EXAMPLE 52

7-Cyclopentyl-2-(1',2',3',4',5',6'-hexahydro-[3,4']bipyridinyl-6-ylamino)-7H-pyrrolo[2,3-d]pyrimidine-6-carboxylic acid dimethylamide

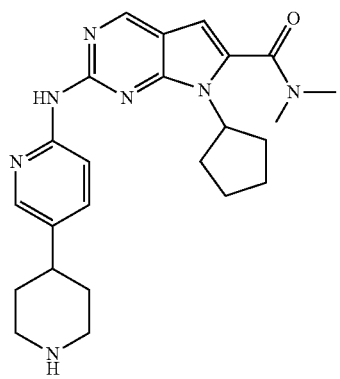 [SMILES: CN(C)C(=O)c1cc2cnc(Nc3ccc(C4CCNCC4)cn3)nc2n1C1CCCC1]

Following Buchwald Method B, 2-chloro-7-cyclopentyl-7H-pyrrolo[2,3-d]pyrimidine-6-carboxylic acid dimethylamide (300 mg, 1.03 mmol) and 6-amino-3',4',5',6'-tetrahydro-2'H-[3,4']bipyridinyl-1'-carboxylic acid tert-butyl ester (313 mg, 1.13 mmol), followed by deprotection using General Procedure A to give 7-cyclopentyl-2-(1',2',3',4',5',6'-hexahydro-[3,4']pyridinyl-6-ylamino)-7H-pyrrolo[2,3-d]pyrimidine-6-carboxylic acid dimethylamide (212 mg, 48%). MS (ESI) m/z 434.3 (M+H)⁺

¹H NMR (400 MHz, DMSO-d6): 9.54 (1H, s), 8.80 (1H, s), 8.29 (1H, d), 8.17 (1H, s), 7.62 (1H, d), 6.63 (1H, s), 4.83 (1H, m), 3.38-3.30 (3H, m), 3.06 (6H, s), 3.05-2.95 (1H, m), 2.88-2.80 (1H, m), 2.48-2.40 (4H, m), 2.04-1.95 (4H, m), 1.83-1.70 (2H, m), 1.70-1.64 (2H, m).

EXAMPLE 80

7-Cyclopentyl-2-(1'-isopropyl-1',2',3',4',5',6'-hexahydro-[3,4']bipyridinyl-6-ylamino)-7H-pyrrolo[2,3-d]pyrimidine-6-carboxylic acid dimethylamide

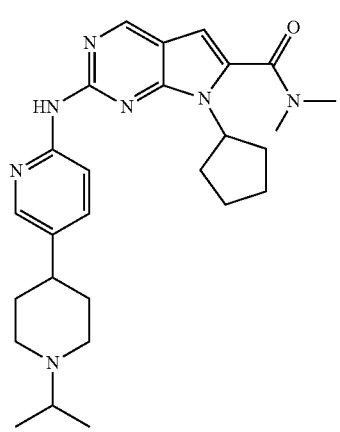

To a suspension of 7-cyclopentyl-2-(1',2',3',4',5',6'-hexahydro-[3,4']bipyridinyl-6-ylamino)-7H-pyrrolo[2,3-d]pyrimidine-6-carboxylic acid dimethylamide (100 mg, 0.23 mmol) in dichloromethane/acetone is added NaBH(OAc)₃ (488 mg, 2.3 mmol) followed by 3 drops of glacial acetic acid. After reaction is completed and concentrated. Diluted with 100 mL of H₂O and basified to pH12 with 50% NaOH solution dropwise (2 mL). Extracted with dichloromethane (3×100 mL) and concentrated to give 7-cyclopentyl-2-(1'-isopropyl-1',2',3',4',5',6'-hexahydro-[3,4']bipyridinyl-6-ylamino)-7H-pyrrolo[2,3-d]pyrimidine-6-carboxylic acid dimethylamide (65 mg, 60%). MS (ESI) m/z 476.3 (M+H)⁺

EXAMPLE 100

7-Cyclopentyl-2-[1'-(2-hydroxy-ethyl)-1',2',3',4',5',6'-hexahydro-[3,4']bipyridinyl-6-ylamino]-7H-pyrrolo[2,3-d]pyrimidine-6-carboxylic acid dimethylamide

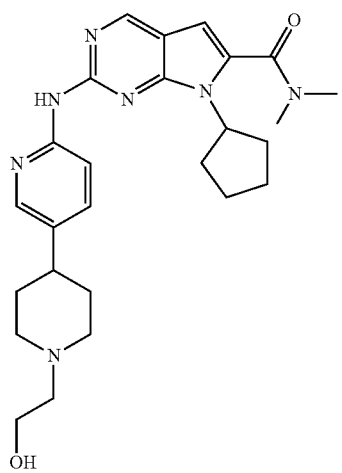 [SMILES: CN(C)C(=O)c1cc2cnc(Nc3ccc(C4CCN(CCO)CC4)cn3)nc2n1C1CCCC1]

Following General Procedure D, 7-cyclopentyl-2-(1',2',3',4',5',6'-hexahydro-[3,4']bipyridinyl-6-ylamino)-7H-pyrrolo[2,3-d]pyrimidine-6-carboxylic acid dimethylamide (63 mg, 0.15 mmol) and 2-bromo ethanol (90 mg, 0.72 mmol) to give 7-cyclopentyl-2-[1'-(2-hydroxy-ethyl)-1',2',3',4',5',6'-hexahydro-[3,4']bipyridinyl-6-ylamino]-7H-pyrrolo[2,3-d]pyrimidine-6-carboxylic acid dimethylamide (37 mg, 53%). MS (ESI) m/z 478.3 (M+H)⁺

EXAMPLE 45

4-[6-(7-Cyclopentyl-6-dimethylcarbamoyl-7H-pyrrolo[2,3-d]pyrimidin-2-ylamino)-pyridazin-3-yl]-piperazine-1-carboxylic acid tert-butyl ester

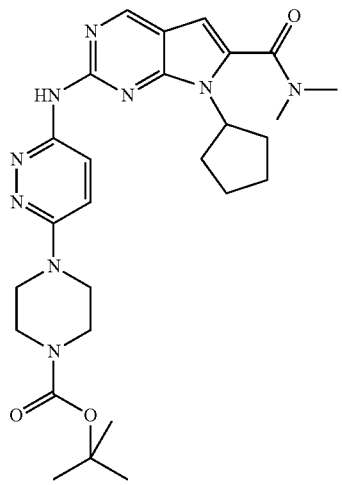 [SMILES: CN(C)C(=O)c1cc2cnc(Nc3ccc(N4CCN(C(=O)OC(C)(C)C)CC4)nn3)nc2n1C1CCCC1]

Following General Procedure D, 2-chloro-7-cyclopentyl-7H-pyrrolo[2,3-d]pyrimidine-6-carboxylic acid dimethylamide (200 mg, 0.68 mmol) and 4-(6-amino-pyridazin-3-yl)-piperazine-1-carboxylic acid tert-butyl ester (210 mg, 0.75 mmol) to give 4-[6-(7-cyclopentyl-6-dimethylcarbamoyl-7H-pyrrolo[2,3-d]pyrimidin-2-ylamino)-pyridazin-3-yl]-piperazine-1-carboxylic acid tert-butyl ester (150 mg, 46%). MS (ESI) m/z 536.3 (M+H)⁺

EXAMPLE 67

7-Cyclopentyl-2-(6-piperazin-1-yl-pyridazin-3-ylamino)-7H-pyrrolo[2,3-d]pyrimidine-6-carboxylic acid dimethylamide

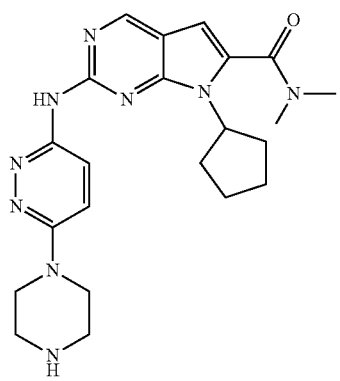

Following General Procedure A, 2-chloro-7-cyclopentyl-7H-pyrrolo[2,3-d]pyrimidine-6-carboxylic acid dimethylamide (150 mg, 0.28 mmol) gave 7-cyclopentyl-2-(6-piperazin-1-yl-pyridazin-3-ylamino)-7H-pyrrolo[2,3-d]pyrimidine-6-carboxyli c acid dimethylamide (2 mg, 2%). MS (ESI) m/z 436.3 (M+H)⁺

¹H NMR (400 MHz, DMSO-d6): 9.77 (1H, s), 8.76 (1H, s), 8.20 (1H, d), 7.39 (1H, d), 6.60 (1H, s), 5.75 (1H, s), 4.76-4.67 (1H, m), 3.52 (4H, s), 3.05 (6H, s), 2.94 (4H, s), 2.42-2.26 (2H, m), 1.97-1.88 (4H, m), 1.62-1.56 (2H, m).

EXAMPLE 70

7-Cyclopentyl-2-[6-(4-isopropyl-piperazin-1-yl)-pyridazin-3-ylamino]-7H-pyrrolo[2,3-d]pyrimidine-6-carboxylic acid dimethylamide

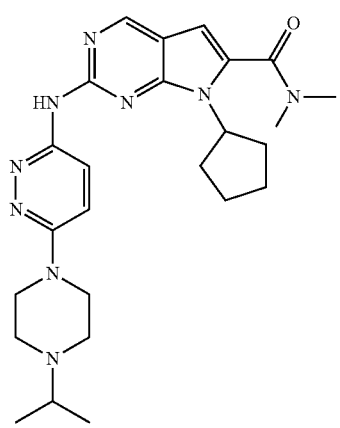

To a suspension of 7-cyclopentyl-2-(1',2',3',4',5',6'-hexahydro-[3,4']bipyridinyl-6-ylamino)-7H-pyrrolo[2,3-d]pyrimidine-6-carboxylic acid dimethylamide (100 mg, 0.23 mmol) in dichloromethane/acetone is added NaBH(OAc)₃ (488 mg, 2.3 mmol) followed by 3 drops of glacial acetic acid. After reaction is completed and concentrated. Diluted with 100 mL of H₂O and basified to pH12 with 50% NaOH solution dropwise (2 mL). Extracted with dichloromethane (3×100 mL), and concentrated to give 7-cyclopentyl-2-[6-(4-isopropyl-piperazin-1-yl)-pyridazin-3-ylamino]-7H-pyrrolo[2,3-d]pyrimidine-6-carboxylic acid dimethylamide (77 mg, 70%). MS (ESI) m/z 478.3 (M+H)⁺

EXAMPLE 37

7-Cyclopentyl-2-{6-[4-(2-hydroxy-ethyl)-piperazin-1-yl]-pyridazin-3-ylamino}-7H-pyrrolo[2,3-d]pyrimidine-6-carboxylic acid dimethylamide

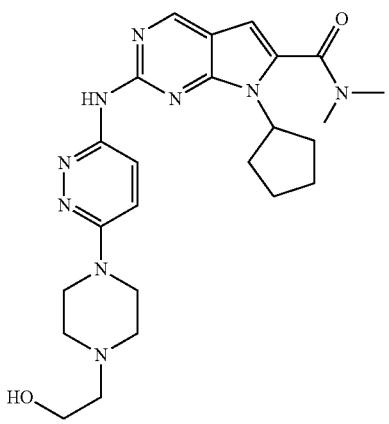 [SMILES: CN(C)C(=O)c1cc2cnc(Nc3ccc(N4CCN(CCO)CC4)nn3)nc2n1C1CCCC1]

Following General Procedure D, 7-cyclopentyl-2-(6-piperazin-1-yl-pyridazin-3-ylamino)-7H-pyrrolo[2,3-d]pyrimidine-6-carboxylic acid dimethylamide (100 mg, 0.229 mmol) and 2-bromo ethanol (143 mg, 1.14 mmol) gave 7-cyclopentyl-2-{6-[4-(2-hydroxy-ethyl)-piperazin-1-yl]-pyridazin-3-ylamino}-7H-pyrrolo[2,3-d]pyrimidine-6-carboxylic acid dimethylamide (14 mg, 13%).
MS (ESI) m/z 480.3 (M+H)⁺

EXAMPLE 48

7-Cyclopentyl-2-(3,4,5,6-tetrahydro-2H-[1,2']bipyrazinyl-5'-ylamino)-7H-pyrrolo[2,3-d]pyrimidine-6-carboxylic acid dimethylamide

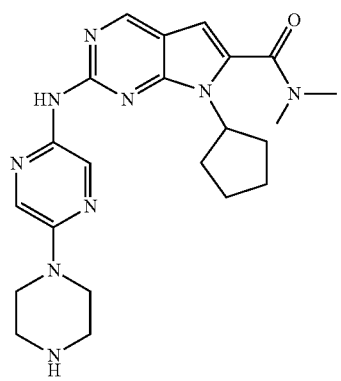 [SMILES: CN(C)C(=O)c1cc2cnc(Nc3cnc(N4CCNCC4)cn3)nc2n1C1CCCC1]

Following Buchwald Method B, 2-chloro-7-cyclopentyl-7H-pyrrolo[2,3-d]pyrimidine-6-carboxylic acid dimethylamide (100 mg, 0.342 mmol) and 5'-amino-2,3,5,6-tetrahydro-[1,2']bipyrazinyl-4-carboxylic acid tert-butyl ester (114 mg, 0.408 mmol), followed by deprotection using General Procedure A to give 7-cyclopentyl-2-(3,4,5,6-tetrahydro-2H-[1,2']bipyrazinyl-5'-ylamino)-7H-pyrrolo[2,3-d]pyrimidine-6-carboxylic acid dimethylamide (82 mg, 45%). MS (ESI) m/z 436.3 (M+H)⁺

EXAMPLE 15

7-Cyclopentyl-2-[4-(2-hydroxy-ethyl)-3,4,5,6-tetrahydro-2H-[1,2']bipyrazinyl-5'-ylamino]-7H-pyrrolo[2,3-d]pyrimidine-6-carboxylic acid dimethylamide

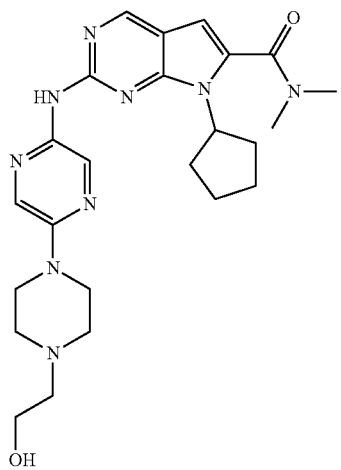 [SMILES: CN(C)C(=O)c1cc2cnc(Nc3cnc(N4CCN(CCO)CC4)cn3)nc2n1C1CCCC1]

Following General Procedure D, 7-cyclopentyl-2-(3,4,5,6-tetrahydro-2H-[1,2']bipyrazinyl-5'-ylamino)-7H-pyrrolo[2,3-d]pyrimidine-6-carboxylic acid dimethylamide (50 mg, 0.114 mmol) and 2-bromo ethanol (25 mg, 0.20 mmol) to give 7-cyclopentyl-2-[4-(2-hydroxy-ethyl)-3,4,5,6-tetrahydro-2H-[1,2']bipyrazinyl-5'-ylamino]-7H-pyrrolo[2,3-d]pyrimidine-6-carboxylic acid dimethylamide (30 mg, 54%). MS (ESI) m/z 480.6 (M+H)⁺
¹H NMR (400 MHz, CDCl₃): 9.19 (1H, s), 8.61 (1H, s), 7.76 (1H, s), 7.48 (1H, s), 7.19 (1H, s), 6.36 (1H, s), 4.80-4.68 (1H, m), 3.66-3.57 (2h, s), 3.54 (6H, s), 2.65 (3H, s), 2.59 (2h, s), 2.56-2.40 (2H, m), 2.03-1.93 (3h, m), 1.68-1.56 (4H, m).

EXAMPLE 40

7-(4-Hydroxy-4-methyl-cyclohexyl)-2-(pyridin-2-ylamino)-7H-pyrrolo[2,3-d]pyrimidine-6-carboxylic acid dimethylamide

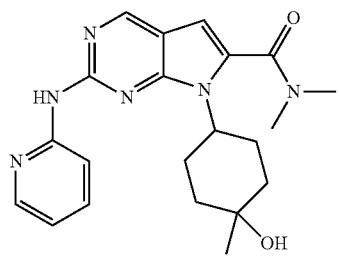 [SMILES: CN(C)C(=O)c1cc2cnc(Nc3ccccn3)nc2n1C1CCC(C)(O)CC1]

To a solution of 7-(4-oxo-cyclohexyl)-2-(pyridin-2-ylamino)-7H-pyrrolo[2,3-d]pyrimidine-6-carboxylic acid dimethylamide (25 mg, 0.066 mmol) in THF is added 20 drops of MeMgI. After reaction is completed, added 25 mL of water then 30 mL of aqueous sodium bicarbonate. Extraction with dichloromethane (3×50 mL) and concentrated to give a mixture of diastereomers. Preparative HPLC to give 7-(4-hydroxy-4-methyl-cyclohexyl)-2-(pyridin-2-ylamino)-7H-pyrrolo[2,3-d]pyrimidine-6-carboxylic acid dimethylamide (2 mg, 4%). MS (ESI) m/z 395.3 (M+H)+

EXAMPLE 58

7-Cyclopentyl-2-(5-piperazin-1-yl-pyridin-2-ylamino)-7H-pyrrolo[2,3-d]pyrimidine-6-carboxylic acid methylamide

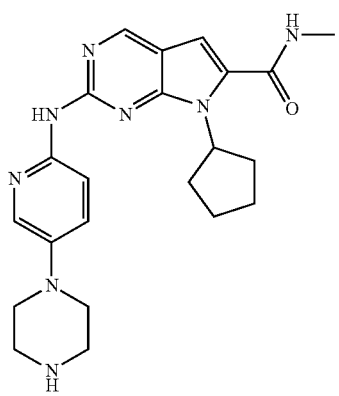 [SMILES: CNC(=O)c1cc2cnc(Nc3ccc(N4CCNCC4)cn3)nc2n1C1CCCC1]

Following Buchwald Method B, 2-chloro-7-cyclopentyl-7H-pyrrolo[2,3-d]pyrimidine-6-carboxylic acid methylamide (500 mg, 1.80 mmol) and 4-(6-amino-pyridin-3-yl)-piperazine-1-carboxylic acid tert-butyl ester (550 mg, 1.98 mmol) gave 7-cyclopentyl-2-(5-piperazin-1-yl-pyridin-2-ylamino)-7H-pyrrolo[2,3-d]pyrimidine-6-carboxylic acid methylamide (580 mg, 77%). MS (ESI) m/z 421.2 (M+H)+
1H NMR (400 MHz, DMSO-d6): 8.72 (1H, s), 8.38 (1H, d), 8.02 (1H, s), 7.77 (1H, s), 7.36 (1H, dd), 6.67 (1H, s), 6.16-6.10 (1H, m), 5.50-5.48 (1H, m), 3.15 (3H, d), 3.03 (2H, d), 2.68-2.58 (2H, m), 2.14-2.05 (4H, m), 1.80-1.61 (8H, m).

EXAMPLE 51

7-Cyclopentyl-2-[5-(4-isopropyl-piperazin-1-yl)-pyridin-2-ylamino]-7H-pyrrolo[2,3-d]pyrimidine-6-carboxylic acid methylamide

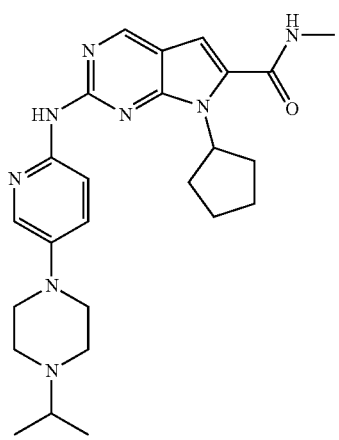 [SMILES: CNC(=O)c1cc2cnc(Nc3ccc(N4CCN(C(C)C)CC4)cn3)nc2n1C1CCCC1]

To a suspension of 2-chloro-7-cyclopentyl-7H-pyrrolo[2,3-d]pyrimidine-6-carboxylic acid methylamide (500 mg, 1.20 mmol) in acetone is added NaBH(OAc)3 (2.5 g, 12 mmol) followed by 15 drops of glacial acetic acid. After reaction is completed and concentrated. Diluted with 250 mL of H2O and basified to pH12 with 50% NaOH solution dropwise. Extracted with dichloromethane (3×250 mL) and concentrated to give 7-cyclopentyl-2-[5-(4-isopropyl-piperazin-1-yl)-pyridin-2-ylamino]-7H-pyrrolo[2,3-d]pyrimidine-6-carboxylic acid methylamide (277 mg, 50%). MS (ESI) m/z 463.4 (M+H)+

EXAMPLE 11

(7-Cyclopentyl-6-oxazol-5-yl-7H-pyrrolo[2,3-d]pyrimidin-2-yl)-(5-piperazin-1-yl-pyridin-2-yl)-amine

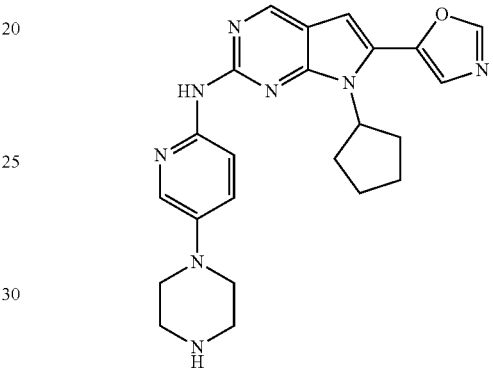

Following Buchwald Method B, 2-chloro-7-cyclopentyl-6-oxazol-5-y-1-7H-pyrrolo[2,3-d]pyrimidine (70 mg, 0.24 mmol) and 4-(6-amino-pyridin-3-yl)-piperazine-1-carboxylic acid tert-butyl ester (74 mg, 0.27 mmol), followed by deprotection using General Procedure A to give (7-cyclopentyl-6-oxazol-5-yl-7H-pyrrolo[2,3-d]pyrimidin-2-yl)-(5-piperazin-1-yl-pyridin-2-yl)-amine (25 mg, 24%). MS (ESI) m/z 431.2 (M+H)+
1H NMR (400 MHz, DMSO-d6): 9.33 (1H, s), 8.78 (1H, s), 8.59 (1H, s), 8.13 (1H, d), 7.98 (1H, d), 7.61 (1H, s), 7.40 (1H, dd), 6.78 (1H, s), 4.70-4.77 (1H, m), 3.04-3.01 (4H, m), 2.86-2.84 (4H, m), 2.03-2.01 (6H, m), 1.68-1.67 (2H).

EXAMPLE 18

(7-Cyclopentyl-6-oxazol-5-yl-7H-pyrrolo[2,3-d]pyrimidin-2-yl)-(5-piperazin-1-ylmethyl-pyridin-2-yl)-amine

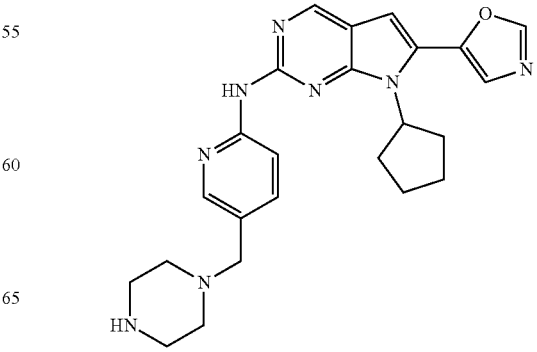

Following Buchwald Method B, 2-chloro-7-cyclopentyl-6-oxazol-5-y-1-7H-pyrrolo[2,3-d]pyrimidine (100 mg, 0.346 mmol) and 4-(6-amino-pyridin-3-ylmethyl)-piperazine-1-carboxylic acid tert-butyl ester (106 mg, 0.363 mmol), followed by deprotection using General Procedure A to give (7-cyclopentyl-6-oxazol-5-yl-7H-pyrrolo[2,3-d]pyrimidin-2-yl)-(5-piperazin-1-ylmethyl-pyridin-2-yl)-amine (23 mg, 15%). MS (ESI) m/z 445.2 (M+H)⁺

EXAMPLE 109

7-cyclopentyl-2-[5-(2-oxopiperazin-1-yl)pyridin-2-ylamino]-7H-pyrrolo[2,3-d]pyrimidine-6-carboxylic acid dimethylamide

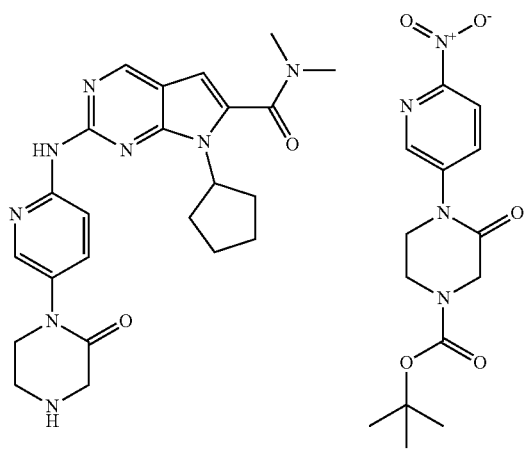

A mixture of 5-bromo-2-nitropyridine (200 mg, 1 mmol), 1-Boc-3-oxopiperazine (240 mg, 1.2 mmol), Xantphos (43 mg, 0.075 mmol), cesium carbonate (326 mg, 1 mmol), palladium(II) acetate (11 mg, 0.049 mmol) in dioxane (5.5 mL) is heated to 120° C. in a Personal Chemistry microwave apparatus for 0.5 h. TLC and LCMS analysis indicates completion of the reaction. The reaction mixture is filtered through Celite, evaporated in vacuo, and the residue is partitioned between water and ethyl acetate. The organic layer is washed with brine, dried (Na2SO4) and evaporated in vacuo. Purification by flash chromatography on silica (ethyl acetate) provides 4-(6-Nitropyridin-3-yl)-3-oxopiperazine-1-carboxylic acid tert-butyl ester as a pale brown solid (248 mg, 77%). MS (ESI) m/z 323 [M+H+].

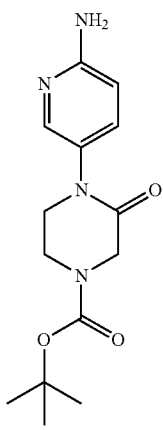 [SMILES: CC(C)(C)OC(=O)N1CCN(c2ccc(N)nc2)C(=O)C1]

By repeating procedures described in Example B, 4-(6-nitropyridin-3-yl)-3-oxopiperazine-1-carboxylic acid tert-butyl ester (240 mg, 0.74 mmol) gives 4-(6-aminopyridin-3-yl)-3-oxopiperazine-1-carboxylic acid tert-butyl ester (225 mg). MS (ESI) m/z 293 [M+H]+.

A mixture of 2-Chloro-7-cyclopentyl-7H-pyrrolo[2,3-d]pyrimidine-6-carboxylic acid dimethylamide (225 mg, 0.77 mmol), 4-(6-aminopyridin-3-yl)-3-oxopiperazine-1-carboxylic acid tert-butyl ester (204 mg, 0.69 mmol), BINAP (24 mg, 0.038 mmol), palladium(II) acetate (6 mg, 0.027 mmol) and cesium carbonate (340 mg, 1.05 mmol) in dioxin (4 mL) is flushed with nitrogen and heated to 100° C. overnight. Additional palladium(II) acetate (6 mg, 0.027 mmol) and BINAP (24 mg, 0.038) are added and heating is continued at 110° C. for 2 h at which point LCMS and TLC analysis indicates completion of the reaction. The solvent is removed in vacuo and the residue is stirred in water with sonication in an ultrasonic bath. The suspension is filtered and the filter cake is washed with heptane. Drying in vacuo provides 4-[6-(7-Cyclopentyl-6-dimethylcarbamoyl-7H-pyrrolo[2,3-d]pyrimidin-2-ylamino)-pyridin-3-yl]-3-oxo-piperazine-1-carboxylic acid tert-butyl ester as a tan solid (350 mg, 83%) MS (ESI) m/z=549 [M+H]+.

Following General Procedure A 4-[6-(7-Cyclopentyl-6-dimethylcarbamoyl-7H-pyrrolo[2,3-d]pyrimidin-2-ylamino)-pyridin-3-yl]-3-oxo-piperazine-1-carboxylic acid tert-butyl ester gives 7-cyclopentyl-2-[5-(2-oxopiperazin-1-yl)pyridin-2-ylamino]-7H-pyrrolo[2,3-d]pyrimidine-6-carboxylic acid dimethylamide (10 mg, 3.5%) MS (ESI)=448 [M+H]+.

EXAMPLE 110

7-Cyclopentyl-2-(5-morpholin-4-yl-pyridin-2-ylamino)-7H-pyrrolo[2,3-d]pyrimidine-6-carboxylic acid dimethylamide

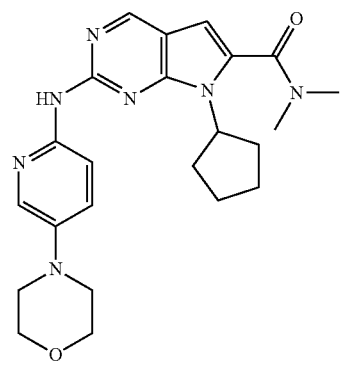 [SMILES: CN(C)C(=O)c1cc2cnc(Nc3ccc(N4CCOCC4)cn3)nc2n1C1CCCC1]

A mixture of 5-Morpholin-4-yl-pyridin-2-ylamine (0.61 g, 3.4 mmol; prepared using methods similar to those described in Example A and Example B), 2-Chloro-7-cyclopentyl-7H-pyrrolo[2,3-d]pyrimidine-6-carboxylic acid dimethylamide (1.00 g, 3.4 mmol), BINAP (106 mg, 0.17 mmol), palladium (II) acetate (38 mg, 0.17 mmol) and cesium carbonate (1.6 g, 4.9 mmol) in dioxan (20 mL) is heated to 110° C. for 6 h. After cooling to room temperature, heptane (30 mL) is added and the mixture is stirred for 1 h. The resulting suspension is filtered and the filtercake is suspended in water with vigorous stirring. The resulting suspension is again filtered and the filtercake is washed with water then diethylether before being dried in vacuo to provide 7-Cyclopentyl-2-(5-morpholin-4-yl-pyridin-2-ylamino)-7H-pyrrolo[2,3-d]pyrimidine-6-carboxylic acid dimethylamide as a tan solid (1.30 g, 88%) MS (ESI)=436.1 [M+H]+.

The following tables 1 and 2 of compounds are examples of compounds which may be made using the synthetic routes exemplified in the experimental section. While the synthesis of all compounds is not shown, one of skill in the art may be able to make each compound using the synthetic routes shown.

TABLE 1

| Compound | Example Number |
|---|---|
| 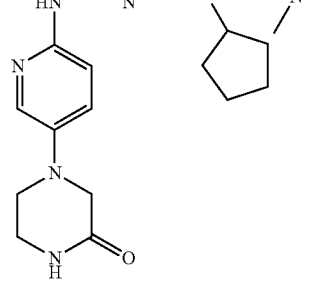 | 1 |
| | 2 |
| | 3 |

TABLE 1-continued

| Compound | Example Number |
|---|---|
| 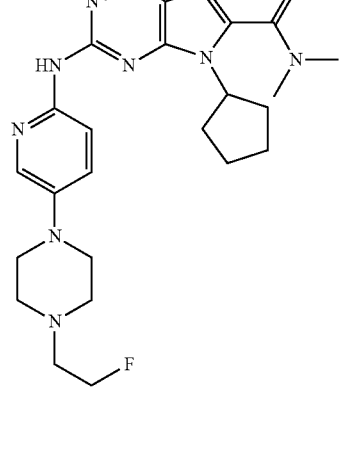 | 4 |
| | 5 |
| 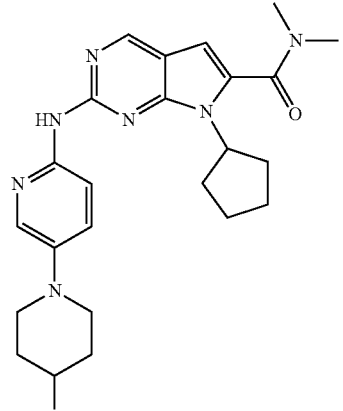 | 6 |

TABLE 1-continued
| Compound | Example Number |
|---|---|
| 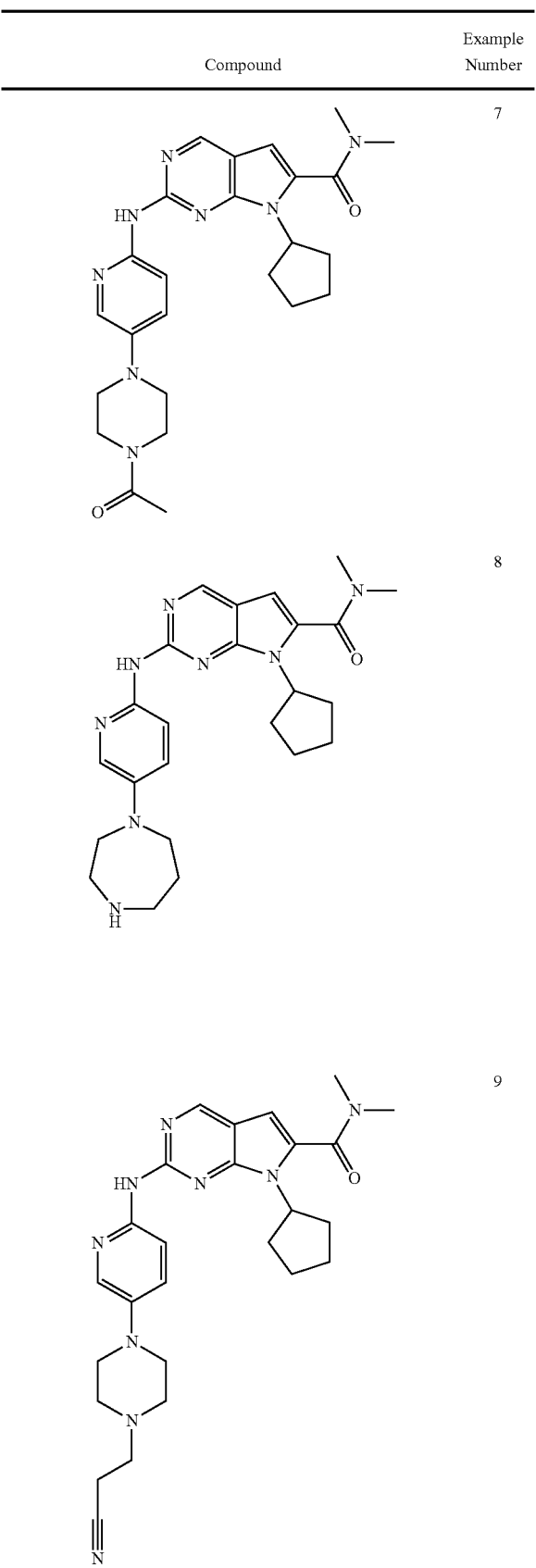 | 7 |
| | 8 |
| | 9 |
TABLE 1-continued
| Compound | Example Number |
|---|---|
| 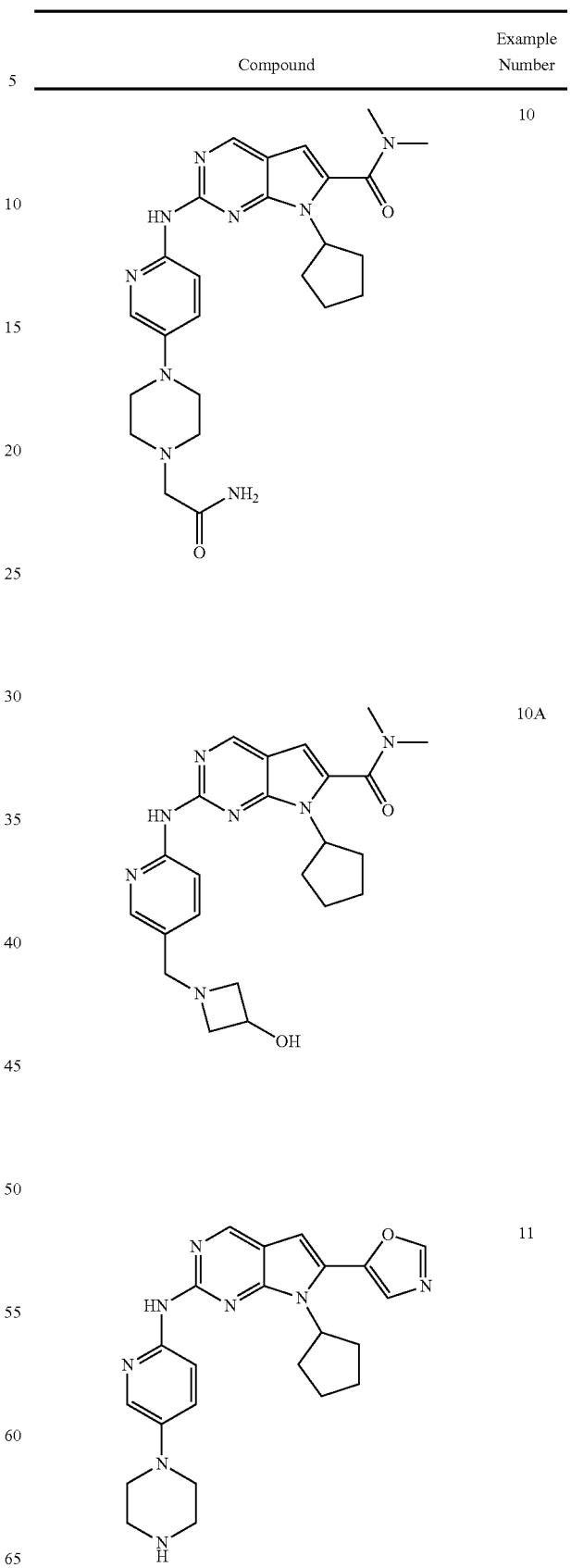 | 10 |
| | 10A |
| | 11 |

TABLE 1-continued
| Compound | Example Number |
|---|---|
| 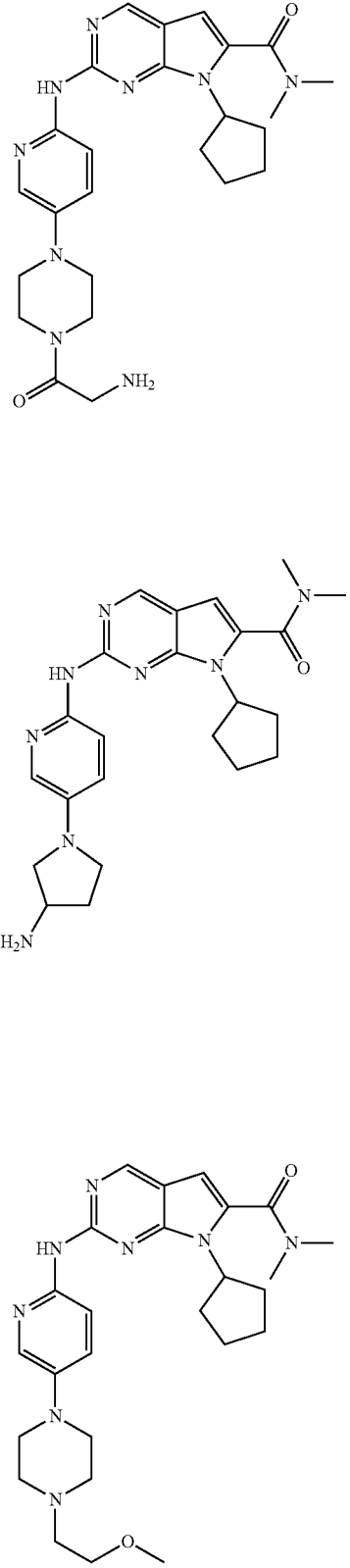 | 12 |
| | 13 |
| | 14 |
TABLE 1-continued
| Compound | Example Number |
|---|---|
| 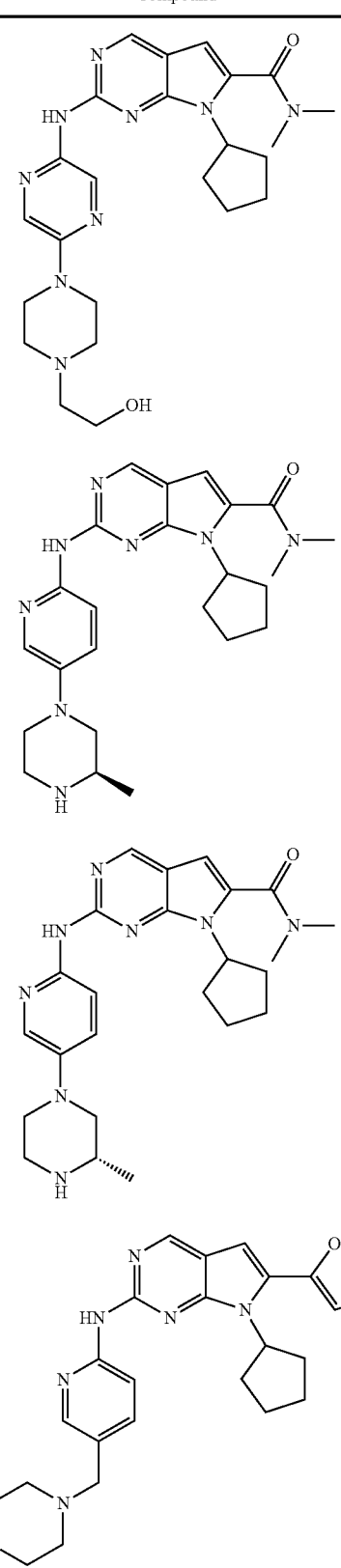 | 15 |
| | 16 |
| | 17 |
| | 18 |

TABLE 1-continued
| Compound | Example Number |
|---|---|
| 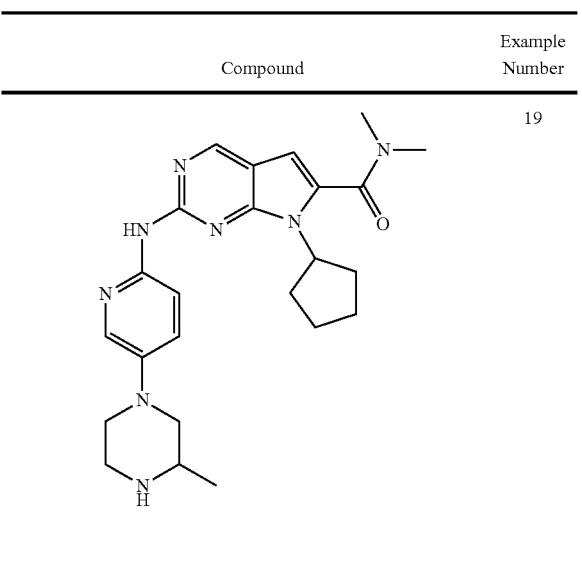 | 19 |
| 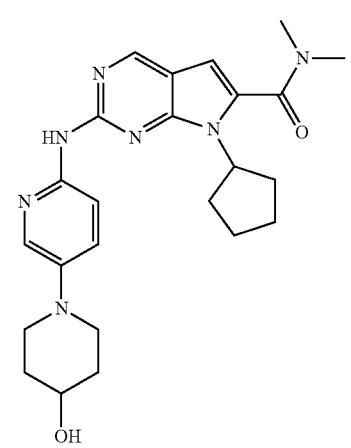 [SMILES: CN(C)C(=O)c1cc2cnc(Nc3ccc(N4CCC(O)CC4)cn3)nc2n1C1CCCC1] | 20 |
| 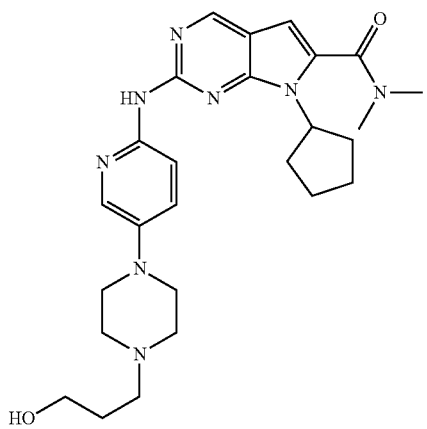 [SMILES: CN(C)C(=O)c1cc2cnc(Nc3ccc(N4CCN(CCCO)CC4)cn3)nc2n1C1CCCC1] | 21 |
TABLE 1-continued
| Compound | Example Number |
|---|---|
| 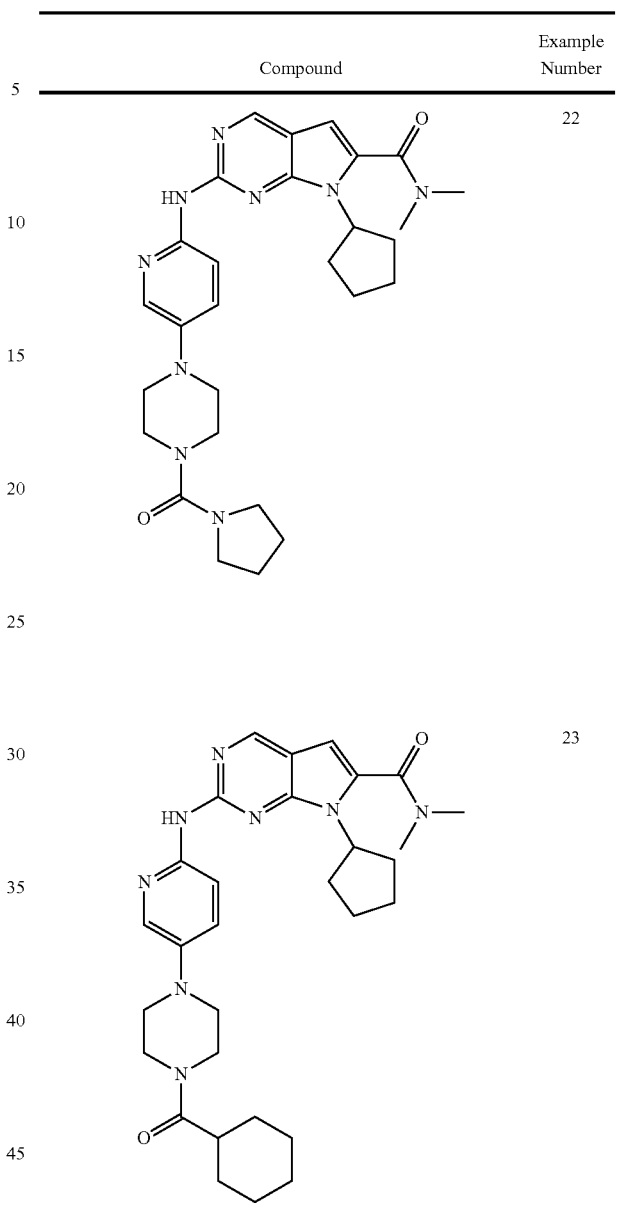 | 22 |
| | 23 |
| 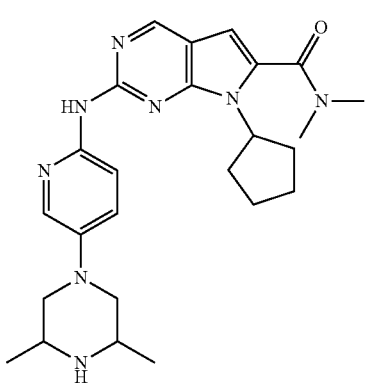 | 24 |

TABLE 1-continued
| Compound | Example Number |
|---|---|
| 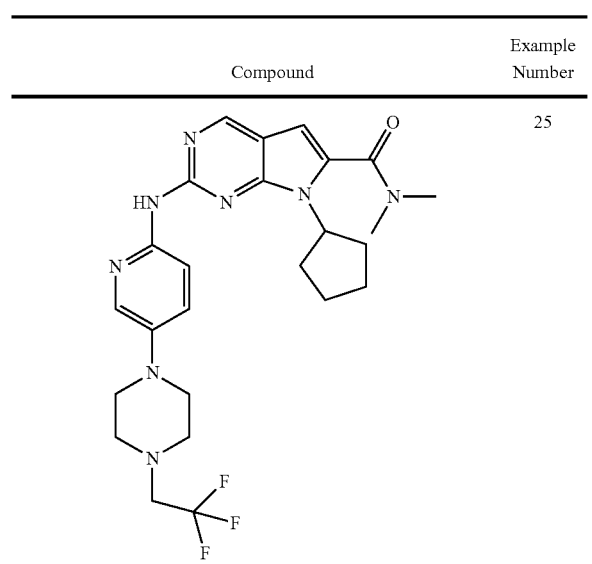 | 25 |
| | 26 |
| | 27 |
TABLE 1-continued
| Compound | Example Number |
|---|---|
| 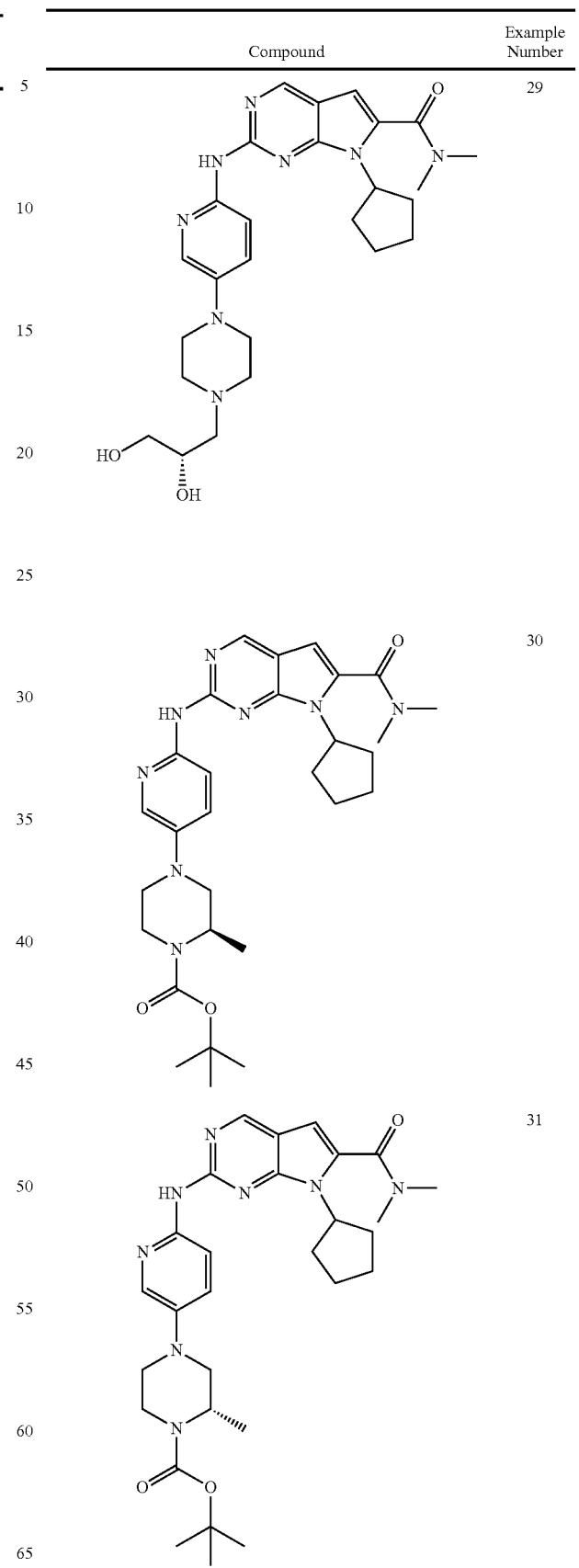 | 29 |
| | 30 |
| | 31 |

TABLE 1-continued
| Compound | Example Number |
|---|---|
| 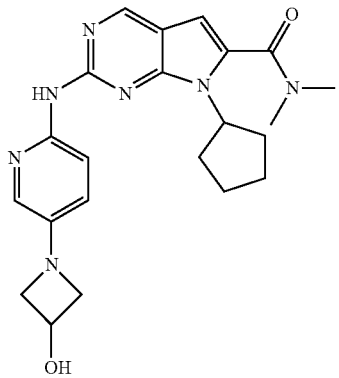 [SMILES: CN(C)C(=O)c1cc2cnc(Nc3ccc(N4CC(O)C4)cn3)nc2n1C1CCCC1] | 32 |
| 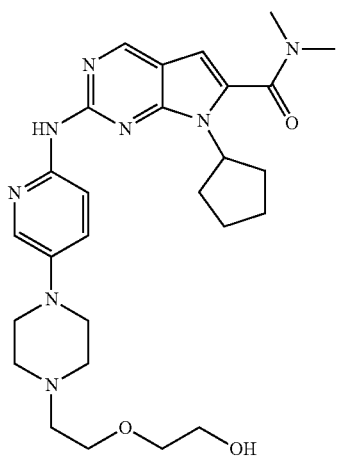 [SMILES: CN(C)C(=O)c1cc2cnc(Nc3ccc(N4CCN(CCOCCO)CC4)cn3)nc2n1C1CCCC1] | 33 |
| 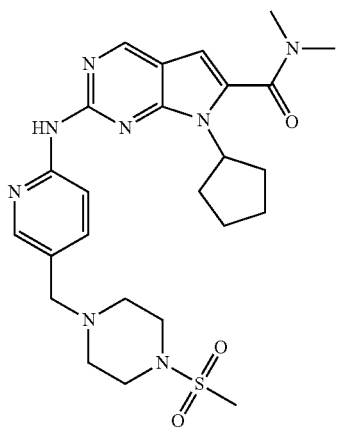 [SMILES: CN(C)C(=O)c1cc2cnc(Nc3ccc(CN4CCN(S(C)(=O)=O)CC4)cn3)nc2n1C1CCCC1] | 34 |
TABLE 1-continued
| Compound | Example Number |
|---|---|
| 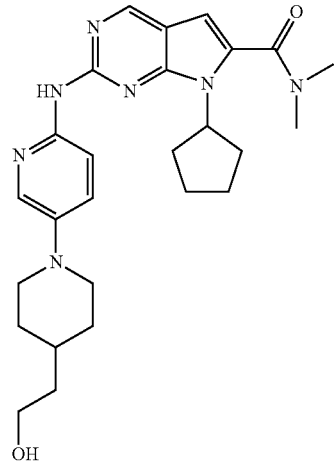 [SMILES: CN(C)C(=O)c1cc2cnc(Nc3ccc(N4CCC(CCO)CC4)cn3)nc2n1C1CCCC1] | 35 |
| 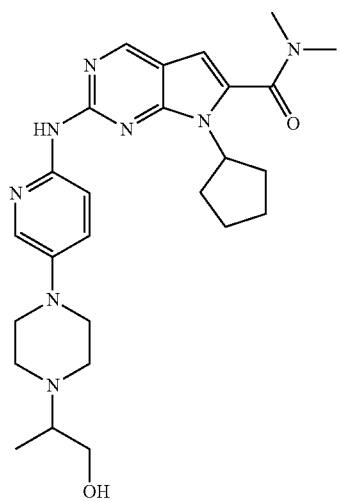 [SMILES: CC(CO)N1CCN(c2ccc(Nc3ncc4cc(C(=O)N(C)C)n(C5CCCC5)c4n3)nc2)CC1] | 36 |
| 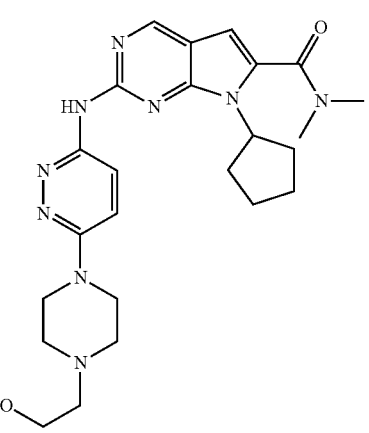 | 37 |

TABLE 1-continued
| Compound | Example Number |
|---|---|
| 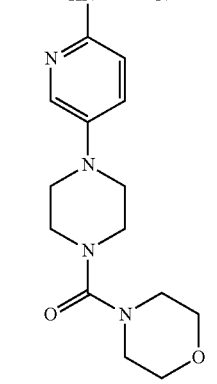 | 38 |
| 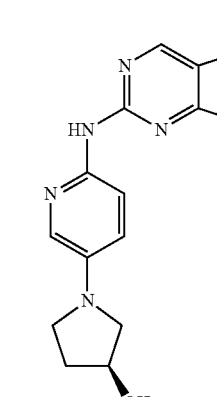 | 39 |
| 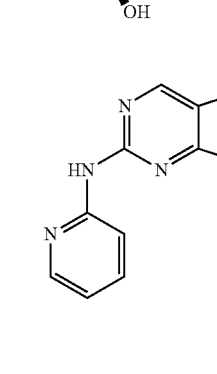 | 40 |
| 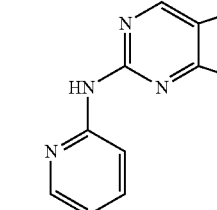 | 41 |
TABLE 1-continued
| Compound | Example Number |
|---|---|
| 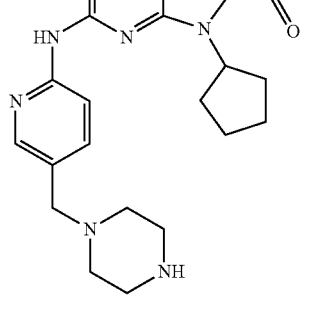 | 42 |
| 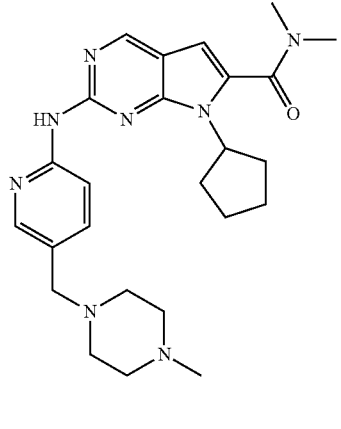 [SMILES: CN1CCN(Cc2ccc(Nc3ncc4cc(C(=O)N(C)C)n(C5CCCC5)c4n3)nc2)CC1] | 43 |
| 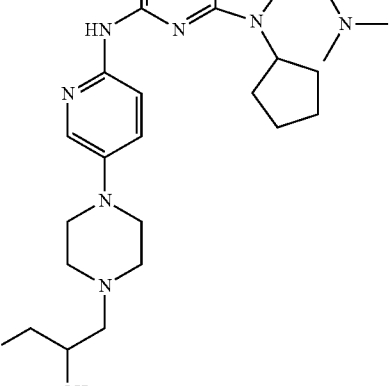 | 44 |

TABLE 1-continued
| Compound | Example Number |
|---|---|
| 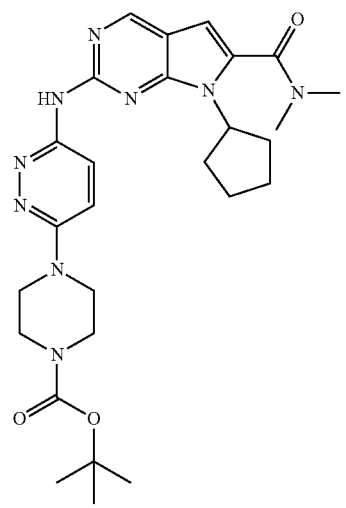 [SMILES: CN(C)C(=O)c1cc2cnc(Nc3ccc(N4CCN(C(=O)OC(C)(C)C)CC4)nn3)nc2n1C1CCCC1] | 45 |
| 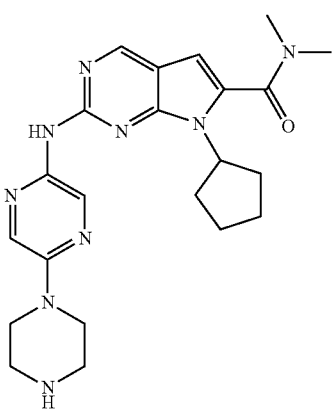 [SMILES: CN(C)C(=O)c1cc2cnc(Nc3cnc(N4CCNCC4)cn3)nc2n1C1CCCC1] | 48 |
| | 46 |
| | 49 |
| 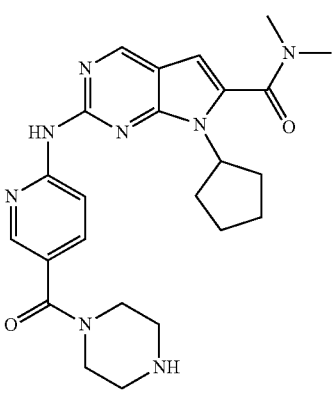 [SMILES: CN(C)C(=O)c1cc2cnc(Nc3ccc(C(=O)N4CCNCC4)cn3)nc2n1C1CCCC1] | |
| | 47 |
| | 50 |
| 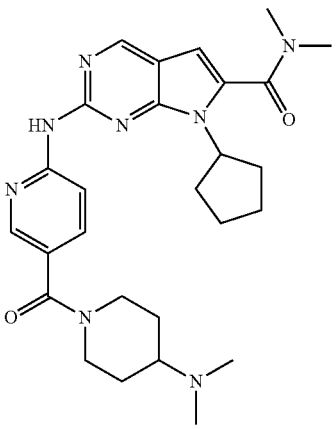 [SMILES: CN(C)C(=O)c1cc2cnc(Nc3ccc(C(=O)N4CCC(N(C)C)CC4)cn3)nc2n1C1CCCC1] | |

TABLE 1-continued
| Compound | Example Number |
|---|---|
| 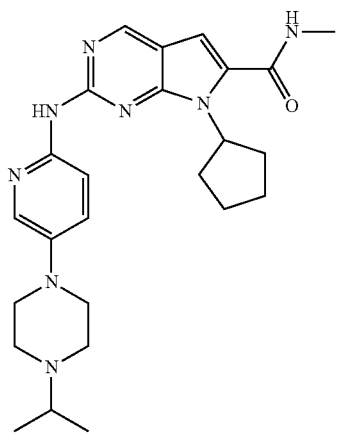 [SMILES: CNC(=O)c1cc2cnc(Nc3ccc(N4CCN(C(C)C)CC4)cn3)nc2n1C1CCCC1] | 51 |
| 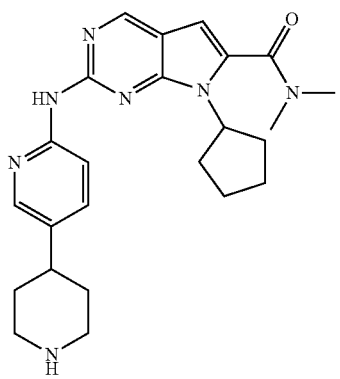 [SMILES: CN(C)C(=O)c1cc2cnc(Nc3ccc(C4CCNCC4)cn3)nc2n1C1CCCC1] | 52 |
| 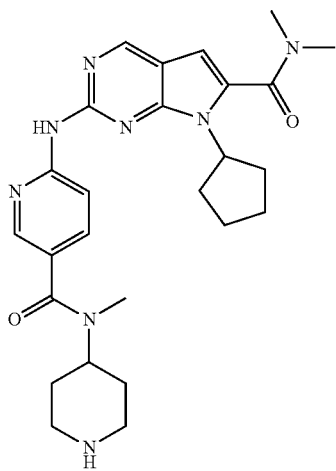 [SMILES: CN(C)C(=O)c1cc2cnc(Nc3ccc(C(=O)N(C)C4CCNCC4)cn3)nc2n1C1CCCC1] | 53 |
TABLE 1-continued
| Compound | Example Number |
|---|---|
| 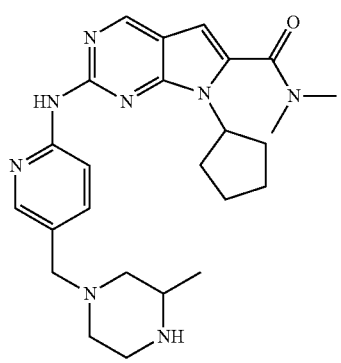 [SMILES: CC1CN(Cc2ccc(Nc3ncc4cc(C(=O)N(C)C)n(C5CCCC5)c4n3)nc2)CCN1] | 54 |
| 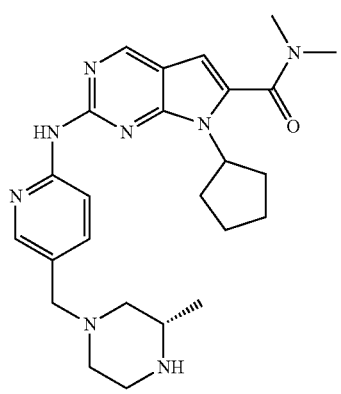 [SMILES: C[C@H]1CN(Cc2ccc(Nc3ncc4cc(C(=O)N(C)C)n(C5CCCC5)c4n3)nc2)CCN1] | 55 |
| 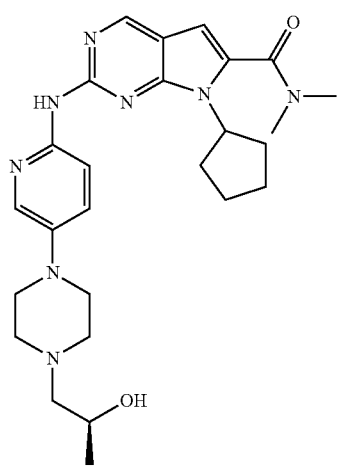 [SMILES: C[C@H](O)CN1CCN(c2ccc(Nc3ncc4cc(C(=O)N(C)C)n(C5CCCC5)c4n3)nc2)CC1] | 56 |

TABLE 1-continued
| Compound | Example Number |
|---|---|
| 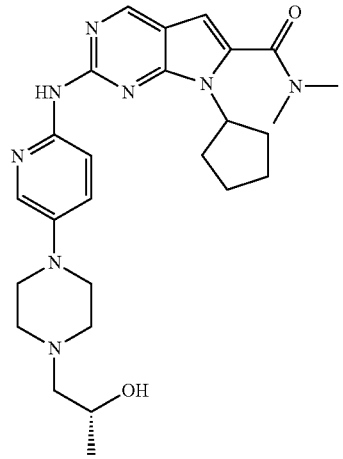 [SMILES: C[C@@H](O)CN1CCN(c2ccc(Nc3ncc4cc(C(=O)N(C)C)n(C5CCCC5)c4n3)nc2)CC1] | 57 |
| 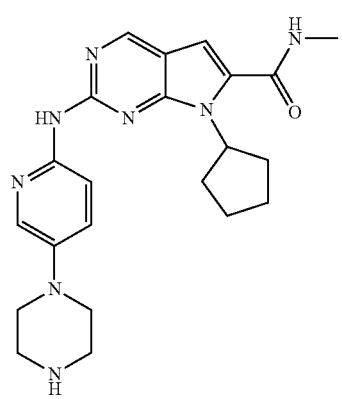 [SMILES: CNC(=O)c1cc2cnc(Nc3ccc(N4CCNCC4)cn3)nc2n1C1CCCC1] | 58 |
| 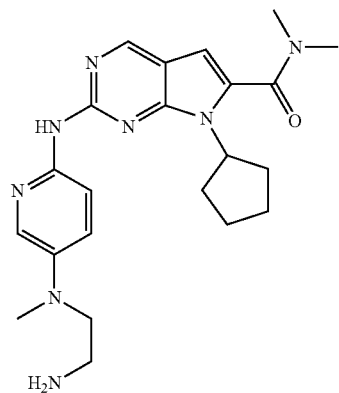 [SMILES: CN(C)C(=O)c1cc2cnc(Nc3ccc(N(C)CCN)cn3)nc2n1C1CCCC1] | 59 |
TABLE 1-continued
| Compound | Example Number |
|---|---|
| 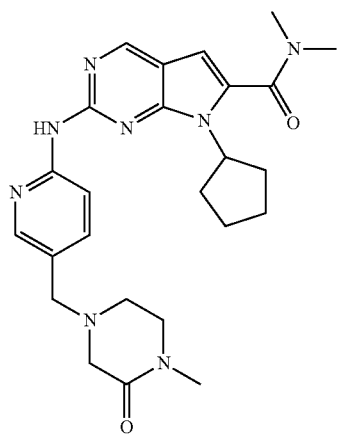 [SMILES: CN(C)C(=O)c1cc2cnc(Nc3ccc(CN4CCN(C)C(=O)C4)cn3)nc2n1C1CCCC1] | 60 |
| 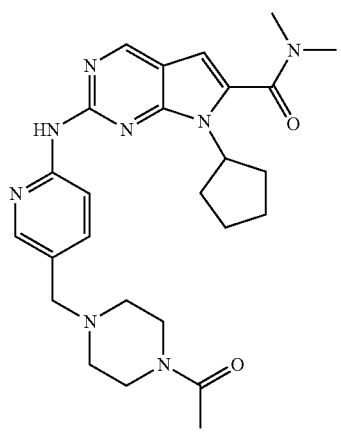 [SMILES: CC(=O)N1CCN(Cc2ccc(Nc3ncc4cc(C(=O)N(C)C)n(C5CCCC5)c4n3)nc2)CC1] | 61 |
| | 62 |

TABLE 1-continued
| Compound | Example Number |
|---|---|
| 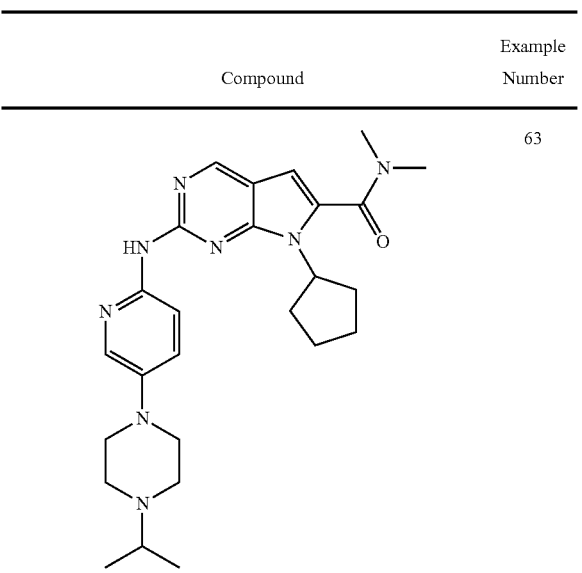 | 63 |
| | 64 |
| | 65 |
TABLE 1-continued
| Compound | Example Number |
|---|---|
| 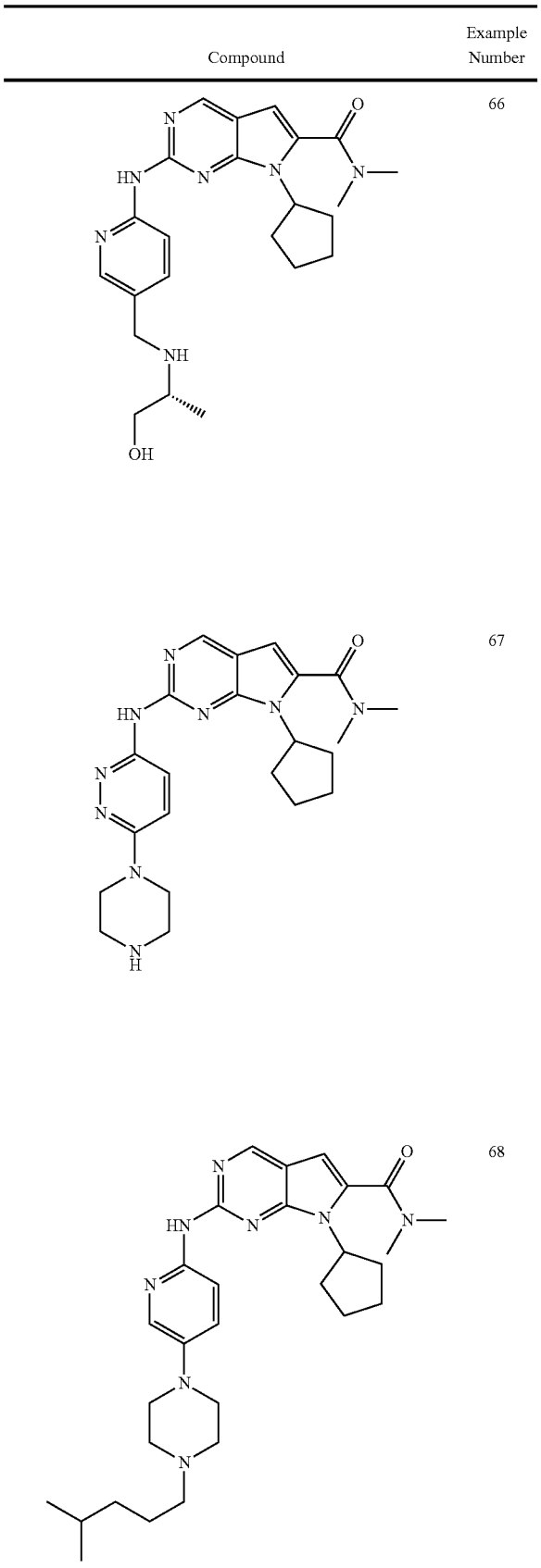 | 66 |
| | 67 |
| | 68 |

TABLE 1-continued

| Compound | Example Number |
|---|---|
| (structure) | 69 |
| (structure) | 70 |
| (structure) | 71 |
| (structure) | 72 |
| (structure) | 73 |
| (structure) | 74 |
| (structure) | 75 |

TABLE 1-continued

| Compound | Example Number |
|---|---|
| (structure) | 76 |
| (structure) | 77 |
| (structure) | 78 |
| (structure) | 79 |
| (structure) | 80 |
| (structure) | 81 |

TABLE 1-continued
| Compound | Example Number |
|---|---|
| 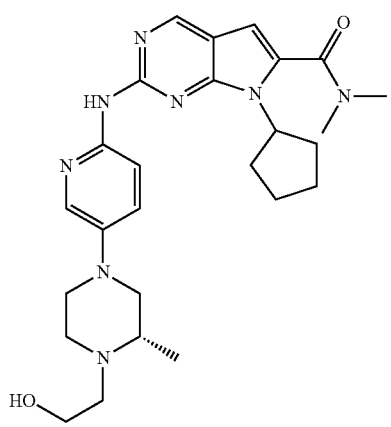 [SMILES: C[C@H]1CN(c2ccc(Nc3ncc4cc(C(=O)N(C)C)n(C5CCCC5)c4n3)nc2)CCN1CCO] | 82 |
| | 83 |
| | 84 |
| 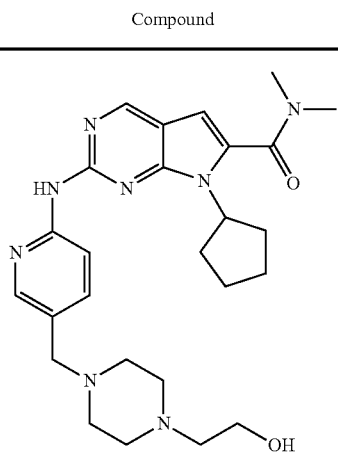 | 85 |
| 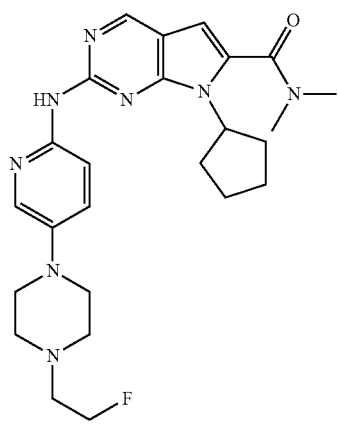 [SMILES: CN(C)C(=O)c1cc2cnc(Nc3ccc(N4CCN(CCF)CC4)cn3)nc2n1C1CCCC1] | 86 |
| 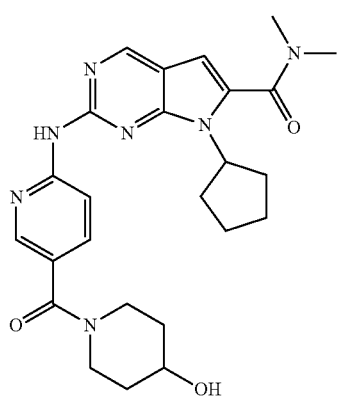 [SMILES: CN(C)C(=O)c1cc2cnc(Nc3ccc(C(=O)N4CCC(O)CC4)cn3)nc2n1C1CCCC1] | 87 |

TABLE 1-continued
| Compound | Example Number |
|---|---|
| 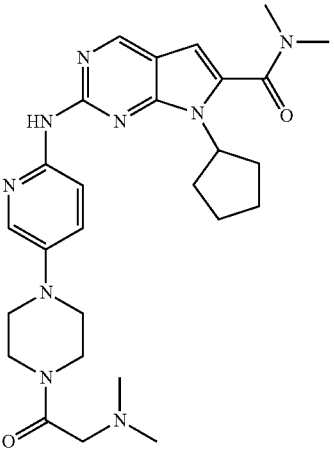 [SMILES: CN(C)CC(=O)N1CCN(c2ccc(Nc3ncc4cc(C(=O)N(C)C)n(C5CCCC5)c4n3)nc2)CC1] | 88 |
| 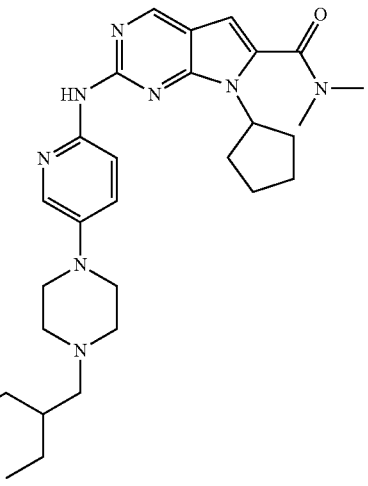 | 89 |
| 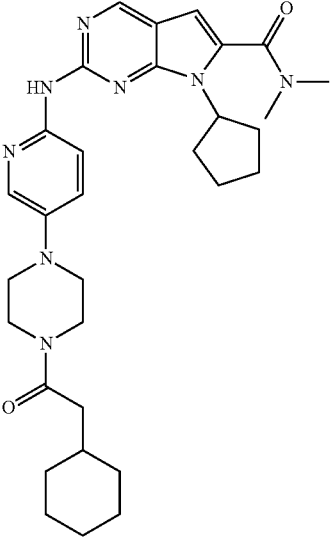 [SMILES: CN(C)C(=O)c1cc2cnc(Nc3ccc(N4CCN(C(=O)CC5CCCCC5)CC4)cn3)nc2n1C1CCCC1] | 90 |
TABLE 1-continued
| Compound | Example Number |
|---|---|
| 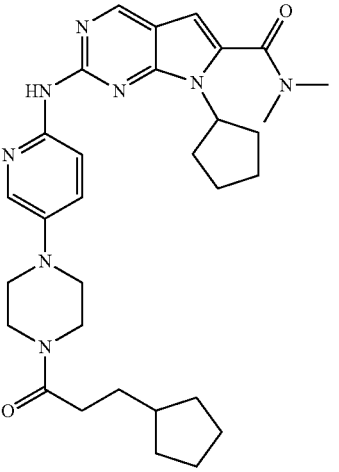 [SMILES: CN(C)C(=O)c1cc2cnc(Nc3ccc(N4CCN(C(=O)CCC5CCCC5)CC4)cn3)nc2n1C1CCCC1] | 91 |
| 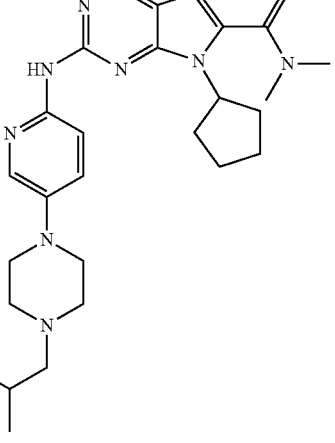 | 92 |
| 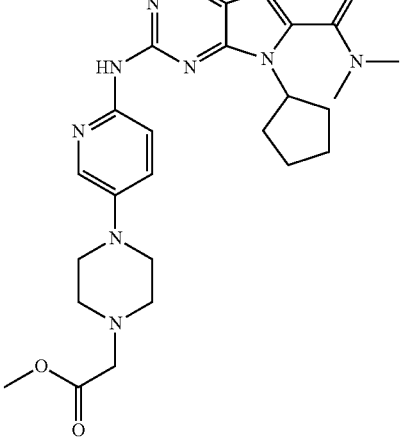 | 93 |

TABLE 1-continued
| Compound | Example Number |
|---|---|
| 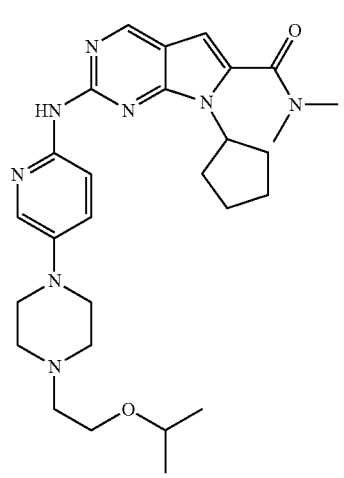 [SMILES: CC(C)OCCN1CCN(c2ccc(Nc3ncc4cc(C(=O)N(C)C)n(C5CCCC5)c4n3)nc2)CC1] | 94 |
| 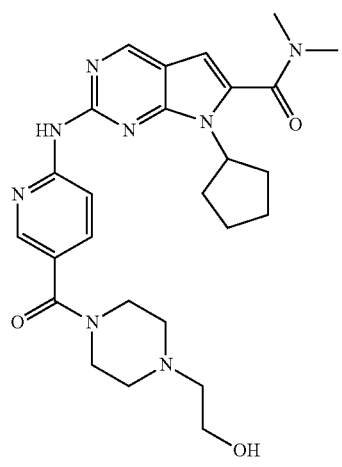 [SMILES: CN(C)C(=O)c1cc2cnc(Nc3ccc(C(=O)N4CCN(CCO)CC4)cn3)nc2n1C1CCCC1] | 95 |
TABLE 1-continued
| Compound | Example Number |
|---|---|
| 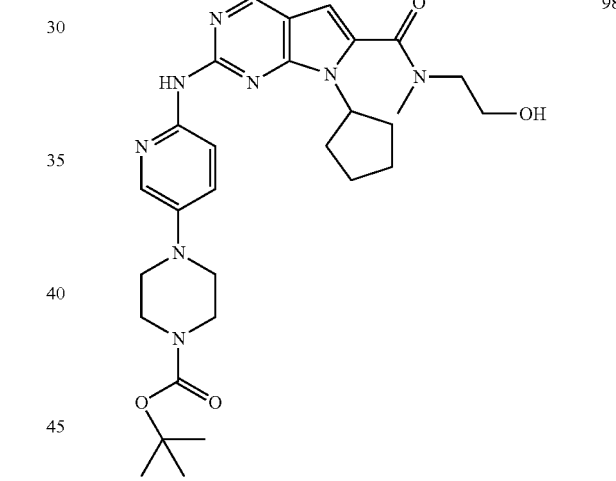 | 97 |
| 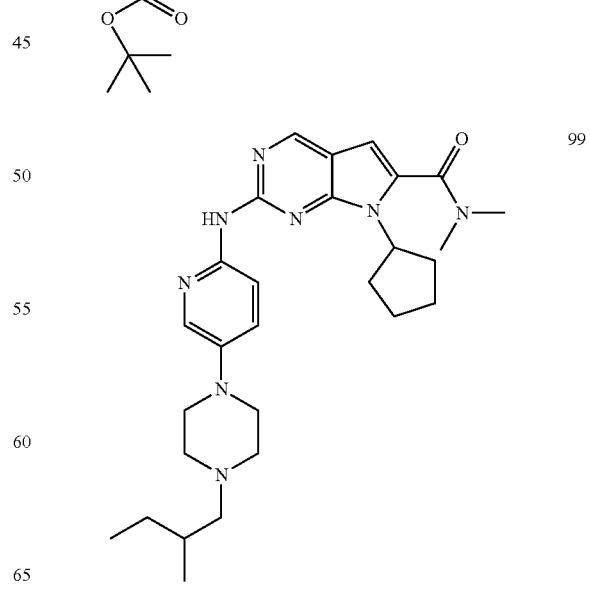 | 98 |

TABLE 1-continued
| Compound | Example Number |
|---|---|
| 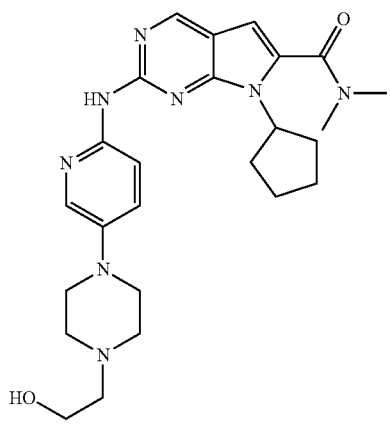 | 100 |
| 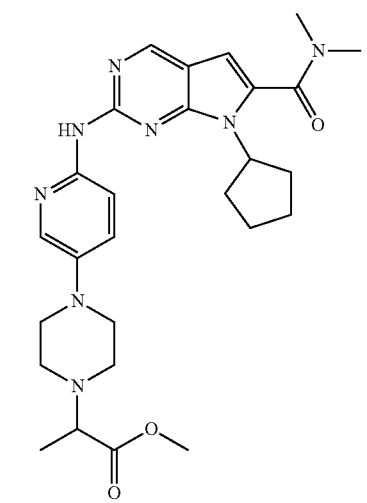 [SMILES: COC(=O)C(C)N1CCN(c2ccc(Nc3ncc4cc(C(=O)N(C)C)n(C5CCCC5)c4n3)nc2)CC1] | 101 |
| 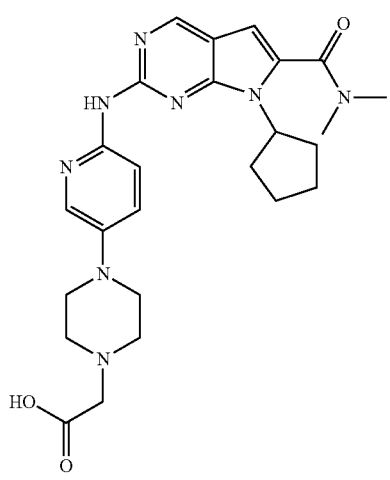 [SMILES: CN(C)C(=O)c1cc2cnc(Nc3ccc(N4CCN(CC(=O)O)CC4)cn3)nc2n1C1CCCC1] | 102 |
| 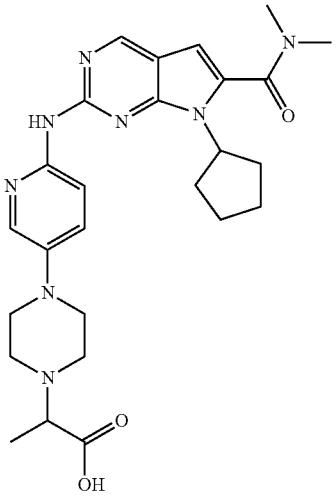 [SMILES: CC(C(=O)O)N1CCN(c2ccc(Nc3ncc4cc(C(=O)N(C)C)n(C5CCCC5)c4n3)nc2)CC1] | 103 |
| 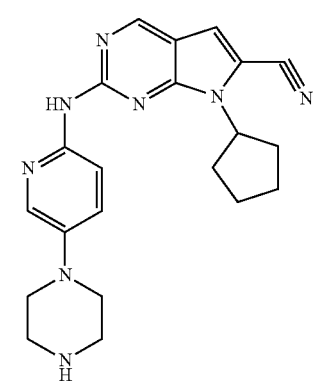 [SMILES: N#Cc1cc2cnc(Nc3ccc(N4CCNCC4)cn3)nc2n1C1CCCC1] | 104 |
| 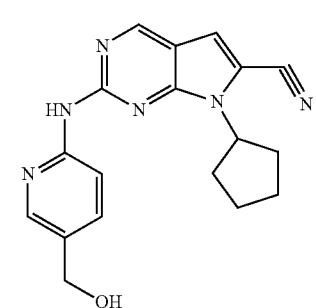 [SMILES: N#Cc1cc2cnc(Nc3ccc(CO)cn3)nc2n1C1CCCC1] | 105 |
| 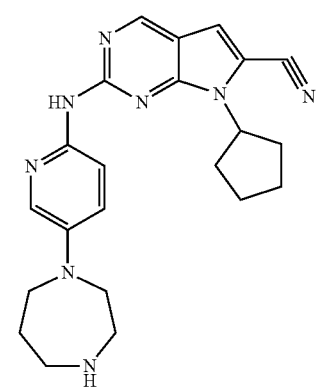 [SMILES: N#Cc1cc2cnc(Nc3ccc(N4CCCNCC4)cn3)nc2n1C1CCCC1] | 106 |

TABLE 1-continued

| Compound | Example Number |
|---|---|
| (structure) | 107 |
| (structure) | 108 |
| (structure) | 109 |
| (structure) | 110 |

Biological Activity

CDK4/Cyclin D1 Enzymatic Activity Assay

A 384-well microtiter Lance TR-FRET (time-resolved—fluorescence energy transfer) endpoint assay was used for CDK4/cyclin D1 kinase activity measurements. The same assay was used for IC50 determination of small molecule inhibitors. In general, the kinase reactions were carried out in 30 μL volumes in the reaction solution containing the following: 2 uL compound (in 20% DMSO), 18 uL CDK4/cyclin D1 in Assay Buffer (50 mM HEPES, pH 7.5, 5 mM MgCl$_2$, 2 mM MnCl$_2$, 1 mM DTT, 0.05% BSA, 0.02% Tween-20), 10 uL of the mixture of pRb152 and ATP. The final reaction mixture contains compound (inhibitor) with the concentration varying from 0.005-101.1M, 2% DMSO, 0.3 nM CDK4/cyclin D1, 175 nM pRb152, and 3 μM ATP (Amersham Pharmacia, Cat. No. 27-2056-01). All reactions were run at room temperature in 384-well white flat-bottom OptiPlates (Perkin Elmer, Cat. No. 6007290) for 60 mM then were quenched by the addition of 10 μL of 120 mM EDTA. The signals were captured by the addition of 40 μL of the Detection Solution containing the following: Detection Buffer (50 mM HEPES, pH 7.5, 30 mM EDTA, 0.1% Triton x-100, 0.05% BSA), 70 ng/mL anti-phospho-pRb(5780) (Cell Signaling Technology, Cat. No. 9307S), 1 nM Lance Eu-W1024-Rabbit anti-IgG (Perkin Elmer, Cat. No. AD0082), and 20 nM SureLight™ Allophycocyanin-Streptavidin (Perkin Elmer, Cat. No. CR130-100). The resulted solutions were incubated at room temperature for 2 hours before read on the Evision Multilabel Reader (Perkin Elmer, Envision 2102-0010). Note: IC$_{50}$<0.005 nM or IC$_{50}$>10 μM indicates the true IC$_{50}$ is out of detection range.

CDk4/cyclin D1 recombinant protein used in the enzymatic activity assay was prepared by coexpressing pDEST10-CDK4 (N-terminal His$_6$) and pFastBacDual-GST-hCyclinD1 viruses in Sf21 cells. The overexpressed protein was purified by Ni-NTA affinity pull down to >80% pure by Sizing HPLC.

CDK1/Cyclin B Enzymatic Activity Assay

A 384-well microtiter IMAP-FP™ (Molecular Devices Trade Mark Technology) endpoint assay was used for CDK1/cyclin B kinase activity measurements. The same assay was used for IC$_{50}$ determination of small molecule inhibitors. In general, the kinase reactions were carried out in 20 μL volumes in the reaction solution, which is composed of 2 μL compound (in 20% DMSO), 8 mL CDK1/cyclin B in the 1× Reaction Buffer (Molecular Devices, Cat. No. R8139), 10 μL substrate mixture of Tamra Histone-H1 peptide (Molecular Devices, Cat. No. R7384) and ATP (Amersham Pharmacia, Cat. No. 27-2056-01) in the 1× Reaction Buffer with 1 mM DTT freshly added. The final reaction mixture contains compound (inhibitor) with the concentration varying from 0.005-10 μM, 2% DMSO, 0.25 nM CDK1/cyclin B, 100 nM Tamra Histone-H1 peptide, and 20 μM ATP.

All reactions were run at room temperature in black 384-well flat-bottom Costar plates (Corning, Cat. No. 3710) for 120 min then were quenched by the addition of 60 μL 400-fold diluted 1× Progressive Binding Buffer A (Molecular Devices, Cat. No. R8139). The fluorescent polarization signals were read on the Evision Multilabel Reader (Perkin Elmer, Envision 2102-0010) after 2-hour incubation at room temperature. Note: IC$_{50}$<0.005 nM or IC$_{50}$>10 indicates the true IC$_{50}$ is out of detection range.

CDK2/Cyclin A Enzymatic Activity Assay

The assay was run under the conditions identical to that for CDK1/cyclin B except 0.25 nM CDK1/cyclin B was replaced with 0.3 nM CDK2/cyclin A. The results of the assays are summarized in table 2.

TABLE 2

| Example No. | CDK4 (μM) | CDK1 (μM) | CDK2 (μM) | MS (MH+) |
|---|---|---|---|---|
| 1 | * | >15 | >15 | 351.1 |
| 74 | *** | >15 | >15 | 435.3 |
| 78 | *** | >15 | >15 | 463.3 |
| 86 | ** | >15 | >15 | 481.3 |
| 26 | ** | >15 | >15 | 479.3 |

TABLE 2-continued

| Example No. | CDK4 (μM) | CDK1 (μM) | CDK2 (μM) | MS (MH+) |
|---|---|---|---|---|
| 14 | ** | >15 | >15 | 493.3 |
| 95 | ** | >15 | >15 | 521.3 |
| 33 | ** | >15 | >15 | 523.4 |
| 57 | ** | >15 | >15 | 493.3 |
| 56 | ** | >15 | >15 | 493.3 |
| 71 | ** | >15 | >15 | 507.3 |
| 21 | *** | >15 | >15 | 493.3 |
| 44 | ** | >15 | >15 | 509.3 |
| 46 | ** | >15 | >15 | 509.3 |
| 29 | ** | 15 | >15 | 509.3 |
| 79 | ** | >15 | >15 | 503.3 |
| 63 | *** | >15 | >15 | 477.3 |
| 36 | ** | >15 | >15 | 493.4 |
| 101 | * | >15 | >15 | 521.4 |
| 103 | ** | >15 | >15 | 507.3 |
| 69 | ** | >15 | >15 | 531.4 |
| 92 | *** | >15 | >15 | 491.3 |
| 99 | ** | >15 | >15 | 505.3 |
| 90 | ** | >15 | >15 | 519.4 |
| 68 | *** | >15 | >15 | 519.4 |
| 25 | ** | >15 | >15 | 517.3 |
| 10 | ** | >15 | >15 | 492.4 |
| 84 | ** | >15 | >15 | 474.3 |
| 9 | ** | >15 | >15 | 488.3 |
| 7 | ** | >15 | >15 | 477.3 |
| 27 | ** | >15 | >15 | 503.3 |
| 23 | ** | >15 | >15 | 545.3 |
| 90 | ** | >15 | >15 | 559.4 |
| 91 | ** | >15 | >15 | 559.4 |
| 12 | ** | >15 | >15 | 492.3 |
| 88 | *** | >15 | >15 | 520.5 |
| 22 | ** | >15 | >15 | 532.3 |
| 94 | ** | >15 | >15 | 546.3 |
| 38 | ** | >15 | >15 | 548.3 |
| 30 | * | >15 | >15 | 549.3 |
| 31 | * | >15 | >15 | 549.3 |
| 19 | *** | >15 | >15 | 448.3 |
| 16 | *** | >15 | >15 | 449.3 |
| 81 | ** | >15 | >15 | 493.3 |
| 17 | ** | >15 | >15 | 449.3 |
| 82 | ** | >15 | >15 | 493.3 |
| 72 | ** | >15 | >15 | 463.3 |
| 24 | ** | >15 | >15 | 463.3 |
| 4 | ** | >15 | >15 | 449.2 |
| 8 | ** | 14 | 8 | 449.3 |
| 13 | ** | >15 | >15 | 435.3 |
| 39 | ** | >15 | >15 | 436.3 |
| 32 | ** | >15 | >15 | 422.5 |
| 59 | ** | >15 | >15 | 423.4 |
| 83 | * | >15 | >15 | 424.2 |
| 10A | ** | 12 | 14 | 436.3 |
| 34 | * | >15 | >15 | 527.4 |
| 42 | ** | >15 | >15 | 449.3 |
| 43 | ** | >15 | >15 | 463.6 |
| 54 | ** | >15 | >15 | 463.3 |
| 55 | ** | >15 | >15 | 463.4 |
| 60 | * | >15 | >15 | 477.4 |
| 61 | * | >15 | >15 | 491.5 |
| 62 | ** | >15 | >15 | 491.4 |
| 65 | ** | >15 | >15 | 506.4 |
| 73 | ** | >15 | >15 | 475.6 |
| 75 | ** | >15 | >15 | 477.2 |
| 76 | ** | >15 | >15 | 464.4 |
| 77 | ** | >15 | >15 | 507.5 |
| 85 | ** | >15 | >15 | 493.4 |
| 66 | ** | >15 | >15 | 438.3 |
| 3 | ** | >15 | >15 | 477.3 |
| 53 | ** | >15 | >15 | 491.3 |
| 49 | ** | >15 | >15 | 463.3 |
| 96 | ** | >15 | >15 | 507.3 |
| 50 | ** | >15 | >15 | 505.5 |
| 87 | ** | 13 | >15 | 478.3 |
| 41 | *** | 14.8 | 4.7 | 451.3 |
| 6 | *** | >15 | >15 | 477.3 |
| 20 | ** | >15 | >15 | 450.3 |
| 35 | ** | 4.7 | 2.9 | 478.3 |
| 52 | ** | >15 | >15 | 434.3 |
| 80 | ** | >15 | >15 | 476.3 |
| 100 | ** | >15 | >15 | 478.3 |
| 45 | * | >15 | 20 | 536.3 |
| 67 | ** | >15 | >15 | 436.3 |
| 70 | ** | >15 | >15 | 478.3 |
| 37 | ** | >15 | >15 | 480.3 |
| 48 | * | >15 | >15 | 436.3 |
| 15 | * | >15 | >15 | 480.6 |
| 40 | * | >15 | >15 | 395.3 |
| 47 | *** | 2.6 | 8.3 | 431.3 |
| 58 | ** | >15 | >15 | 421.2 |
| 51 | ** | >15 | >15 | 463.4 |
| 11 | *** | 1.3 | 3.5 | 431.2 |
| 18 | *** | 1.1 | 2.8 | 445.2 |
| 109 | * | >15 | >15 | 448.5 |
| 110 | * | >15 | >15 | 436.1 |

Key
Greater than 0.1, and less than or equal to 1.0 = *
Greater than 0.01, and less than or equal to 0.1 = **
Greater than 0.001, and less than or equal to 0.01 = ***

What is claimed is:
1. A method for the treatment of cancer by inhibiting cyclin-dependent kinase 4 comprising administering a compound of formula I, or a pharmaceutically acceptable salt thereof, to a subject in need thereof:

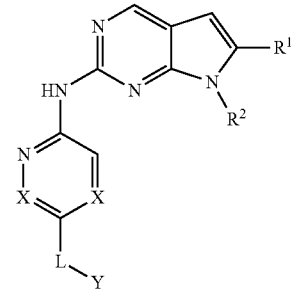

wherein
X is $CR^9$;
$R^1$ is $CONR^5R^6$, and $R^5$ and $R^6$ are $C_{1-8}$alkyl;
$R^2$ is $C_{3-14}$cycloalkyl;
L is a bond, $C_{1-8}$alkylene, C(O), or C(O)NH, and wherein L may be substituted or unsubstituted;
Y is H, OH, or Y is part of the following group

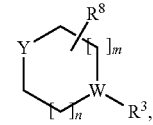

where Y is N and W is $CR^9$, or N;
where 0-2 $R^8$ may be present, and $R^8$ is $C_{1-8}$alkyl, oxo, or two or more $R^8$ may form a bridged alkyl group;
$R^3$ is H, $C_{1-8}$alkyl, $C_{3-14}$cycloalkyl, $C(O)C_{1-8}$ alkyl, $C_{1-8}$alkylOH, $C_{1-8}$cyanoalkyl, $C_{0-8}$alkylC(O)$C_{0-8}$alkylNR$^{14}$R$^{15}$, $C_{0-8}$alkylC(O)OR$^{14}$, NR$^{14}$R$^{15}$, $C_{1-8}$alkylC$_{3-14}$cycloalkyl, C(O)C$_{1-8}$alkylC$_{3-14}$cycloalkyl, $C_{1-8}$alkylR$^{14}$, $C_{1-8}$haloalkyl, or C(O)R$^{14}$, which may be substituted with one or more of OH, CN, F, or $NH_2$, and wherein $R^{14}$ and $R^{15}$ are each independently selected from H, $C_{1-8}$alkyl, $C_{3-14}$cycloalkyl, alkoxy, $C(O)C_{1-3}$alkyl, $C_{1-8}$alkylNH$_2$, or $C_{1-6}$ alkylOH;
$R^9$ is H or halogen;
m and n are independently 0-2; and
wherein L may be substituted with one or more of $C_{1-8}$alkyl, $C_{2-8}$alkenyl, $C_{2-8}$alkynyl, $C_{3-14}$cycloalkyl, 5-14 membered heteroaryl group, $C_{6-14}$aryl group, a 3-14 membered cycloheteroalkyl group, OH, (O), CN, alkoxy, halogen, or NH$_2$.

2. The method according to claim 1 wherein $R^3$ is H, $C_{1-8}$alkyl, or $C_{1-8}$alkylOH, or a pharmaceutically acceptable salt thereof.

3. The method according to claim 1 wherein $R^2$ is cyclopentane; or a pharmaceutically acceptable salt thereof.

4. The method according to claim 1 wherein Y is

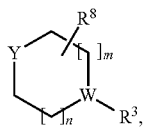

where m and n are 1, and Y and W are N; or a pharmaceutically acceptable salt thereof.

5. A method for the treatment of cancer by inhibiting cyclin-dependent kinase 4 comprising administering a compound of formula I(a), or a pharmaceutically acceptable salt thereof, to a subject in need thereof:

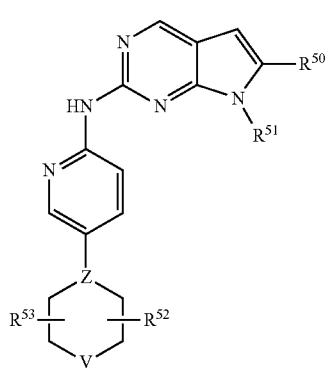

I(a)

or a pharmaceutically acceptable salt thereof, wherein:
$R^{50}$ is CONR$^{54}$R$^{55}$;
$R^{51}$ is $C_{3-14}$cycloalkyl which may be unsubstituted or substituted by $C_{1-3}$alkyl, or OH;
Z is CH or N; and
V is NR$^{56}$ or CHR$^{57}$;
$R^{54}$ and $R^{55}$ are both methyl; and
$R^{52}$, $R^{53}$ $R^{56}$, and $R^{57}$ are H.

6. A method for the treatment of cancer by inhibiting cyclin-dependent kinase 4 comprising administering a compound to a subject in need of thereof wherein the compound is selected from:
7-Cyclopentyl-2-{5-[4-(2-fluoro-ethyl)-piperazin-1-yl]-pyridin-2-ylamino}-7H-pyrrolo[2,3-d]pyrimidine-6-carboxylic acid dimethylamide;
7-Cyclopentyl-2-(4-dimethylamino-3,4,5,6-tetrahydro-2H-[1,3']bipyridinyl-6'-ylamino)-7H-pyrrolo[2,3-d]pyrimidine-6-carboxylic acid dimethylamide;
2-[5-(4-Carbamoylmethyl-piperazin-1-yl)-pyridin-2-ylamino]-7-cyclopentyl-7H-pyrrolo[2,3-d]pyrimidine-6-carboxylic acid dimethylamide;
2-{5-[4-(2-Amino-acetyl)-piperazin-1-yl]-pyridin-2-ylamino}-7-cyclopentyl-7H-pyrrolo[2,3-d]pyrimidine-6-carboxylic acid dimethylamide;
2-[5-(3-Amino-pyrrolidin-1-yl)-pyridin-2-ylamino]-7-cyclopentyl-7H-pyrrolo[2,3-d]pyrimidine-6-carboxylic acid dimethylamide;
7-Cyclopentyl-2-{5-[4-(2-methoxy-ethyl)-piperazin-1-yl]-pyridin-2-ylamino}-7H-pyrrolo[2,3-d]pyrimidine-6-carboxylic acid dimethylamide;
7-Cyclopentyl-2-[4-(2-hydroxyethyl)-3,4,5,6-tetrahydro-2H-[1,2']bipyrazinyl-5'-ylamino]-7H-pyrrolo[2,3-d]pyrimidine-6-carboxylic acid dimethylamide;
7-Cyclopentyl-2-[5-((R)-3-methyl-piperazin-1-yl)-pyridin-2-ylamino]-7H-pyrrolo[2,3-d]pyrimidine-6-carboxylic acid dimethylamide;
7-Cyclopentyl-2-[5-((S)-3-methylpiperazin-1-yl)-pyridin-2-ylamino]-7H-pyrrolo[2,3-d]pyrimidine-6-carboxylic acid dimethylamide;
7-Cyclopentyl-2-[5-(3-methylpiperazin-1-yl)-pyridin-2-ylamino]-7H-pyrrolo[2,3-d]pyrimidine-6-carboxylic acid dimethylamide;
7-Cyclopentyl-2-{5-[4-(3-hydroxypropyl)-piperazin-1-yl]-pyridin-2-ylamino}-7H-pyrrolo[2,3-d]pyrimidine-6-carboxylic acid dimethylamide;
7-Cyclopentyl-2-{5-[4-(pyrrolidine-1-carbonyl)-piperazin-1-yl]pyridin-2-ylamino}-7H-pyrrolo[2,3-d]pyrimidine-6-carboxylic acid dimethylamide;
7-Cyclopentyl-2-{5-[4-(2-hydroxy-ethyl)-piperazin-1-yl]-pyridin-2-ylamino}-7H-pyrrolo[2,3-d]pyrimidine-6-carboxylic acid dimethylamide;
7-Cyclopentyl-2-{5-[4-((S)-2,3-dihydroxypropyl)-piperazin-1-yl]-pyridin-2-ylamino}-7H-pyrrolo[2,3-d]pyrimidine-6-carboxylic acid dimethylamide;
7-Cyclopentyl-2-(5-{4-[2-(2-hydroxyethoxy)-ethyl]-piperazin-1-yl}-pyridin-2-ylamino)-7H-pyrrolo[2,3-d]pyrimidine-6-carboxylic acid dimethylamide;
7-Cyclopentyl-2-{5-[4-(2-hydroxy-1-methylethyl)-piperazin-1-yl]-pyridin-2-ylamino}-7H-pyrrolo[2,3-d]pyrimidine-6-carboxylic acid dimethylamide;
7-Cyclopentyl-2-{6-[4-(2-hydroxyethyl)-piperazin-1-yl]-pyridazin-3-ylamino}-7H-pyrrolo[2,3-d]pyrimidine-6-carboxylic acid dimethylamide;
7-Cyclopentyl-2-{5-[4-(2,3-dihydroxypropyl)-piperazin-1-yl]-pyridin-2-ylamino}-7H-pyrrolo[2,3-d]pyrimidine-6-carboxylic acid dimethylamide;
7-Cyclopentyl-2-{5-[4-((R)-2,3-dihydroxypropyl)-piperazin-1-yl]-pyridin-2-ylamino}-7H-pyrrolo[2,3-d]pyrimidine-6-carboxylic acid dimethylamide;
7-Cyclopentyl-2-(3,4,5,6-tetrahydro-2H-[1,2']bipyrazinyl-5'-ylamino)-7H-pyrrolo[2,3-d]pyrimidine-6-carboxylic acid dimethylamide;
7-Cyclopentyl-2-[5-(piperazine-1-carbonyl)-pyridin-2-ylamino]-7H-pyrrolo[2,3d]pyrimidine-6-carboxylic acid dimethylamide;
7-Cyclopentyl-2-[5-(4-dimethylaminopiperidine-1-carbonyl)-pyridin-2-ylamino]-7H-pyrrolo[2,3-d]pyrimidine-6-carboxylic acid dimethylamide;
7-Cyclopentyl-2-(1',2',3',4',5',6'-hexahydro-[3,4']bipyridinyl-6-ylamino)-7H-pyrrolo[2,3d]pyrimidine-6-carboxylic acid dimethylamide;
7-Cyclopentyl-2-[5-((S)-3-methylpiperazin-1-ylmethyl)-pyridin-2-ylamino]-7Hpyrrolo[2,3-d]pyrimidine-6-carboxylic acid dimethylamide;
7-Cyclopentyl-2-{5-[4-((S)-2-hydroxypropyl)-piperazin-1-yl]-pyridin-2-ylamino}-7H-pyrrolo[2,3-d]pyrimidine-6-carboxylic acid dimethylamide;

7-Cyclopentyl-2-{5-[4-((R)-2-hydroxypropyl)-piperazin-1-yl]-pyridin-2-ylamino}-7H-pyrrolo[2,3-d]pyrimidine-6-carboxylic acid dimethylamide;

7-Cyclopentyl-2-[5-(4-isopropyl-piperazin-1-yl)-pyridin-2-ylamino]-7H-pyrrolo[2,3d]pyrimidine-6-carboxylic acid dimethylamide;

7-Cyclopentyl-2-[5-(4-isopropyl-piperazine-1-carbonyl)-pyridin-2-ylamino]-7H-pyrrolo[2,3-d]pyrimidine-6-carboxylic acid dimethylamide;

7-Cyclopentyl-2-{5-[4-(4-methyl-pentyl)-piperazin-1-yl]-pyridin-2-ylamino}-7H-pyrrolo[2,3-d]pyrimidine-6-carboxylic acid dimethylamide;

7-Cyclopentyl-2-{5-[4-(2-hydroxy-2methylpropyl)-piperazin-1-yl]pyridin-2-ylamino}-7H-pyrrolo[2,3-d]pyrimidine-6-carboxylic acid dimethylamide;

7-Cyclopentyl-2-[5-(3,3-dimethyl-piperazin-1-yl)-pyridin-2-ylamino]-7H-pyrrolo[2,3-d]pyrimidine-6-carboxylic acid dimethylamide;

7-Cyclopentyl-2-[5-(3,8-diaza-bicyclo[3.2.1]oct-3-ylmethyl)-pyridin-2-ylamino]-7H-pyrrolo[2,3-d]pyrimidine-6-carboxylic acid dimethylamide;

7-Cyclopentyl-2-[5-(4-ethyl-piperazin-1-yl)-pyridin-2-ylamino]-7H-pyrrolo[2,3-d]pyrimidine-6-carboxylic acid dimethylamide;

7-Cyclopentyl-2-[5-(4-cyclopentyl-piperazin-1-yl)-pyridin-2-ylamino]-7H-pyrrolo[2,3-d]pyrimidine-6-carboxylic acid dimethylamide;

7-Cyclopentyl-2-(1'-isopropyl-1',2',3',4',5',6'-hexahydro-[3,4']bipyridinyl-6-ylamino)-7H-pyrrolo[2,3-d]pyrimidine-6-carboxylic acid dimethylamide;

7-Cyclopentyl-2-{5-[(R)-4-(2-hydroxyethyl)-3-methyl-piperazin-1-yl]pyridin-2-ylamino}-7H-pyrrolo[2,3-d]pyrimidine-6-carboxylic acid dimethylamide;

7-Cyclopentyl-2-{5-[(S)-4-(2-hydroxyethyl)-3-methyl-piperazin-1-yl]pyridin-2-ylamino}-7H-pyrrolo[2,3-d]pyrimidine-6-carboxylic acid dimethylamide;

7-Cyclopentyl-2-{5-[4-(2-hydroxyethyl)-piperazin-1-ylmethyl]-pyridin-2-ylamino}-7H-pyrrolo[2,3-d]pyrimidine-6-carboxylic acid dimethylamide;

7-Cyclopentyl-2-{5-[4-(2-dimethylaminoacetyl)-piperazin-1-yl]-pyridin-2-ylamino}-7H-pyrrolo[2,3-d]pyrimidine-6-carboxylic acid dimethylamide;

7-Cyclopentyl-2-{5-[4-(2-ethyl-butyl)piperazin-1-yl]pyridin-2-ylamino}-7H-pyrrolo[2,3-d]pyrimidine-6-carboxylic acid dimethylamide;

2-{5-[4-(2-Cyclohexyl-acetyppiperazin-1-yl]pyridin-2-ylamino}-7-cyclopentyl-7H-pyrrolo[2,3-d]pyrimidine-6-carboxylic acid dimethylamide;

7-Cyclopentyl-2-{5-[4-(3-cyclopentyl-propionyl)-piperazin-1-yl]pyridin-2-ylamino}7H-pyrrolo[2,3-d]pyrimidine-6-carboxylic acid dimethylamide;

7-Cyclopentyl-2-[5-(4-isobutylpiperazin-1-yl)-pyridin-2-ylamino]-7H-pyrrolo[2,3d]pyrimidine-6-carboxylic acid dimethylamide;

7-Cyclopentyl-2-{5-[4-(2-isopropoxyethyl)-piperazin-1-yl]pyridin-2-ylamino}-7Hpyrrolo[2,3-d]pyrimidine-6-carboxylic acid dimethylamide;

7-Cyclopentyl-2-{5-[4-(2-methyl-butyl)piperazin-1-yl]-pyridin-2-ylamino}-7H-pyrrolo[2,3-d]pyrimidine-6-carboxylic acid dimethylamide; and 7-Cyclopentyl-2-[1'-(2-hydroxy-ethyl)-1',2',3',4',5',6'-hexahydro-[3,4']bipyridinyl-6-ylamino]-7H-pyrrolo[2,3-d]pyrimidine-6-carboxylic acid dimethylamide;

or a pharmaceutically acceptable salt thereof.

7. The method according to claim 2 wherein $R^3$ is H, methyl, ethyl, propyl, isopropyl, $CH_2OH$, or $CH_2CH_2OH$; or a pharmaceutically acceptable salt thereof.

8. The method according to claim 1 wherein m is 2 and n is 1; or a pharmaceutically acceptable salt thereof.

9. The method according to claim 1 wherein $R^8$ is methyl, ethyl, propyl, butyl, oxo, or two $R^8$ can form a bridged group; or a pharmaceutically acceptable salt thereof.

10. The method according to claim 1 wherein L is a bond an Y is not H; or a pharmaceutically acceptable salt thereof.

11. The method according to claim 1 wherein L is a bond and Y is where m and n are 1 or 2, and Y and W are N; or a pharmaceutically acceptable salt thereof.

12. The method according to claim 11 wherein $R^3$ is H, methyl, ethyl, propyl, isopropyl, $CH_2OH$ or $CH_2CH_2OH$; or a pharmaceutically acceptable salt thereof.

13. The method according to claim 1 wherein the cancer is breast carcinoma.

14. The method according to claim 1 wherein the cancer is colon carcinoma.

15. The method according to claim 1 wherein the cancer is lung carcinoma.

16. The method according to claim 1 wherein the cancer is acute lymphoblastic leukemia.

17. The method according to claim 1 wherein the cancer is chronic myelogenous leukemia.

18. The method according to claim 1 wherein the cancer is melanoma.

19. The method according to claim 1 wherein the cancer is a tumor of mesenchymal origin.

20. The method according to claim 1 wherein the cancer is pancreatic cancer.

21. The method according to claim 1 wherein the cancer is prostate cancer.

22. The method according to claim 1 wherein the cancer is non-small-cell lung cancer.

23. The method according to claim 1 wherein the cancer is mantle cell lymphoma.

* * * * *